(12) United States Patent
Otte et al.

(10) Patent No.: US 8,263,393 B2
(45) Date of Patent: Sep. 11, 2012

(54) MEANS AND METHODS FOR PRODUCING A PROTEIN THROUGH CHROMATIN OPENERS THAT ARE CAPABLE OF RENDERING CHROMATIN MORE ACCESSIBLE TO TRANSCRIPTION FACTORS

(75) Inventors: Arie Pieter Otte, Amersfoort (NL); Theodorus Hendrikus Jacobus Kwaks, Amsterdam (NL); Richard George Antonius Bernardus Sewalt, Arnhem (NL)

(73) Assignee: Chromagenics B.V., Leiden (NL)

( * ) Notice: Subject to any disclaimer, the term of this patent is extended or adjusted under 35 U.S.C. 154(b) by 1707 days.

(21) Appl. No.: 11/156,910

(22) Filed: Jun. 20, 2005

(65) Prior Publication Data

US 2006/0003416 A1 Jan. 5, 2006

Related U.S. Application Data

(63) Continuation of application No. PCT/NL03/00909, filed on Dec. 19, 2003.

(30) Foreign Application Priority Data

Dec. 20, 2002 (EP) .................................. 02080479
Jan. 13, 2003 (EP) .................................. 03075089

(51) Int. Cl.
*C12N 15/00* (2006.01)
*C12N 15/63* (2006.01)
*C07H 21/04* (2006.01)

(52) U.S. Cl. ..................... 435/320.1; 435/455; 536/24.1
(58) Field of Classification Search ........................ None
See application file for complete search history.

(56) References Cited

U.S. PATENT DOCUMENTS

| | | | |
|---|---|---|---|
| 4,965,196 A | 10/1990 | Levinson et al. | |
| 5,021,344 A | 6/1991 | Armau et al. | |
| 5,118,620 A | 6/1992 | Armau et al. | |
| 5,527,701 A | 6/1996 | Yamaguchi et al. | |
| 5,561,053 A | 10/1996 | Crowley | |
| 5,610,053 A | 3/1997 | Chung et al. | |
| 5,627,033 A | 5/1997 | Smith et al. | |
| 5,648,267 A | 7/1997 | Reff | |
| 5,658,763 A | 8/1997 | Dorai et al. | |
| 5,733,779 A | 3/1998 | Reff | |
| 5,773,695 A | 6/1998 | Thompson et al. | |
| 5,888,809 A | 3/1999 | Allison | |
| 5,972,605 A | 10/1999 | Villeponteau et al. | |
| 5,994,128 A | 11/1999 | Fallaux et al. | |
| 6,060,273 A | 5/2000 | Dirks et al. | |
| 6,107,477 A | 8/2000 | Whitney et al. | |
| 6,319,707 B1 | 11/2001 | Adam et al. | |
| 6,395,549 B1 | 5/2002 | Tuan et al. | |
| 6,413,744 B1 | 7/2002 | Morris et al. | |
| 6,521,419 B1 | 2/2003 | Koduri et al. | |
| 6,558,948 B1 | 5/2003 | Kochanek et al. | |
| 6,586,205 B1 | 7/2003 | Glucksmann et al. | |
| 6,800,457 B2 | 10/2004 | Koduri et al. | |
| 6,872,524 B1 | 3/2005 | Otte | |
| 7,001,772 B2 | 2/2006 | Roessler et al. | |
| 7,109,029 B2 | 9/2006 | Clarke et al. | |
| 7,192,741 B2* | 3/2007 | Otte et al. ..................... | 435/70.3 |
| 7,244,609 B2 | 7/2007 | Drocourt et al. | |
| 7,267,965 B2 | 9/2007 | Otte et al. | |
| 7,364,878 B2 | 4/2008 | Otte et al. | |
| 7,655,441 B2 | 2/2010 | Otte et al. | |
| 7,659,094 B2 | 2/2010 | Otte et al. | |
| 7,662,591 B2 | 2/2010 | Otte et al. | |
| 7,736,868 B2 | 6/2010 | Otte et al. | |
| 7,736,869 B2 | 6/2010 | Otte et al. | |
| 7,736,870 B2 | 6/2010 | Otte et al. | |
| 7,749,733 B2 | 7/2010 | Otte et al. | |
| 2002/0155540 A1 | 10/2002 | Padidam | |
| 2003/0138908 A1 | 7/2003 | Koduri et al. | |
| 2003/0166042 A1 | 9/2003 | Glucksmann et al. | |
| 2003/0199468 A1 | 10/2003 | Otte et al. | |
| 2004/0219677 A1 | 11/2004 | Drocourt et al. | |
| 2005/0106609 A1 | 5/2005 | Otte | |
| 2005/0181428 A1 | 8/2005 | Antoniou et al. | |
| 2005/0191723 A1 | 9/2005 | Otte et al. | |
| 2006/0003416 A1 | 1/2006 | Otte et al. | |
| 2006/0010506 A1 | 1/2006 | Otte et al. | |

(Continued)

FOREIGN PATENT DOCUMENTS

EP 0 724 639 1/2001

(Continued)

OTHER PUBLICATIONS

Kawasaki et al in "ATF-2 has intrinsic histone acetyltransferase activity which is modulated by phosphorylation" (Nature, vol. 405, May 11, 2000, pp. 195-200, entire document).*
Bielicki et al in "Expression, purification and characterization of recombinant human N-acetylgalactosamine-6-sulphatase" (in Biochem J. vol. 311, 1995, p. 333-339, entire document).*
Score Report,Seq No. 10 Result 1, for U.S. Appl. No. 10/074,744.*
Score Report,Seq No. 1 Result 1, for Patent 7,192,741.*
SCORE result 1 Seq Id No. 1 Padidam 2001.*
Benkirane et al in "Activation of Integrated Provirus Requires Histone Acetyltransferase" (JBC, 1998: vol. 273, No. 38, pp. 24898-24905).*

(Continued)

*Primary Examiner* — Nancy T Vogel
*Assistant Examiner* — Catherine Hibbert
(74) *Attorney, Agent, or Firm* — TraskBritt

(57) ABSTRACT

Described are means and methods for providing a cell with a protein expression unit, the method comprising providing a nucleic acid sequence comprising the unit with a nucleic acid sequence encoding a binding site for a member of a chromatin modification system for rendering chromatin more accessible for transcription (opener), wherein the opener is present in the cell. Preferred openers comprise histone modification proteins, chromatin remodeling proteins and trithorax group proteins or equivalents. The cells thus generated and nucleic acid sequences encoding such openers are provided. Openers are preferred in the context of STAR and TRAP sequences.

9 Claims, 8 Drawing Sheets

U.S. PATENT DOCUMENTS

| | | | |
|---|---|---|---|
| 2006/0141577 | A1 | 6/2006 | Otte et al. |
| 2006/0172382 | A1 | 8/2006 | Otte et al. |
| 2006/0195935 | A1 | 8/2006 | Otte et al. |
| 2006/0263882 | A1 | 11/2006 | Fazio et al. |
| 2007/0026498 | A1 | 2/2007 | Otte et al. |
| 2007/0026499 | A1 | 2/2007 | Otte et al. |
| 2007/0031933 | A1 | 2/2007 | Otte et al. |
| 2007/0031934 | A1 | 2/2007 | Otte et al. |
| 2007/0031935 | A1 | 2/2007 | Otte et al. |
| 2007/0031936 | A1 | 2/2007 | Otte et al. |
| 2007/0037256 | A1 | 2/2007 | Otte et al. |
| 2007/0128717 | A1 | 6/2007 | Otte et al. |
| 2007/0212755 | A1 | 9/2007 | Otte et al. |
| 2008/0085537 | A1 | 4/2008 | Otte et al. |
| 2008/0206813 | A1 | 8/2008 | Otte et al. |
| 2009/0011468 | A1 | 1/2009 | Otte et al. |
| 2009/0098601 | A1 | 4/2009 | Otte et al. |
| 2010/0136616 | A1 | 6/2010 | Otte et al. |
| 2010/0190207 | A1 | 7/2010 | Otte et al. |

FOREIGN PATENT DOCUMENTS

| | | |
|---|---|---|
| EP | 1 273 666 | 1/2003 |
| WO | WO 91/01374 | 2/1991 |
| WO | WO 94/23046 | 10/1994 |
| WO | WO 96/04390 | 2/1996 |
| WO | WO 96/12008 | 4/1996 |
| WO | WO 97/27207 | 7/1997 |
| WO | WO 98/11207 | 3/1998 |
| WO | WO 98/39411 | 9/1998 |
| WO | WO 98/49289 | 11/1998 |
| WO | WO 00/05393 | 2/2000 |
| WO | WO 00/09749 | 2/2000 |
| WO | WO 00/17337 | 3/2000 |
| WO | WO 00/23606 | 4/2000 |
| WO | WO 01/02553 | 1/2001 |
| WO | WO 01/32901 | 5/2001 |
| WO | WO 01/57188 | 8/2001 |
| WO | WO 01/59117 | 8/2001 |
| WO | WO 01/59118 | 8/2001 |
| WO | WO 02/24930 A2 | 3/2002 |
| WO | WO 02/072846 | 9/2002 |
| WO | WO 02/074969 | 9/2002 |
| WO | WO 02/099070 | 12/2002 |
| WO | WO 02/099089 | 12/2002 |
| WO | WO 03/004704 | 1/2003 |
| WO | WO 03/083077 | 10/2003 |
| WO | WO 03/106684 | 12/2003 |
| WO | WO 2004/027072 | 4/2004 |
| WO | WO 2004/055215 A1 | 7/2004 |
| WO | WO 2004/056986 A2 | 7/2004 |
| WO | WO 2005/040377 | 5/2005 |
| WO | WO 2006/005718 | 1/2006 |
| WO | WO 2006/048459 | 5/2006 |
| WO | WO 2007/096399 | 8/2007 |
| WO | WO 2007/108675 | 9/2007 |

OTHER PUBLICATIONS

Aranda et al., Definition of Transcriptional Pause Elements in Fission Yeast, Molecular and Cellular Biology, Feb. 1999, pp. 1251-1261, vol. 19, No. 2.

Auten et al., "Effect of Scaffold Attachment Region on Transgene Expression in Retrovirus Vector-Transduced Primary T cells and Macrophages," Human Gene Therapy, May 20, 1999, pp. 1389-1399, vol. 10, No. 8.

Glucksmann et al., Database accession No. AAH76193, Oct. 29, 2001.

Han et al., "Matrix attachment regions (MARs) enhance transformation frequency and transgene expression in poplar," Transgenic Research, 1997, pp. 415-420, vol. 6.

Mielke et al., "Stabilized, long-term expression of heterodimeric proteins from tricistronic mRNA," Gene, Aug. 22, 2000, pp. 1-8, vol. 254, No. 1-2.

Migliaccio et al., "Stable and unstable transgene integration sites in the human genome: extinction of the Green Fluorescent Protein transgene in K562 cells," Gene, Oct. 3, 2000, pp. 197-214, vol. 256, No. 1-2.

Bell et al., Insulators and Boundaries: Versatile Regulatory Elements in the Eukaryotic Genome, Science, pp. 447-450, vol. 291, No. 5503.

Chung et al., A 5' Element of the Chicken Beta-Globin Domain Serves as an Insulator in Human Erythroid Cells and Protects against Position Effect in *Drosophila*, Aug. 13, 1993, Cell, pp. 505-514, vol. 74.

Database EMBL 'Online!, Jul. 8, 1992, *H. sapiens* HOX4B gene upstream sequence XP002348163 retrieved from EBI, Database accession No. X67079, Abstract.

Kellum et al., A Group of scs Elements Function as Domain Boundaries in an Enhancer-Blocking Assay, Molecular and Cellular Biology, May 1992, pp. 2424-2431, vol. 12, No. 5.

Partial European Search Report, EP 05 07 6209, dated Oct. 7, 2005.

European Search Report dated Dec. 22, 2005.

Database EMBL 'Online! Aug. 4, 1999, "*Homo sapiens* chromosome 19 clone CTD-2540B15, complete sequence," XP002359985 retrieved from EBI accession No. EM_PRO:AC008738, database accession No. AC008738 for Seq Id No. 7.

Database EMBL 'Online! Feb. 3, 2004, "Sequence 33099 from Patent WO02068579," XP002359986 retrieved from EBI accession No. EM_PRO:CQ747165, database accession No. CQ747165 for Seq Id No. 9.

Database EMBL 'Online! Sep. 24, 2000, "*Homo sapiens* chromosome 4 clone RP11-680118, working draft sequence, 25 unordered pieces," XP002359987 retrieved from EBI accession No. EM_PRO:AC080087, database accession No. AC080087 for Seq Id No. 9.

Database EMBL 'Online! Dec. 15, 1999, "*Homo sapiens* Bac clone RP11-572N21 from 2, complete sequence," XP002359988 retrieved from EBI accession No. EM_PRO:AC018470, database accession No. AC018470, for Seq Id No. 17.

Database EMBL 'Online! 23 Dec. 1999, "Human DNA sequence from clone RP11-54H19 on chromosome I Contains the 3' end of the LMNA gene for lamin A/C, the gene for a novel protein similar to semaphorins (FLJ12287), a novel gene (KIAA0446), the PMFI gene for polyamine-modulated factor I, the BGLAP gene for bone gamma-carboxyglutamate (gla) p," XP002359989, refilled from EBI accession No. EM_PRO:AL135927, database accession No. ALI35927 for Seq Id No. 27.

Database EMBL 'Online! Apr. 26, 2001, "RST28606 Athersys RAGE Library *Homo sapiens* cDNA, mRNA sequence," XP002359990 retrieved from EBI accession No. EM_PRO:BG209092, database accession No. BG209092 for Seq Id No. 40.

Database EMBL 'Online! Sep. 29, 1999, "*Homo sapiens* genomic DNA, chromosome 22q11.2, Cat Eye Syndrome region, clone:N64E9," XP002359991, retrieved from EBI accession No. EM_PRO:AP000526, database accession No. AP000526 for Seq Id No. 40.

Database EMBL 'Online! Oct. 28, 1998, "*Homo sapiens* neurexin III-alpha gene, partial cds," XP002359992, retrieved from EBI accession No. EM_PRO:AF099810, database accession No. AF099810 for Seq Id No. 43.

Database EMBL 'Online! Jan. 25, 2001, "QV2-NN0045-081200-535-c10 NN0045 *Homo sapiens* cDNA, mRNA sequence." XP002359993 retrieved from EBI accession No. EM_PRO:BF960930, database accession No. BF960930 for Seq Id No. 43.

Database EMBL 'Online! Sep. 29, 1999, *Homo sapiens* genomic DNA, chromosome 22q11.2, Cat Eye Syndrome region, clone:N14H11, XP002359994 retrieved from EBI accession No. EM_PRO:AP000525, database accession No. AP000525 for Seq Id No. 44.

Database EMBL 'Online! Mar. 19, 1998, CIT-HSP-2172C8.TF CIT-HSP *Homo sapiens* genomic clone 2172C8, genomic survey sequence, XP002359995 retrieved from EBI accession No. EM_PRO:B92131, database accession No. B9213I for Seq Id No. 44.

Database EMBL 'Online! Sep. 29, 1999, "*Homo sapiens* genomic DNA, chromosome 22q11.2, Cat Eye Syndrome region, clone:c91G6," XP002359996 retrieved from EBI accession No. EM_PRO:AP000528, database accession No. AP000528 for Seq Id No. 45.

Database EMBL 'Online! Mar. 15, 1999, "*Homo sapiens* chromosome UNK clone CTA-435J10, working draft sequence, I unordered pieces," XP002359997 retrieved from EBI accession No. EM_PRO:AC007044, database accession No. AC007044 for Seq Id No. 61.

Emery et al., "A chromatin insulator protects retrovirus vectors from chromosomal position effects," Proceedings of the National Academy of Sciences of USA, Aug. 1, 2000, pp. 9150-9155. vol. 97, No. 16.

West et al., "Insulators: many functions, many mechanisms," Genes and Development, Feb. 1, 2002, pp. 271-288, vol. 16, No. 3.

Kwaks et al., "Indentification of anti-repressor elements that confer high stable protein in production in mammalian cells," Nature Biotechnology, May 20, 2003, pp. 553-558, vol. 21, No. 5.

Pile et al., "GAGA Factor-dependent Transcription and Establishment of DNase Hypersensitivity Are Independent and Unrelated Events in Vivo," J. of Biological Chemistry, Jan. 14, 2000, pp. 1398-1404, vol. 275, No. 2.

Sigrist et al., "Chromatin Insulator Elements Black the Silencing of a Target Gene by the *Drosophila* Polycomb Response Element (PRE) but Allow trans Interactions Between PREs on Different Chromosomes," Genetics, Sep. 1997, pp. 209-211, vol. 147, No. 1.

PCT International Search Report, PCT/NL03/00909, dated Jun. 25, 2004.

PCT International Preliminary Examination Report, PCT/NL03/00909, dated Mar. 22, 2005.

Van Der Vlag et al., Transcription Repression Mediated by Polycomb Group Proteins and Other Chromatin-associated Repressors Is Selectively Blocked by Insulators, Journal of Biological Chemistry, Jan. 7, 2000, pp. 697-704, vol. 275, No. 1.

Maniatis et al., Recognition Sequences of Repressor and Polymerase in the Operators of Bacteriophage Lambda, Cell, Jun. 1975, pp. 109-113, vol. 5.

Reik et at, Biotechnologies and therapeutics: Chromatin as a target, Current Opinion in Genetics & Development, 2002, pp. 233-242, vol. 12.

Eggermont et al., Poly(A) signals and transcriptional pause sites combine to prevent interference between RNA polymerase II promoters, The EMBO Journal, 1993, pp. 2539-2548, vol. 12, No. 6.

Johnson et al., Requirements for utilization of CREB binding protein by hypersensitive site two of the Beta-globin locus control region, Nucleic Acids Research 2002, pp. 1522-1530, vol. 30, No. 7.

Martinez-Balbas et al., The acetyltransferase activity of CBP stimulates transcription, The EMBO Journal, 1998, pp. 2886-2893, vol. 17, No. 10.

Seum et al., A GAL4-HP1 fusion protein targeted near heterochromatin promotes gene silencing, Chromosoma, 2000, pp. 453-459, vol. 109.

Farrell et al., Conserved CTCF Insulator Elements Flank the Mouse and Human Beta-Globin Loci, Molecular and Cellular Biology, Jun. 2002, pp. 3820-3831, vol. 22. No. 11.

Chan et al., p300-CBP proteins: HATs for transcriptional bridges and scaffolds, Journal of Cell Science, 2001, pp. 2363-73, vol. 114.

Burgess-Beusse et al., The insulation of genes from external enhancers and silencing chromatin, PNAS, Dec. 10, 2002, pp. 16433-16437, vol. 99, Suppl. 4.

Bird, et al. Methylation-Induced Repression—Belts, Braces and Chromatin, Cell. Nov. 24, 1999, pp. 451-454, vol. 99.

Carroll. et al., J. Virol 67(3): 1433-1440. 1993.

Database EMBL. Jun. 19, 2002, accession No. AL773524. Human DNA sequence from clone RP11-250K24 on chromosome 9 Contains a calponin 2 (CNN2) pseudogene and a novel pseudogene.

Database EMBL, Aug. 2, 2003, accession No. AC146157, Pantroglodytes BAC clone RP43-2A11 from 7, complete sequence.

Database EMBL, May 26, 2000, accession No. AC069285, *Homo sapiens* BAC clone RP11-196D18 from 7, complete sequence.

Database EMBL, Aug. 9, 2002. accession No. AL845331, Human DNA sequence from clone RP11-407P15 on chromosome 9.

De Boer, et al., Portable Shine-Dalgarno regions: nucleotides between the Shine-Dalgarno sequence and the start codon affect the translation efficiency, Gene Amplification and Analysis. 1983, pp. 103-116, vol. 3.

Dummitt, et al.. N-Terminal Methionine Removal and Methionine Removal and Methionine Metabolism in *Saccharomyces cerevisiae*, Journal of Cellular Biology, 2003, pp. 964-974, vol. 89.

European Search Report for EP 04 10 5593 dated Jun. 21, 2005.

European Search Report for EP 05 07 6209 dated Dec. 22, 2005.

Frengen, et al., Modular bacterial artificial chromosome vectors for transfer of large inserts into mammalian cells. Genomics, vol. 68, No. 2, pp. 118-126. Sep. 2000.

GenBank Accession No. AC007689.13. GI: 8573011, Jun. 25, 2000.

GenBank Accession No. AL021960. GI: 4584387, publicly available Apr. 1999, printed as pp. 1-46.

GenBank Accession No. AL096766.12, GI: 5738627, Aug. 17, 1999.

GenBank Accession No. AL449105, GI: 14268199, publicly available Jun. 2001, printed as pp. 1-47.

GenBank Accession No. AL449105, GI: 46559322, publicly available Jan. 2009, printed as pp. 1-63.

Hellen, et al., Interanl ribosome entry sites in eukaryotic mRNA molecules, Genes and Development, 2001, pp. 1593-1612. vol. 15, Nol. 13, Cold Spring Harbor Laboratory Press.

Henncke, et al., Nucleic Acids Res.. 2001. pp. 3327-3334, vol. 29.

Izumi, et al. Hoingeneous Tetracycline-Regulatable Gene Expression in Mammalian Fibroblasts: Journal of Cellular Biochemistry 76; 1999; pp. 280-289.

Kim. et al.. Poly(A)-dependent Transcription Termination; The Journal of Biological Chemistry; vol. 278, No. 43; Oct. 24, 2003; pp. 41691-41701.

Kozak, Initiation of translation in prokaryotes and cukaryotes, Gene, 1999, pp. 187-208, Vo. 234.

Kozak, M., An analysis of 5'-noncoding sequences from 699 vertebrate messenger RNAs, Nucleic Acids Res.. 1987, pp. 8125-8148. vol. 15. No. 20.

Kozak, M., Context Effects and Inefficient Initiation at Non-AUG Codons in Eucaryotic Cell-Free Translation Systems. Molecular and Cellular biology, Nov. 1989, pp. 5073-5080, vol. 9, No. 11.

Kozak, M., Point Mutations Define a Sequence Flanking the AUG Initiator Docon That Modulates Translation by Eukaryotic Ribosomes, Cell, Jan. 31. 1986, pp. 283-292, vol. 44.

Kozak, M., Recognition of AUG and alternative initiator codons in augmented by G in position +4 but is not generally affected by thenucleotides in positions +5 and +6, The EMBO Journal. 1997, pp. 2482-2492, vol. 16, No. 9.

Kozak, PNAS. 1990. pp. 8301-8305. vol. 87. No. 21.

Kozak, Pushing the limits of the scanning mechanism for initiation of translation. Gene, 2002. pp. 1-34. vol. 299.

Kuhn, et al., Functional Analysis of the Internal Translation Initiation Site of Foot-and-Mouth Disease Virus. Journal of Virology, Oct. 1990, pp. 4625-4631, vol. 64, No. 10.

Kwaks, et al., Employing epigenetics to augment the expression fo the therapeutic proteins in mammalian cells, Trends in Biotechnology, Mar. 2006, pp. 137-142, vol. 24, No. 3.

Kwaks, et al., Targeting of histone acetyltranscerase domain to a promoter enhances protein expression levels in mammalian cells, Journal of Biotechnology, 2005, pp. 35-46, vol. 115.

Lee. et al., Engineering Chinese hamster ovary (CHO) cells to achieve an inverse growth-associated production of a foreign protein. β-galactosidase. Cytotechnology. 1998. pp. 73-80. vol. 28.

Liu. et al.. Construction of Discistronic expression vector in mammalian cell with IRES and dhfr: Bull Acad Mil Med Sci. Mar. 2000: vol. 24. No, 1: pp. 9-11.

Lopez De Quinto. et al.,Parameters influencing translation efficiency in aphthovirus IRES-based bicistronic expression vectors. Gene, 1998, pp. 51-56, vol. 217.

Moser. et al., Biotechnol. Prog. 16: 724-735, 2000.

Otte, et al. Various Expression-Augmenting DNA Elements Benfit from STAR-Select, a Novel High Stingency Selection System from Protein Expression, Biotechnol. Prog., 2007, pp. 801-807, vol. 23.

PCT International Preliminary Examination Report, PCT/NL03/00850, dated Mar. 24. 2005.

PCT International Preliminary Report of Patentability, PCT/EP2005/055794, dated Jan. 26, 2007.

PCT International Preliminary Report of Patentability, PCT/EP2007/053984, dated Jul. 25, 2008.

PCT International Search Report for Application PCT/EP2007/052664, dated May 25, 2007.
PCT International Search Report PCT/EP2007/053984, dated Sep. 6, 2007.
PCT International Search Report, PCT/NL02/00390, dated Jul. 29, 2003.
Pcr International Search Report, PCT/NL03/00432, dated Jan. 9, 2004.
PCT International Search Report, PCT/NL03/00850. dated Jun. 4, 2004.
PCT Written Opinion of the International Searching Authority for Application PCT/EP2007/052664 dated May 25, 2007.
PCT Written Opinion, PCT/EP2007/051696 dated Mar. 5, 2008.
Razin, CpG methylation, chromatin structure and gene silencing-a three-way connection, The EMBO Journal, 1998, pp. 4905-4908, vol. 17, No. 17.
Ress. et al, Biotechniques, 1996, pp. 102-110, vol. 20. No. 1.
Shizuya. et al.. Cloning and stable maintenance of 300-kilbase-pair fragments of human DNA in *Escherichia coli* using an F-factor-based-vector. Proc Natl Acad Sci USA. vol. 89. No. 18. pp. 8794-8797, Sep. 1992.
Tang. et al.. J. Microbiol. Methods, 2003, pp. 231-38, vol. 52.
Van Blokland, et al., a novel, high stringency selection system allows screening of few clones for high protein expression, Journal of Biotechnology, 2007, pp. 237-245. vol. 128.
Wells, et al., Codon optimization, gentic insulation, and an rtTA reporter improve performance of the tetracycline switch**. Transgenic Research 8; 1999; pp. 371-381.
Williams, et al., CpG-island fragments from the HNRPA2B1/CVX3 genomics locus reduce silencing and enhance transgene expression from the hCMV promoter/enhancer in mammalian cells, published Jun. 3, 2005, <http://www.biomedcentral.conn/1472-6750/5/17>.
Yew. et al.. Molecular Therapy. 2002, pp. 731-738. vol. 5.
Zeocin™, Instruction Manual, Version J. Aug. 22, 2002.
Office Action for U.S. Appl. No. 11/013,031 dated Jul. 3, 2007.
Office Action for U.S. Appl. No. 11/156,910 dated Apr. 15, 2010.
Office Action for U.S. Appl. No. 11/156,910 dated Feb. 11, 2008.
Office Action for U.S. Appl. No. 11/156,910 dated Sep. 18, 2009.
Office Action for U.S. Appl. No. 11/269,525 dated Apr. 5, 2010.
Office Action for U.S. Appl. No. 11/269,525 dated Aug. 5, 2008.
Office Action for U.S. Appl. No. 11/269,525 dated Feb. 9, 2009.
Office Action for U.S. Appl. No. 11/269,525 dated Oct. 23, 2009.
Office Action for U.S. Appl. No. 11/359,953 dated Aug. 6, 2009.
Office Action for U.S. Appl. No. 11/359,953 dated Jan. 14, 2010.
Office Action for U.S. Appl. No. 11/359,953 dated Nov. 26, 2008.
Office Action for U.S. Appl. No. 11/416,490 dated Jan. 29, 2009.
Office Action for U.S. Appl. No. 11/416,490 dated Oct. 8, 2009.
Office Action for U.S. Appl. No. 11/580,494 dated Mar. 23, 2009.
Office Action for U.S. Appl. No. 11/580,604 dated Mar. 20, 2009.
Office Action for U.S. Appl. No. 11/580,604 dated Nov. 4, 2009.
Office Action for U.S. Appl. No. 11/580,605 dated Mar. 20, 2009.
Office Action for U.S. Appl. No. 11/580,619 dated Mar. 23, 2009.
Office Action for U.S. Appl. No. 11/580,620 dated Mar. 23, 2009.
Office Action for U.S. Appl. No. 11/580,644 dated Mar. 20, 2009.
Office Action for U.S. Appl. No. 11/580,760 dated Mar. 23, 2009.
Office Action for U.S. Appl. No. 11/580,760 dated Nov. 4, 2009.
Office Action for U.S. Appl. No. 11/632,012 dated Apr. 29, 2009.
Office Action for U.S. Appl. No. 11/632,012 dated Mar. 26, 2010.
Office Action for U.S. Appl. No. 11/888,568 dated Dec. 11, 2008.
Office Action for U.S. Appl. No. 11/888,568 dated Jul. 6, 2010.
Office Action for U.S. Appl. No. 11/978,483 dated Aug. 21, 2008.
Office Action for U.S. Appl. No. 11/978,483 dated Jan. 11, 2010.
Office Action for U.S. Appl. No. 11/978,483 dated Jul. 15, 2009.
Notice of Allowance for U.S. Appl. No. 11/013,031 dated Jan. 15, 2008.
Notice of Allowance for U.S. Appl. No. 11/580,494 dated Nov. 25, 2009.
Notice of Allowance for U.S. Appl. No. 11/580,604 dated Nov. 3, 2009.
Notice of Allowance for U.S. Appl. No. 11/580,605 dated Dec. 2, 2009.
Notice of Allowance for U.S. Appl. No. 11/580,619 dated Dec. 2, 2009.
Notice of Allowance for U.S. Appl. No. 11/580,620 dated Dec. 2, 2009.
Notice of Allowance for U.S. Appl. No. 11/580,644 dated Nov. 4, 2009.
Notice of Allowance for U.S. Appl. No. 11/580,760 dated Nov. 4, 2009.
GenBank Accession AY237385.1 (AA089266, GI:37933202), accessed on Jul. 23, 2008.
Kaufman, et al., Improved vectors for stable expression of foreign genes in mammalian cells by use of the untranslated leader sequence from EMC virus, Nucleic Acids Research, 1991, pp. 4485-4490, vol. 19, No. 16.
Youn, et al.; An Intronic Silencer of the Mouse Perforin Gene, Mol. Cells., 2001, pp. 61-68, vol. 33, No. 1.

* cited by examiner

FIG 1
Schematic diagram of the invention
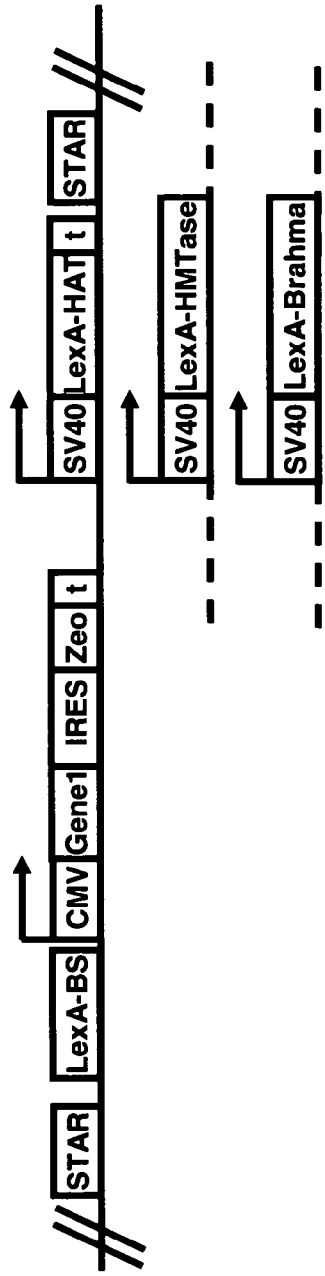
FIG 1A
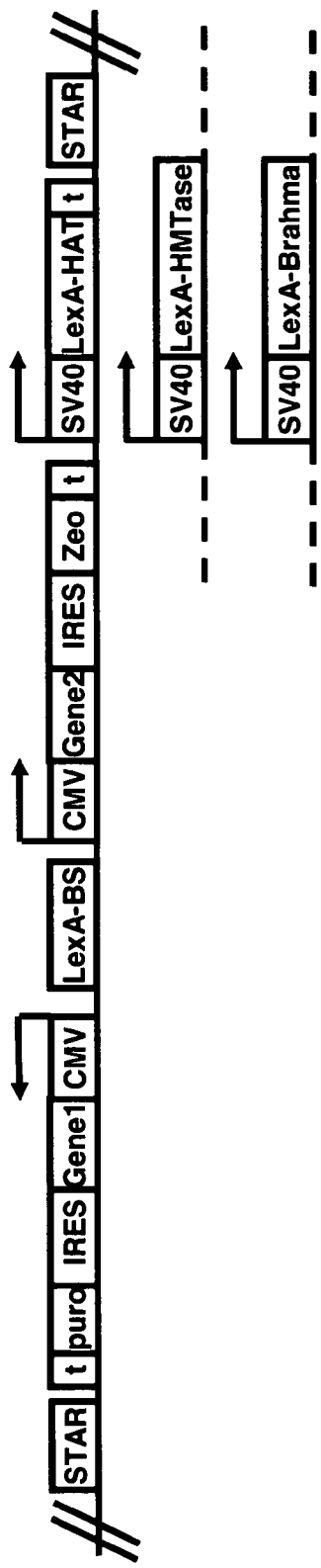
FIG 1B

The effect of the LexA-P/CAF OPENER on CMV promoter driven GFP expression in CHO cells

The combination of OPENERs and STARs enhances CMV promoter driven GFP expression in CHO cells

The combined action of OPENERs and STARs enhances the stability of CMV promoter driven GFP expression in CHO cells The LexA-P300 HAT OPENER does not enhance transient expression levels of CMV and UB6 promoters but only of a minimal promoter The LexA-P300 HAT Opener enhances CMV promoter driven expression levels in stably transfected colonies, but only for a limited period

A

B

The LexA-P300 HAT Opener plus STAR7 enhances UB6 promoter driven expression levels in stably transfected colonies, for a prolonged time period The combination of the LexA-P300 HAT Opener plus STAR7 improves copy number dependency of gene expression

SEQUENCE LISTING

```
<160> NUMBER OF SEQ ID NOS: 44

<210> SEQ ID NO 1
<211> LENGTH: 1586
<212> TYPE: DNA
<213> ORGANISM: Homo sapiens
<220> FEATURE:
<221> NAME/KEY: misc_feature
<223> OTHER INFORMATION: sequence of STAR 4

<400> SEQUENCE: 1
gatctgagtc atgttttaag gggaggattc ttttggctgc tgagttgaga ttaggttgag      60
ggtagtgaag gtaaaggcag tgagaccacg tagggggtcat tgcagtaatc caggctggag     120
atgatggtgg ttcagttgga atagcagtgc atgtgctgta acaacctcag ctgggaagca     180
gtatatgtgg cgttatgacc tcagctggaa cagcaatgca tgtggtggtg taatgacccc     240
agctgggtag ggtgcatgtg atggaacaac ctcagctggg tagcagtgta cttgataaaa     300
tgttggcata ctctagattt gttatgaggg tagtgccatt aaatttctcc acaaattggt     360
tgtcacgtat gagtgaaaag aggaagtgat ggaagacttc agtgcttttg gcctgaataa     420
atagaagacg tcatttccag ttaatggaga cagggaagac taaaggtagg gtgggattca     480
gtagagcagg tgttcagttt tgaatatgat gaactctgag agaggaaaaa cttttttctac    540 ctcttagttt ttgtgactgg acttaagaat taaagtgaca taagacagag taacaagaca     600
aaaatatgcg aggttattta atattttac ttgcagaggg gaatcttcaa aagaaaaatg      660
aagacccaaa gaagccatta gggtcaaaag ctcatatgcc tttttaagta gaaaatgata     720
aattttaaca atgtgagaag acaaaggtgt ttgagctgag ggcaataaat tgtgggacag     780
tgattaagaa atatatgggg gaaatgaaat gataagttat tttagtagat ttattcttca     840
tatctatttt ggcttcaact tccagtctct agtgataaga atgttcttct cttcctggta     900
cagagagagc acctttctca tgggaaattt tatgaccttg ctgtaagtag aaagggggaag    960 atctcctgtt tcccagcatc aggatgcaaa catttccctc cattccagtt ctcaacccca    1020
tggctgggcc tcatggcatt ccagcatcgc tatgagtgca cctttcctgc aggctgcctc   1080
gggtagctgg tgcactgcta ggtcagtcta tgtgaccagg agctgggcct ctgggcaatg   1140
ccagttggca gcccccatcc ctccactgct gggggcctcc tatccagaag ggcttggtgt   1200
gcagaacgat ggtgcaccat catcattccc cacttgccat ctttcagggg acagccagct   1260
gctttgggcg cggcaaaaaa cacccaactc actcctcttc aggggcctct ggtctgatgc   1320
caccacagga catccttgag tgctgggcag tctgaggaca gggaaggagt gatgaccaca   1380
aaacaggaat ggcagcagca gtgacaggag gaagtcaaag gcttgtgtgt cctggccctg   1440
```

```
ctgagggctg gcgagggccc tgggatggcg ctcagtgcct ggtcggctgc aagaggccag    1500
ccctctgccc atgaggggag ctggcagtga ccaagctgca ctgccctggt ggtgcatttc    1560
ctgccccact ctttccttct aagatc                                         1586

<210> SEQ ID NO 2
<211> LENGTH: 1176
<212> TYPE: DNA
<213> ORGANISM: Homo sapiens
<220> FEATURE:
<221> NAME/KEY: misc_feature
<223> OTHER INFORMATION: sequence of STAR 6

<400> SEQUENCE: 2
gatctgaccc accacagaca tcccctctgg cctcctgagt ggtttcttca gcacagcttc      60
cagagccaaa ttaaacgttc actctatgtc tatagacaaa aagggttttg actaaactct     120
gtgttttaga gagggagtta aatgctgtta acttttttagg ggtgggcgag aggaatgaca    180
aataacaact tgtctgaatg ttttacattt ctccccactg cctcaagaag gttcacaacg     240
aggtcatcca tgataaggag taagacctcc cagccggact gtccctcggc ccccagagga    300
cactccacag agatatgcta actggacttg agactggct cacactccag agaaaagcat     360
ggagcacgag cgcacagagc agggccaagg tcccagggac agaatgtcta ggagggagat    420
tggggtgagg gtaatctgat gcaattactg tggcagctca acattcaagg gaggggaag    480 aaagaaacag tccctgtcaa gtaagttgtg cagcagagat ggtaagctcc aaaatttgaa    540
actttggctg ctggaaagtt ttagggggca gagataagaa gacataagag actttgaggg    600
tttactacac actagacgct ctatgcattt atttattttat tatctcttat ttattacttt    660
gtataactct tataataatc ttatgaaaac ggaaaccctc atatacccat tttacagatg    720
agaaaagtga caattttgag agcatagcta agaatagcta gtaagtaaag gagctgggac    780
ctaaaccaaa ccctatctca ccagagtaca cactcttttt ttattccagt gtaatttttt    840
ttaattttta ttttacttta agttctggga tacatgtgca gaaggtatgg tttgttacat    900
aggtatatgt gtgccatagt ggattgctgc acctatcaac ccgtcatcta ggtttaagcc    960
ccacatgcat tagctatttg tcctgatgct ctccctcccc tccccacacc agacaggcct   1020
tggtgtgtga tgttcccctc cctgtgtcca tgtgttctca ctgttcagct cccacttatg   1080
agtgagaaca tgtggtattt ggttttctgt tcctgtgtta gtttgctgag gatgatggct   1140
tccagcttca tccatgtccc tgcaaggac acgatc                              1176

<210> SEQ ID NO 3
<211> LENGTH: 2094
<212> TYPE: DNA
<213> ORGANISM: Homo sapiens
<220> FEATURE:
<221> NAME/KEY: misc_feature
<223> OTHER INFORMATION: sequence of STAR 7

<400> SEQUENCE: 3
gatcacccga ggtcaggagt tcaagaccag cctggccaac atggtaaaac ctcgtctcta      60
ctaaaaaaat acgaaaaatt agctggttgt ggtggtgcgt gcttgtaatc ccagctactc     120
gggaggctga ggcaggagaa tcacttgaat ctggaggca gaggttgcag tgagctgaga     180
tagtgccatt gcactccagc ctgggcaaca gacggagact ctgtctccaa aaaaaaaaa    240 aaaaatctta gaggacaaga atggctctct caaacttttg aagaaagaat aaataatta    300 tgcagttcta gaagaagtaa tggggatata ggtgcagctc atgatgagga agacttagct    360
```

```
taactttcat aatgcatctg tctggcctaa gacgtggtga gcttttatg tctgaaaaca    420 ttccaatata gaatgataat aataatcact tctgaccccc cttttttttc ctctccctag    480
actgtgaagc agaaacccca tattttcctt agggaagtgg ctacgcactt tgtatttata    540
ttaacaacta ccttatcagg aaattcatat tgttgcccct ttatggatgg ggaaactgga    600
caagtgacag agcaaaatcc aaacacagct ggggatttcc ctcttttaga tgatgatttt    660
aaaagaatgc tgccagagag attcttgcag tgttggagga catatatgac ctttaagata    720
ttttccagct cagagatgct atgaatgtat cctgagtgca tggatggacc tcagttttgc    780
agattctgta gcttatacaa tttggtggtt ttctttagaa gaaaataaca catttataaa    840
tattaaaata ggcccaagac cttacaaggg cattcataca aatgagaggc tctgaagttt    900
gagtttgttc actttctagt taattatctc ctgcctgttt gtcataaatg cgtttagtag    960
ggagctgcta atgacaggtt cctccaacag agtgtggaag aaggagatga cggctggctt   1020
cccctctggg acagcctcag agctagtggg gaaactatgt tagcagagtg atgcagtgac   1080
caagaaaata gcactaggag aaagctggtc catgagcagc tggtgagaaa aggggtggta   1140
atcatgtatg ccctttcctg ttttattttt tattgggttt ccttttgcct ctcaattcct   1200
tctgacaata caaaatgttg gttggaacat ggagcacctg gaagtctggt tcattttctc   1260
tcagtctctt gatgttctct cgggttcact gccattgtt ctcagttcta cacttgagca    1320
atctcctcaa tagctaaagc ttccacaatg cagattttgt gatgacaaat tcagcatcac   1380
ccagcagaac ttaggttttt ttctgtcctc cgtttcctga cctttttctt ctgagtgctt   1440
tatgtcacct cgtgaaccat ccttccctta gtcatctacc tagcagtcct gattcttttg   1500
acttgtctcc ctacaccaca ataaatcact aattactatg gattcaatcc ctaaaatttg   1560
cacaaacttg caaatagatt acgggttgaa acttagagat ttcaaacttg agaaaaagt    1620 ttaaatcaag aaaaatgacc tttaccttga gagtagaggc aatgtcattt ccaggaataa   1680
ttataataat attgtgttta atatttgtat gtaacatttg aataccttca atgttcttat   1740
ttgtgttatt ttaatctctt gatgttacta actcatttgg tagggaagaa acatgctaa    1800 aataggcatg agtgtcttat taaatgtgac aagtgaatag atggcagaag gtggattcat   1860
attcagtttt ccatcaccct ggaaatcatg cggagatgat ttctgcttgc aaataaaact   1920
aacccaatga ggggaacagc tgttcttagg tgaaaacaaa acaaacacgc caaaaacctt   1980
tattctcttt attatgaatc aaattttttcc tctcagataa ttgttttatt tatttatttt   2040
tattattatt gttattatgt ccagtctcac tctgtcgcct aagctggcat gatc          2094
```

<210> SEQ ID NO 4
<211> LENGTH: 1031
<212> TYPE: DNA
<213> ORGANISM: Homo sapiens
<220> FEATURE:
<221> NAME/KEY: misc_feature
<223> OTHER INFORMATION: sequence of STAR 12

<400> SEQUENCE: 4

```
atcctgcttc tgggaagaga gtggcctccc ttgtgcaggt gactttggca ggaccagcag     60
aaacccaggt ttcctgtcag gaggaagtgc tcagcttatc tctgtgaagg gtcgtgataa    120
ggcacgagga ggcaggggct tgccaggatg ttgccttct gtgccatatg ggacatctca     180
gcttacgttg ttaagaaata tttggcaaga agatgcacac agaatttctg taacgaatag    240
gatggagttt taagggttac tacgaaaaaa agaaaactac tggagaagag ggaagccaaa    300
```

```
caccaccaag tttgaaatcg attttattgg acgaatgtct cactttaaat ttaaatggag      360
tccaacttcc ttttctcacc cagacgtcga gaaggtggca ttcaaaatgt ttacacttgt      420
ttcatctgcc tttttgctaa gtcctggtcc cctacctcct ttccctcact tcacatttgt      480
cgtttcatcg cacacatatg ctcatcttta tatttacata tatataattt ttatatatgg      540
cttgtgaaat atgccagacg agggatgaaa tagtcctgaa aacagctgga aaattatgca      600
acagtgggga gattgggcac atgtacattc tgtactgcaa agttgcacaa cagaccaagt      660
ttgttataag tgaggctggg tggttttttat tttttctcta ggacaacagc ttgcctggtg      720
gagtaggcct cctgcagaag gcattttctt aggagcctca acttcccaa gaagaggaga       780 gggcgagact ggagttgtgc tgcagcaca gagacaaggg ggcacggcag gactgcagcc       840
tgcagagggg ctggagaagc ggaggctggc acccagtggc cagcgaggcc caggtccaag      900
tccagcgagg tcgaggtcta gagtacagca aggccaaggt ccaaggtcag tgagtctaag      960
gtccatggtc agtgaggctg agacccaggg tccaatgagg ccaaggtcca gagtccagta     1020
aggccgagat c                                                          1031

<210> SEQ ID NO 5
<211> LENGTH: 995
<212> TYPE: DNA
<213> ORGANISM: Homo sapiens
<220> FEATURE:
<221> NAME/KEY: misc_feature
<223> OTHER INFORMATION: sequence of STAR 18

<400> SEQUENCE: 5
ctaaaggcat tttatataga gctgtggttt ttgtggttta cctgtggccg tggccagagg       60
ttcctgggag gctaacaggt gtttttttgag ggttggggct tgggtggggg tggggtgaat     120
tctctgtttc taggatgtgc ttggtgtttg aatctaggct ttagtgactg atgctggtta      180
atttctaggg ttgatggttt attgggcctt gtgttgtatg agatggaatt ttaaatattt      240
ttaaatgttt ctctagttct tagagaaatt tttaagcaac tcaagatagg ctcttcccgc      300
atatgataat ccgtcaggtg aatttggatt cttttatatc acaaaatgaa tccatgtttt      360
gggaggtaat ggtatcagaa tatatggtgc aggtcttggt aaaaacccaa tagatctttg      420
agaaatacaa gacatctctg tgttgaaaca tcgtgtgttt cttatttgcc agagtaggaa      480
aagagtagat cttttttgctc tctaaatgta ttgatgggtt gtgttttttt tcccacctgc     540
taataaatat tacattgcaa cattcttccc tcaacttcaa aactgctgaa ctgaaacaat      600
atgcataaaa gaaaatcctt tgcagaagaa aaaaagctat tttctcccac tgattttgaa      660
tggcacttgc ggatgcagtt cgcaaatcct attgcctatt ccctcatgaa cattgtgaaa      720
tgaaaccttt ggacagtctg ccgcattgcg catgagactg cctgcgcaag gcaagggtat      780
ggttcccaaa gcacccagtg gtaaatccta acttattatt cccttaaaat tccaatgtaa      840
caacgtgggc cataaaagag tttctgaaca aaacatgtca ctttgtggaa aggtgttttt      900
cgtaattaat gatggaatca tgctcatttc aaaatggagg tccacgattt gtggccagct      960
gatgcctgca aattatcctg gatcactaac tctga                                995

<210> SEQ ID NO 6
<211> LENGTH: 891
<212> TYPE: DNA
<213> ORGANISM: Homo sapiens
<220> FEATURE:
<221> NAME/KEY: misc_feature
<223> OTHER INFORMATION: sequence of STAR 35
```

```
<400> SEQUENCE: 6
cgacttggtg atgcgggctc ttttttggtt ccatatgaac tttaaagtag tcttttccaa      60
ttctgtgaag aaagtcattg gtaggttgat ggggatggca ttgaatctgt aaattacctt     120
gggcagtatg gccattttca caatgttgat tcttcctatc catgatgatg gaatgttctt     180
ccattagttt gtatcctctt ttatttcctt gagcagtggt tgtagttct ccttgaagag      240
gtccttcaca tcccttgtaa gttggattcc taggtatttt attctctttg aagcaattgt     300
gaatgggagt tcactcacga tttggctctc tgtttgtctg ctggtgtata agaatgtttg     360
tgattttttgt acattgattt tgtatcctga gactttgctg aagttgctta tcagcttaag    420
gagcttttgg gctgagacaa tgggattttc tagatataca atcatgtcgt ctgcaaacag     480
ggacaatttg acttcctctt ttcctaattg aatacacttt atctccttct cctgcctaat     540
tgccctgggc agaacttcca acactatgtt gaataggagt ggtgagagag ggcatccctg     600
tcttgtgcca gttttcaaag ggaatgcttc cagttttgc ccattcagta tgatattggc      660
tgtgggtttg tcatagatag ctcttattat tttgaaatgt gtcccatcaa tacctaattt     720
attgagagtt tttagcatga agcattgttg aattttgtca aaggctttttt ctgcatctat    780
tgagataatc atgtggtttt tgtctttggc tctgtttata tgctggatta catttattga     840
tttgtgtata ttgaaccagc cttgcatccc agggatgaag cccacttgat c              891

<210> SEQ ID NO 7
<211> LENGTH: 1031
<212> TYPE: DNA
<213> ORGANISM: Homo sapiens
<220> FEATURE:
<221> NAME/KEY: misc_feature
<223> OTHER INFORMATION: sequence of STAR 40

<400> SEQUENCE: 7
gatcaagaaa gcactccggg ctccagaagg agccttccag gccagctttg agcataagct      60
gctgatgagc agtgagtgtc ttgagtagtg ttcagggcag catgttacca ttcatgcttg     120
acttctagcc agtgtgacga gaggctggag tcaggtctct agagagttga gcagctccag     180
ccttagatct cccagtctta tgcggtgtgc ccattcgctt tgtgtctgca gtcccctggc     240
cacacccagt aacagttctg ggatctatgg gagtagcttc cttagtgagc tttcccttca     300
aatactttgc aaccaggtag agaagtttgg agtgaaggtt ttgttcttcg tttcttcaca     360
atatggatat gcatcttctt ttgaaaatgt taaagtaaat tacctctctt ttcagatact     420
gtcttcatgc gaacttggta tcctgtttcc atcccagcct tctataaccc agtaacatct     480
tttttgaaac cagtgggtga gaaagacacc tggtcaggaa cgcggaccac aggacaactc     540
aggctcaccc acggcatcag actaaaggca acaaggact ctgtataaag taccggtggc      600
atgtgtatta gtggagatgc agcctgtgct ctgcagacag ggagtcacac agacactttt     660
ctataatttc ttaagtgctt tgaatgttca agtagaaagt ctaacattaa atttgattga     720
acaattgtat attcatggaa tatttggaa cggaatacca aaaaatggca atagtggttc      780
tttctggatg gaagacaaac ttttcttctt taaaataaat tttattttat atatttgagg     840
ttgaccacat gaccttaagg atacatatag acagtaaact ggttactaca gtgaagcaaa     900
ttaacatatc taccatcgta catagttaca ttttttttgtg tgacaggaac agctaaaatc    960
tacgtattta acaaaactcc taaagacaat acatttttat taactatagc cctcatgatg    1020
tacattagat c                                                          1031
```

```
<210> SEQ ID NO 8
<211> LENGTH: 2398
<212> TYPE: DNA
<213> ORGANISM: Bacteriophage lambda
<220> FEATURE:
<221> NAME/KEY: misc_feature
<223> OTHER INFORMATION: lambda fragment 35711-38103

<400> SEQUENCE: 8
agatctgaat tgctatgttt agtgagttgt atctatttat ttttcaataa atacaattgg      60
ttatgtgttt tgggggcgat cgtgaggcaa agaaaacccg gcgctgaggc cgggttattc     120
ttgttctctg gtcaaattat atagttggaa acaaggatg catatatgaa tgaacgatgc      180
agaggcaatg ccgatggcga tagtgggtat catgtagccg cttatgctgg aaagaagcaa     240
taacccgcag aaaaacaaag ctccaagctc aacaaaacta agggcataga caataactac     300
cgatgtcata tacccatact ctctaatctt ggccagtcgg cgcgttctgc ttccgattag     360
aaacgtcaag gcagcaatca ggattgcaat catggttcct gcatatgatg acaatgtcgc     420
cccaagacca tctctatgag ctgaaaaaga acaccagga atgtagtggc ggaaaaggag     480
atagcaaatg cttacgataa cgtaaggaat tattactatg taaacaccag gcatgattct     540
gttccgcata attactcctg ataattaatc cttaactttg cccacctgcc ttttaaaaca     600
ttccagtata tcacttttca ttcttgcgta gcaatatgcc atctcttcag ctatctcagc     660
attggtgacc ttgttcagag gcgctgagag atggcctttt tctgatagat aatgttctgt     720
taaaatatct ccggcctcat cttttgcccg caggctaatg tctgaaaatt gaggtgacgg     780
gttaaaaata atatccttgg caacctttt tatatccctt ttaaattttg gcttaatgac     840
tatatccaat gagtcaaaaa gctccccttc aatatctgtt gccctaaga cctttaatat      900 atcgccaaat acaggtagct tggcttctac cttcaccgtt gttcggccga tgaaatgcat     960
atgcataaca tcgtctttgg tggttcccct catcagtggc tctatctgaa cgcgctctcc    1020
actgcttaat gacattcctt tcccgattaa aaaatctgtc agatcggatg tggtcggccc    1080
gaaaacagtt ctggcaaaac caatggtgtc gccttcaaca acaaaaaag atgggaatcc     1140 caatgattcg tcatctgcga ggctgttctt aatatcttca actgaagctt tagagcgatt    1200
tatcttctga accagactct tgtcatttgt tttggtaaag agaaaagttt ttccatcgat    1260
tttatgaata tacaaataat tggagccaac ctgcaggtga tgattatcag ccagcagaga    1320
attaaggaaa acagacaggt ttattgagcg cttatctttc cctttatttt tgctgcggta    1380
agtcgcataa aaaccattct tcataattca atccatttac tatgttatgt ctgagggga    1440 gtgaaaattc ccctaattcg atgaagattc ttgctcaatt gttatcagct atgcgccgac    1500
cagaacacct tgccgatcag ccaaacgtct cttcaggcca ctgactagcg ataactttcc    1560
ccacaacgga acaactctca ttgcatggga tcattgggta ctgtgggttt agtggttgta    1620
aaaacacctg accgctatcc ctgatcagtt tcttgaaggt aaactcatca cccccaagtc    1680
tggctatgca gaaatcacct ggctcaacag cctgctcagg gtcaacgaga attaacattc    1740
cgtcaggaaa gcttggcttg gagcctgttg gtgcggtcat ggaattacct tcaacctcaa    1800
gccagaatgc agaatcactg gcttttttgg ttgtgcttac ccatctctcc gcatcacctt    1860
tggtaaaggt tctaagctca ggtgagaaca tccctgcctg aacatgagaa aaaacagggt    1920
actcatactc acttctaagt gacggctgca tactaaccgc ttcatacatc tcgtagattt    1980
ctctggcgat tgaagggcta aattcttcaa cgctaacttt gagaattttt gcaagcaatg    2040
cggcgttata agcattttaat gcattgatgc cattaaataa agcaccaacg cctgactgcc    2100
```

```
ccatccccat cttgtctgcg acagattcct gggataagcc aagttcattt ttctttttt    2160 cataaattgc tttaaggcga cgtgcgtcct caagctgctc ttgtgttaat ggtttctttt    2220
ttgtgctcat acgttaaatc tatcaccgca agggataaat atctaacacc gtgcgtgttg    2280
actattttac ctctggcggt gataatggtt gcatgtacta aggaggttgt atggaacaac    2340
gcataaccct gaaagattat gcaatgcgct ttgggcaaac caagacagct aaagatct     2398
```

<210> SEQ ID NO 9
<211> LENGTH: 5557
<212> TYPE: DNA
<213> ORGANISM: Bacteriophage lambda
<220> FEATURE:
<221> NAME/KEY: misc_feature
<223> OTHER INFORMATION: Lambda fragment 22425-27972

<400> SEQUENCE: 9

```
ctgcagatct ggaaattgca acgaaggaag aaacctcgtt gctggaagcc tggaagaagt      60
atcgggtgtt gctgaaccgt gttgatacat caactgcacc tgatattgag tggcctgctg     120
tccctgttat ggagtaatcg ttttgtgata tgccgcagaa acgttgtatg aaataacgtt     180
ctgcggttag ttagtatatt gtaaagctga gtattggttt atttggcgat tattatcttc     240
aggagaataa tggaagttct atgactcaat tgttcatagt gtttacatca ccgccaattg     300
cttttaagac tgaacgcatg aaatatggtt tttcgtcatg ttttgagtct gctgttgata     360
tttctaaagt cggttttttt tcttcgtttt ctctaactat tttccatgaa atacattttt     420
gattattatt tgaatcaatt ccaattacct gaagtctttc atctataatt ggcattgtat     480
gtattggttt attggagtag atgcttgctt ttctgagcca tagctctgat atccaaatga     540
agccataggc atttgttatt ttggctctgt cagctgcata acgccaaaaa atatatttat     600
ctgcttgatc ttcaaatgtt gtattgatta aatcaattgg atggaattgt ttatcataaa     660
aaattaatgt ttgaatgtga taaccgtcct ttaaaaaagt cgtttctgca agcttggctg     720
tatagtcaac taactcttct gtcgaagtga tatttttagg cttatctacc agttttagac     780
gctctttaat atcttcagga attattttat tgtcatattg tatcatgcta aatgacaatt     840
tgcttatgga gtaatctttt aatttttaaat aagttattct cctggcttca tcaaataaag     900
agtcgaatga tgttggcgaa atcacatcgt cacccattgg attgtttatt tgtatgccaa     960
gagagttaca gcagttatac attctgccat agattatagc taaggcatgt aataattcgt    1020
aatcttttag cgtattagcg acccatcgtc tttctgattt aataatagat gattcagtta    1080
aatatgaagg taatttcttt tgtgcaagtc tgactaactt ttttataccaa atgtttaaca    1140 tactttcatt tgtaataaac tcaatgtcat tttcttcaat gtaagatgaa ataagagtag    1200
cctttgcctc gctatacatt tctaaatcgc cttgttttc tatcgtattg cgagaatttt    1260
tagcccaagc cattaatgga tcatttttcc atttttcaat aacattattg ttataccaaa    1320
tgtcatatcc tataatctgg ttttttgttt tttgaataat aaatgttact gttcttgcgg    1380
tttggaggaa ttgattcaaa ttcaagcgaa ataattcagg gtcaaaatat gtatcaatgc    1440
agcatttgag caagtgcgat aaatctttaa gtcttctttc ccatggtttt ttagtcataa    1500
aactctccat tttgataggt tgcatgctag atgctgatat attttagagg tgataaaatt    1560
aactgcttaa ctgtcaatgt aatacaagtt gtttgatctt gcaatgatt cttatcagaa    1620 accatatagt aaattagtta cacaggaaat tttaatatt attattatca ttcattatgt    1680
attaaaatta gagttgtggc ttggctctgc taacacgttg ctcataggag atatggtaga    1740
gccgcagaca cgtcgtatgc aggaacgtgc tgcggctggc tggtgaactt ccgatagtgc    1800
```

```
gggtgttgaa tgatttccag ttgctaccga ttttacatat tttttgcatg agagaatttg   1860
taccacctcc caccgaccat ctatgactgt acgccactgt ccctaggact gctatgtgcc   1920
ggagcggaca ttacaaacgt ccttctcggt gcatgccact gttgccaatg acctgcctag   1980
gaattggtta gcaagttact accggatttt gtaaaaacag ccctcctcat ataaaagta    2040 ttcgttcact tccgataagc gtcgtaattt tctatctttc atcatattct agatccctct   2100
gaaaaaatct tccgagtttg ctaggcactg atacataact cttttccaat aattggggaa   2160
gtcattcaaa tctataatag gtttcagatt tgcttcaata aattctgact gtagctgctg   2220
aaacgttgcg gttgaactat atttccttat aacttttacg aaagagtttc tttgagtaat   2280
cacttcactc aagtgcttcc ctgcctccaa acgatacctg ttagcaatat ttaatagctt   2340
gaaatgatga agagctctgt gtttgtcttc ctgcctccag ttcgccgggc attcaacata   2400
aaaactgata gcacccggag ttccggaaac gaaatttgca tacccattt gctcacgaaa    2460 aaaaatgtcc ttgtcgatat agggatgaat cgcttggtgt acctcatcta ctgcgaaaac   2520
ttgacctttc tctcccatat tgcagtcgcg gcacgatgga actaaattaa taggcatcac   2580
cgaaaattca ggataatgtg caataggaag aaaatgatct atattttttg tctgtcctat   2640
atcaccacaa aatggacatt tttcacctga tgaaacaagc atgtcatcgt aatatgttct   2700
agcgggtttg ttttttatctc ggagattatt ttcataaagc ttttctaatt taacctttgt   2760
caggttacca actactaagg ttgtaggctc aagagggtgt gtcctgtcgt aggtaaataa   2820
ctgacctgtc gagcttaata ttctatattg ttgttctttc tgcaaaaaag tggggaagtg   2880
agtaatgaaa ttatttctaa catttatctg catcatacct tccgagcatt tattaagcat   2940
ttcgctataa gttctcgctg gaagaggtag ttttttcatt gtactttacc ttcatctctg   3000
ttcattatca tcgcttttaa aacggttcga ccttctaatc ctatctgacc attataattt   3060
tttagaatgg tttcataaga aagctctgaa tcaacggact gcgataataa gtggtggtat   3120
ccagaatttg tcacttcaag taaaaacacc tcacgagtta aaacacctaa gttctcaccg   3180
aatgtctcaa tatccggacg gataatattt attgcttctc ttgaccgtag gactttccac   3240
atgcaggatt ttggaacctc ttgcagtact actggggaat gagttgcaat tattgctaca   3300
ccattgcgtg catcgagtaa gtcgcttaat gttcgtaaaa aagcagagag caaaggtgga   3360
tgcagatgaa cctctggttc atcgaataaa actaatgact tttcgccaac gacatctact   3420
aatcttgtga tagtaaataa aacaattgca tgtccagagc tcattcgaag cagatatttc   3480
tggatattgt cataaaacaa tttagtgaat ttatcatcgt ccacttgaat ctgtggttca   3540
ttacgtctta actcttcata tttagaaatg aggctgatga gttccatatt tgaaaagttt   3600
tcatcactac ttagtttttt gatagcttca agccagagtt gtcttttct atctactctc    3660 atacaaccaa taaatgctga aatgaattct aagcggagat cgcctagtga ttttaaacta   3720
ttgctggcag cattcttgag tccaatataa aagtattgtg tacctttttgc tgggtcaggt   3780 tgttctttag gaggagtaaa aggatcaaat gcactaaacg aaactgaaac aagcgatcga   3840
aaatatccct ttgggattct tgactcgata agtctattat tttcagagaa aaatattca    3900 ttgttttctg ggttggtgat tgcaccaatc attccattca aaattgttgt tttaccacac   3960
ccattccgcc cgataaaagc atgaatgttc gtgctgggca tagaattaac cgtcacctca   4020
aaaggtatag ttaaatcact gaatccggga gcacttttc tattaaatga aaagtggaaa    4080
tctgacaatt ctggcaaacc atttaacaca cgtgcgaact gtccatgaat ttctgaaaga   4140 gttaccctc taagtaatga ggtgttaagg acgctttcat tttcaatgtc ggctaatcga    4200
```

```
tttggccata ctactaaatc ctgaatagct ttaagaaggt tatgtttaaa accatcgctt    4260
aatttgctga gattaacata gtagtcaatg cttccaccta aggaaaaaaa catttcaggg    4320
agttgactga atttttatc tattaatgaa taagtgctta cttcttcttt ttgacctaca     4380
aaaccaattt taacatttcc gatatcgcat ttttcaccat gctcatcaaa gacagtaaga    4440
taaaacattg taacaaagga atagtcattc caaccatctg ctcgtaggaa tgccttattt    4500
ttttctactg caggaatata cccgcctctt tcaataacac taaactccaa catatagtaa    4560
cccttaattt tattaaaata accgcaattt atttggcggc aacacaggat ctctcttttta   4620 agttactctc tattacatac gttttccatc taaaaattag tagtattgaa cttaacgggg    4680
catcgtattg tagttttcca tatttagctt tctgcttcct tttggataac ccactgttat    4740
tcatgttgca tggtgcactg tttataccaa cgatatagtc tattaatgca tatatagtat    4800
cgccgaacga ttagctcttc aggcttctga agaagcgttt caagtactaa taagccgata    4860
gatagccacg gacttcgtag ccatttttca taagtgttaa cttccgctcc tcgctcataa    4920
cagacattca ctacagttat ggcggaaagg tatgcatgct gggtgtgggg aagtcgtgaa    4980 agaaagaag tcagctgcgt cgtttgacat cactgctatc ttcttactgg ttatgcaggt     5040
cgtagtgggt ggcacacaaa gctttgcact ggattgcgag ctttgtgct tctctggagt     5100 gcgacaggtt tgatgacaaa aaattagcgc aagaagacaa aaatcacctt gcgctaatgc    5160
tctgttacag gtcactaata ccatctaagt agttgattca tagtgactgc atatgttgtg    5220
ttttacagta ttatgtagtc tgttttttat gcaaaatcta atttaatata ttgatattta    5280
tatcatttta cgtttctcgt tcagcttttt tatactaagt tggcattata aaaaagcatt    5340
gcttatcaat ttgttgcaac gaacaggtca ctatcagtca aaataaaatc attatttgat    5400
ttcaattttg tcccactccc tgcctctgtc atcacgatac tgtgatgcca tggtgtccga    5460
cttatgcccg agaagatgtt gagcaaactt atcgcttatc tgcttctcat agagtcttgc    5520
agacaaactg cgcaactcgt gaaaggtagg cggatcc                             5557

<210> SEQ ID NO 10
<211> LENGTH: 154
<212> TYPE: DNA
<213> ORGANISM: Artificial
<220> FEATURE:
<223> OTHER INFORMATION: A combined synthetic polyA (SPA) sequence
      (version 1) and a pausing signal from the human a2 globin gene

<400> SEQUENCE: 10
aataaaatat ctttattttc attacatctg tgtgttggtt ttttgtgtga atcgatagta     60
ctaacatacg ctctccatca aaacaaaacg aaacaaaaca aactagcaaa ataggctgtc    120
cccagtgcaa gtgcaggtgc cagaacattt ctct                                154

<210> SEQ ID NO 11
<211> LENGTH: 154
<212> TYPE: DNA
<213> ORGANISM: Artificial
<220> FEATURE:
<223> OTHER INFORMATION: A combined synthetic polyA (SPA) sequence
      (version 2) and a pausing signal from the human a2 globin gene

<400> SEQUENCE: 11
aataaaagat ccttattttc actagttctg tgtgttggtt ttttgtgtga atcgatagta     60
ctaacatacg ctctccatca aaacaaaacg aaacaaaaca aactagcaaa ataggctgtc    120
cccagtgcaa gtgcaggtgc cagaacattt ctct                                154
```

<210> SEQ ID NO 12
<211> LENGTH: 870
<212> TYPE: DNA
<213> ORGANISM: Homo sapiens
<220> FEATURE:
<221> NAME/KEY: misc_feature
<223> OTHER INFORMATION: Inter histone H3FA-H4F
      (http://genome.ucsc.edu/cgi-bin/hgTracks?hgsid=13148179&position=
      chr6%3A26063) (Chromosome 6; bp 26063887-26064766)

<400> SEQUENCE: 12

```
tatttgagga cactaacctg tgcgccatcc acgccaagcg cgtcactatc atgcccaagg      60
acatccagct cgcccgccgc atccgcggag agagggcgtg attactgtgg tctctctgac     120
ggtccaagca aaggctcttt tcagagccac caccttttca agtaaagtag ctgtaagaaa     180
ccaatttaag acaaaaggga atgcattggg agcacttttc gttttaatgc tactgaaggc     240
ttcaaaacca atcgatttcg gccggtcgcg gtgactcacg cctgtaattc aagcactttg     300
agaggctgag gcgggcggat taccagaaat caggagttcg ggatcagcct ggccaacatg     360
gccgaatccc gtctctacga aaatacaaa aacacgccgg gcgcgacggc gagcgcttgt      420
aatcccagct acactctgaa ggctgaggca ggagaaacac ttgaacctga gaggcagagg     480
tttcagtgaa tcgagatggc tctaatgtac tccagtctgg gcgacagaga gattcggtta     540
aaaaaaaagt tcgacttaaa ataattctgg agtcagaatg ggtttacatt taattcttaa     600
cccagttcct caaagcctgt agctctgtta agaaaataaa ggccattggt caagcctgct     660
tggtcccacc ctcatctccc caccctcccc caatcgctgc tcccgccatt tcctggggct     720
tggaggaggg gttaaaggag cggactgtag gcgtcacatt tcccgcctgc gcgcttttca     780
gtctcagtgt ccgctggagg tggggcagg ggtaacgtag atatataaag atcggtttcc      840
tattctctca cttgctcttg gttcacttct                                       870
```

<210> SEQ ID NO 13
<211> LENGTH: 1173
<212> TYPE: DNA
<213> ORGANISM: Homo sapiens
<220> FEATURE:
<221> NAME/KEY: misc_feature
<223> OTHER INFORMATION: Inter histone H1F4-H2BFB (chr6:26214737-
      26215909)

<400> SEQUENCE: 13

```
aaggcgccca agagcccagc gaaggccaaa gcagttaaac ccaaggcggc taaaccaaag      60
accgccaagc ccaaggcagc caagccaaag aaggcggcag ccaagaaaaa gtagaaagtt     120
cctttggcca actgcttaga agcccaacac aacccaaagg ctcttttcag agccacccac     180
cgctctcagt aaaagagctg ttgcactatt aggggcgtg gctcgggaaa acgctgctaa      240 gcagggcgg gtctcccggg aacaaagtcg gggagaggag tgggattttg tgtgtctccg      300
gagctatttt tgactaaggc gtcgcgtcgc ccaagccgga gtgcagtggc gtcatctcga     360
ttttgcgttc tcgagtgtcg gagttgaacc catttgggcc tcccttgtgc tttgcactttt    420 tagcaggccc tggcctccag atagcatggg aaaaaaaatg ttgggatttt cccgggtttc     480
taagctgggt ttttccgagt tccaaacacg gcacagtgta tcagtttctg tgctggttac     540
aagcctactg gttatcccta tcgagtatgg caggcagtga gggacttcag aggagtacgt     600
cttaggacaa gtggcatagt actgacatta tttccgaagg gctacatttc aagtgcttgg     660
ggagactact gccacataac tgaaaattag aaaccgacac tgcagaaaaa tacttggtcc     720
```

```
ttaaatgtgg catttggatg gattaaggac ttgccgaaac gtaaaactga cagacttggg      780 gggggggat gtcccaatta gcacggcttc tgtatgcaac gagtcccata ctttgttaaa       840
ggaagaaagg aatgtgagtt ctcctaatct gttaagtatc tttcggtgta agttctgaca      900
ccacaatgtt aaaaaagtcg gatctcaaaa accaactgct ccaagcgaag tgcacagctg      960
tcttgcctaa agaggcctat ttatagtagc ctcgggtagt ctggtctggg ctttctcatt      1020
gggtacaagt aaaggaacga aatagccaat gaaaaggtag acttttaagt gtcgtttaca     1080
ttggcatttg tgacgacact ctaaaattaa tccaatcata aacgaaatct gattaacctc      1140
atttgaatac cgcatctata aatgaacagg gcc                                    1173

<210> SEQ ID NO 14
<211> LENGTH: 17
<212> TYPE: DNA
<213> ORGANISM: Artificial
<220> FEATURE:
<223> OTHER INFORMATION: one GAL4 operator

<400> SEQUENCE: 14
cggagtactg tcctccg                                                     17

<210> SEQ ID NO 15
<211> LENGTH: 26
<212> TYPE: DNA
<213> ORGANISM: Artificial
<220> FEATURE:
<223> OTHER INFORMATION: oligonucleotide for making linker for
      pd2EGFP-link

<400> SEQUENCE: 15
gtacggatat cagatcttta attaag                                           26

<210> SEQ ID NO 16
<211> LENGTH: 24
<212> TYPE: DNA
<213> ORGANISM: Artificial
<220> FEATURE:
<223> OTHER INFORMATION: oligonucleotide for making linker for
      pd2EGFP-link

<400> SEQUENCE: 16
gtaccttaat taaagatctg atat                                             24

<210> SEQ ID NO 17
<211> LENGTH: 52
<212> TYPE: DNA
<213> ORGANISM: Artificial
<220> FEATURE:
<223> OTHER INFORMATION: primer for amplification of 0.37 kb region
      from pd2EGFP

<400> SEQUENCE: 17
gatcagatct ggcgcgccat ttaaatcgtc tcgcgcgttt cggtgatgac gg              52

<210> SEQ ID NO 18
<211> LENGTH: 41
<212> TYPE: DNA
<213> ORGANISM: Artificial
<220> FEATURE:
<223> OTHER INFORMATION: primer for amplification of 0.37 kb region
      from pd2EGFP

<400> SEQUENCE: 18
aggcggatcc gaatgtattt agaaaaataa acaaataggg g                          41
```

```
<210> SEQ ID NO 19
<211> LENGTH: 36
<212> TYPE: DNA
<213> ORGANISM: Artificial
<220> FEATURE:
<223> OTHER INFORMATION: primer for amplification of zeocin resistance
      ORF

<400> SEQUENCE: 19
gatcggatcc ttcgaaatgg ccaagttgac cagtgc                              36

<210> SEQ ID NO 20
<211> LENGTH: 32
<212> TYPE: DNA
<213> ORGANISM: Artificial
<220> FEATURE:
<223> OTHER INFORMATION: primer for amplification of zeocin resistance
      ORF

<400> SEQUENCE: 20
aggcgcggcc gcaattctca gtcctgctcc tc                                  32

<210> SEQ ID NO 21
<211> LENGTH: 31
<212> TYPE: DNA
<213> ORGANISM: Artificial
<220> FEATURE:
<223> OTHER INFORMATION: primer for SEAP reporter ORF amplification

<400> SEQUENCE: 21
gatcgaattc tcgcgacttc gcccaccatg c                                   31

<210> SEQ ID NO 22
<211> LENGTH: 47
<212> TYPE: DNA
<213> ORGANISM: Artificial
<220> FEATURE:
<223> OTHER INFORMATION: primer for SEAP reporter ORF amplification

<400> SEQUENCE: 22
aggcgaattc accggtgttt aaactcatgt ctgctcgaag cggccgg                  47

<210> SEQ ID NO 23
<211> LENGTH: 31
<212> TYPE: DNA
<213> ORGANISM: Artificial
<220> FEATURE:
<223> OTHER INFORMATION: primer for introduction p2EGFP

<400> SEQUENCE: 23
gatcgaattc atggtgagca agggcgagga g                                   31

<210> SEQ ID NO 24
<211> LENGTH: 40
<212> TYPE: DNA
<213> ORGANISM: Artificial
<220> FEATURE:
<223> OTHER INFORMATION: primer for introduction p2EGFP

<400> SEQUENCE: 24
aggcacgcgt gttaacctac acattgatcc tagcagaagc                          40

<210> SEQ ID NO 25
<211> LENGTH: 42
<212> TYPE: DNA
<213> ORGANISM: Artificial
<220> FEATURE:
```

```
<223> OTHER INFORMATION: primer Brm-a1F-H3-AgeI

<400> SEQUENCE: 25
gatcaagctt accggtatgt ccacgcccac agaccctggt gc                          42

<210> SEQ ID NO 26
<211> LENGTH: 38
<212> TYPE: DNA
<213> ORGANISM: Artificial
<220> FEATURE:
<223> OTHER INFORMATION: primer Brm-a1572R-XbaI

<400> SEQUENCE: 26
aggctctaga atcactcatc atccgtccca cttccttc                               38

<210> SEQ ID NO 27
<211> LENGTH: 30
<212> TYPE: DNA
<213> ORGANISM: Artificial
<220> FEATURE:
<223> OTHER INFORMATION: primer LBS-for-SalI

<400> SEQUENCE: 27
aggcgtcgac gtttcgactc ccaagctttg                                        30

<210> SEQ ID NO 28
<211> LENGTH: 32
<212> TYPE: DNA
<213> ORGANISM: Artificial
<220> FEATURE:
<223> OTHER INFORMATION: primer LBS-rev-AscI

<400> SEQUENCE: 28
gatcggcgcg ccggtaccat agcggccgcg ac                                     32

<210> SEQ ID NO 29
<211> LENGTH: 32
<212> TYPE: DNA
<213> ORGANISM: Artificial
<220> FEATURE:
<223> OTHER INFORMATION: primer LexA-for-H3

<400> SEQUENCE: 29
gatcaagctt atgaagacgt taacggccag gc                                     32

<210> SEQ ID NO 30
<211> LENGTH: 35
<212> TYPE: DNA
<213> ORGANISM: Artificial
<220> FEATURE:
<223> OTHER INFORMATION: primer LexA-rev-AgeI

<400> SEQUENCE: 30
aggcaccggt cagccagtcg ccgttgcgaa taacc                                  35

<210> SEQ ID NO 31
<211> LENGTH: 33
<212> TYPE: DNA
<213> ORGANISM: Artificial
<220> FEATURE:
<223> OTHER INFORMATION: oligo Link-for-Bsu

<400> SEQUENCE: 31
gatctcccct gaggaagtgc acaacctgag gcc                                    33

<210> SEQ ID NO 32
```

```
<211> LENGTH: 33
<212> TYPE: DNA
<213> ORGANISM: Artificial
<220> FEATURE:
<223> OTHER INFORMATION: oligo Link-rev-Bsu

<400> SEQUENCE: 32
gatctggcct caggttgtgc acttcctcag ggg                          33

<210> SEQ ID NO 33
<211> LENGTH: 38
<212> TYPE: DNA
<213> ORGANISM: Artificial
<220> FEATURE:
<223> OTHER INFORMATION: primer PCAF-a1F-h3-AgeI

<400> SEQUENCE: 33
gatcaagctt accggtatgt ccgaggctgg cggggccg                     38

<210> SEQ ID NO 34
<211> LENGTH: 36
<212> TYPE: DNA
<213> ORGANISM: Artificial
<220> FEATURE:
<223> OTHER INFORMATION: primer PCAF-a833R-XbaI

<400> SEQUENCE: 34
aggctctaga atcacttgtc aattaatcca gcttcc                       36

<210> SEQ ID NO 35
<211> LENGTH: 36
<212> TYPE: DNA
<213> ORGANISM: Artificial
<220> FEATURE:
<223> OTHER INFORMATION: primer p300-a934F-AgeI

<400> SEQUENCE: 35
gatcaccggt cagcctgcaa ctccactttc ccagcc                       36

<210> SEQ ID NO 36
<211> LENGTH: 38
<212> TYPE: DNA
<213> ORGANISM: Artificial
<220> FEATURE:
<223> OTHER INFORMATION: primer p300-a1652R-NheI

<400> SEQUENCE: 36
aggcgctagc ctacatggtg gaccactggg ctcttcgg                     38

<210> SEQ ID NO 37
<211> LENGTH: 37
<212> TYPE: DNA
<213> ORGANISM: Artificial
<220> FEATURE:
<223> OTHER INFORMATION: primer HuAsh1,aa1787-For

<400> SEQUENCE: 37
gatcaccggt acaagcagct gttcccccca tcatatc                      37

<210> SEQ ID NO 38
<211> LENGTH: 39
<212> TYPE: DNA
<213> ORGANISM: Artificial
<220> FEATURE:
<223> OTHER INFORMATION: primer HuAsh1,aa2393-Rev

<400> SEQUENCE: 38
```
aggcgctagc tcataatgat gctgagtgaa tattatcac                              39

<210> SEQ ID NO 39
<211> LENGTH: 40
<212> TYPE: DNA
<213> ORGANISM: Artificial
<220> FEATURE:
<223> OTHER INFORMATION: primer for amplification of (Clontech 6010-1)

<400> SEQUENCE: 39
gatcgaattc tcgcgaatgg tgagcaagca gatcctgaag                             40

<210> SEQ ID NO 40
<211> LENGTH: 52
<212> TYPE: DNA
<213> ORGANISM: Artificial
<220> FEATURE:
<223> OTHER INFORMATION: primer for amplification of (Clontech 6010-1)

<400> SEQUENCE: 40
aggcgaattc accggtgttt aaacttacac ccactcgtgc aggctgccca gg               52

<210> SEQ ID NO 41
<211> LENGTH: 32
<212> TYPE: DNA
<213> ORGANISM: Artificial
<220> FEATURE:
<223> OTHER INFORMATION: primer for amplification of LexA from plasmid
      pEG202

<400> SEQUENCE: 41
gatcaagctt atgaagacgt taacggccag gc                                     32

<210> SEQ ID NO 42
<211> LENGTH: 35
<212> TYPE: DNA
<213> ORGANISM: Artificial
<220> FEATURE:
<223> OTHER INFORMATION: primer for amplification of LexA from plasmid
      pEG202

<400> SEQUENCE: 42
aggcaccggt cagccagtcg ccgttgcgaa taacc                                  35

<210> SEQ ID NO 43
<211> LENGTH: 34
<212> TYPE: DNA
<213> ORGANISM: Artificial
<220> FEATURE:
<223> OTHER INFORMATION: primer for amplification of UB6 promoter

<400> SEQUENCE: 43
gatcggtacc ggcgcgcctc cgcgccgggt tttg                                   34

<210> SEQ ID NO 44
<211> LENGTH: 30
<212> TYPE: DNA
<213> ORGANISM: Artificial
<220> FEATURE:
<223> OTHER INFORMATION: primer for amplification of UB6 promoter

<400> SEQUENCE: 44
aggcgagctc ggtaccaagc ttcgtctaac                                        30

MEANS AND METHODS FOR PRODUCING A PROTEIN THROUGH CHROMATIN OPENERS THAT ARE CAPABLE OF RENDERING CHROMATIN MORE ACCESSIBLE TO TRANSCRIPTION FACTORS

CROSS-REFERENCE TO RELATED APPLICATION

This application is a continuation of PCT International Patent Application No. PCT/NL2003/000909, filed on Dec. 19, 2003, designating the United States of America, and published, in English, as PCT International Publication No. WO 2004/056986 A2 on Jul. 8, 2004. PCT/NL2003/000909 itself claims priority to EP 02080479.5, filed Dec. 20, 2002, and EP 03075089.7 filed Jan. 13, 2003, the contents of the entirety of all three of which are incorporated herein by this reference.

TECHNICAL FIELD

The invention relates to the fields of biotechnology, biochemistry, molecular biology, and pharmacology. More specifically, the present invention relates to the production of proteins in a host cell. In one embodiment, the invention relates to methods for improving the predictability, yield and/or stability of the production of proteins in a (host) cell. Methods herein are suited for production of one or more proteins.

BACKGROUND

Proteins are produced in systems for a wide range of applications in biology and biotechnology. These include research into cellular and molecular function, production of proteins as biopharmaceuticals or diagnostic reagents, and modification of the traits or phenotypes of livestock and crops. Biopharmaceuticals are usually proteins that have an extracellular function, such as antibodies for immunotherapy, or hormones or cytokines for eliciting a cellular response. Proteins with extracellular functions exit the cell via a secretory pathway, and undergo post-translational modifications during secretion (Chevet et al., 2001). The modifications (primarily glycosylation and disulfide bond formation) do not naturally occur in bacteria. Moreover, the specific oligosaccharides attached to proteins by glycosylating enzymes are typically species and cell-type specific. These considerations often limit the choice of host cells for heterologous protein production to eukaryotic cells (Kaufman, 2000). For expression of human therapeutic proteins, host cells such as bacteria, yeast, or plants may be inappropriate. Even the subtle differences in protein glycosylation between rodents and human, for example, can be sufficient to render proteins produced in rodent cells unacceptable for therapeutic use (Sheeley et al., 1997). The consequences of improper (i.e., non-human) glycosylation include immunogenicity, reduced functional half-life, and loss of activity. For proteins where this is a problem, the choice of host cells is limited further to human cell lines or to cell lines such as Chinese Hamster Ovary (CHO) cells, which may produce glycoproteins with human-like carbohydrate structures (Liu, 1992).

Some proteins of biotechnological interest are functional as multimers, i.e., they consist of two or more possibly different polypeptide chains in their biologically and/or biotechnologically active form. Examples include antibodies (Wright and Morrison, 1997), bone morphogenetic proteins (Groeneveld and Burger, 2000), nuclear hormone receptors (Aranda and Pascual, 2001), heterodimeric cell surface receptors (e.g., T cell receptors (Chan and Mak, 1989)), integrins (Hynes, 1999), and the glycoprotein hormone family (chorionic gonadotrophin, pituitary luteinizing hormone, follicle-stimulating hormone, and thyroid-stimulating hormone (Thotakura and Blithe, 1995)). Production of such multimeric proteins in heterologous systems is technically difficult due to a number of limitations of current expression systems. These limitations include: (1) difficulties in isolating recombinant cells/cell lines that produce the monomer polypeptides at high levels (predictability and yield) and (2) declines in the levels of expression during the industrial production cycle of the proteins (stability). These problems are described in more detail below.

(1) Recombinant proteins, such as antibodies that are used as therapeutic compounds, need to be produced in large quantities. The host cells used for recombinant protein production must be compatible with the scale of the industrial processes that are employed. Specifically, the transgene (or the gene encoding a protein of interest, the two terms being used interchangeably herein) expression system used for the heterologous protein needs to be retained by the host cells in a stable and active form during the growth phases of scale-up and production. This is achieved by integration of the transgene into the genome of the host cell. However, creation of recombinant cell lines by conventional means is a costly and inefficient process due to the unpredictability of transgene expression among the recombinant host cells. The unpredictability stems from the high likelihood that the transgene will become inactive due to gene silencing (McBurney et al., 2002). Using conventional technologies, the proportion of recombinant host cells that produce one polypeptide at high levels ranges from 1 to 2%. In order to construct a cell line that produces two polypeptides at high levels, the two transgenes are generally integrated independently. If the two transgenes are transfected simultaneously on two separate plasmids, the proportion of cells that will produce both polypeptides at high levels will be the arithmetic product of the proportions for single transgenes. Therefore, the proportion of such recombinant cell lines ranges from one in 2,500 to one in 10,000. For multimeric proteins with three or more subunits, the proportions decline further. These high-producing cell lines must subsequently be identified and isolated from the rest of the population. The methods required to screen for these rare high-expressing cell lines are time consuming and expensive.

An alternative to simultaneous transfection of two transgene-bearing plasmids is sequential transfection. In this case, the proportion of high-yielding clones will be the sum of the proportions for single transgenes, i.e., 2 to 4%. Sequential transfection, however, has (major) drawbacks, including high costs and poor stability. The high costs result from various factors; in particular, the time and resources required for screening for high-expressing cell lines is doubled, since high expression of each subunit must be screened for separately. The poor overall stability of host cells expressing two polypeptides is a consequence of the inherent instability of each of the two transgenes.

(2) Silencing of transgene expression during prolonged host cell cultivation is a commonly observed phenomenon. In vertebrate cells, it can be caused by formation of heterochromatin at the transgene locus, which prevents transcription of the transgene. Transgene silencing is stochastic; it can occur shortly after integration of the transgene into the genome or only after a number of cell divisions. This results in heterogeneous cell populations after prolonged cultivation, in which some cells continue to express high levels of recombinant protein, while others express low or undetectable levels of the protein (Martin and Whitelaw, 1996; McBurney et al., 2002). A cell line that is used for heterologous protein production is derived from a single cell, yet is often scaled up to, and maintained for long periods at, cell densities in excess of ten million cells per milliliter in cultivators of 1,000 liters or more. These large cell populations (1014 to 1016 cells) are prone to serious declines in productivity due to transgene silencing (Migliaccio et al., 2000; Strutzenberger et al., 1999).

The instability of expression of recombinant host cells is particularly severe when transgene copy numbers are amplified in an attempt to increase yields. Transgene amplification is achieved by including a selectable marker gene, such as dihydrofolate reductase (DHFR), with the transgene during integration (Kaufman, 2000). Increased concentrations of the selection agent (in the case of DHFR, the drug methotrexate) select for cells that have amplified the number of DHFR genes in the chromosome (Kaufman and Sharp, 1982). Since the transgene and DHFR are co-localized in the chromosome, the transgene copy number increases too. This is correlated with an increase in the yield of the heterologous protein (Kaufman, 1990). However, the tandem repeats of transgenes that result from amplification are highly susceptible to silencing (Garrick et al., 1998; Kaufman, 1990; McBurney et al., 2002).

The above-stated problems associated with conventional transgene expression technologies for protein production clearly demonstrate a need in the art for systems that overcomes these problems. Specifically, there is a need for expression systems that i) provide high predictability of expression, allowing balanced expression of multiple chains, ii) provide high yields, iii) provide stability during an extended period during which the protein needs to be produced in large quantities, and iv) result in an increased number of clones with appropriate expression levels.

SUMMARY OF THE INVENTION

In one aspect, the invention provides means and methods for improving characteristics of protein production in a cell. It has, among other things, been found that chromatin modification systems for rendering chromatin more accessible for transcription have a pronounced effect on expression characteristics of protein expression when allowed to act thereon. In one embodiment, the invention, therefore, provides a method for providing a cell with a protein expression unit comprising providing a nucleic acid comprising the unit with a nucleic acid encoding a binding site for a member of a chromatin modification system for rendering chromatin more accessible for transcription (opener), wherein the opener is present in the cell, the method further comprising providing the expression unit to the cell and culturing the cell to allow expression of the protein expression unit.

Histone modification systems have been shown to encompass proteins capable of rendering chromatin more accessible for transcription. An opener of the invention is, therefore, preferably a histone modification enzyme, preferably capable of modifying an N-terminal histone tail. Histone modification plays an important role in both chromatin-associated repression and chromatin-associated activation of gene expression. For instance, acetylation of specific lysines in histone H3 and H4 tails is an important parameter. Normally, histones are very basic proteins that bind tightly to the acid DNA strands. Addition of an acetyl group to the histone tails converts the basic histones into more neutrally charged proteins. This results in a less tight interaction between the basic histones and the acid DNA strands. Acetylation is, therefore, associated with making the chromatin more open or accessible for transcription factors. Histone acetyltransferases (HATs) that add acetyl groups to the histone tails are, therefore, preferred openers of the present invention. Preferred embodiments of HAT openers are p300/CBP, P/CAF (Yang et al., 1996), and/or CBP (Bannister and Kouzarides, 1996) or a functional part, derivative and/or analogue thereof. However, even today, more HAT proteins comprising similar function are identified. Such HAT proteins are, of course, also part of the invention. HAT proteins are likely to act in the context of a multi-protein complex at least in part to allow for specificity of action to certain regions of the chromatin. The Trithorax group (TrxG) protein trithorax (trx) is part of a complex that is involved in keeping genes in the activated state. It is, therefore, not surprising that the multiprotein complex of which the trx protein is part, also contains a HAT protein (Petruk et al., 2001).

Opposing the action of HAT proteins are histone deacetyltransferases (HDACs) (Taunton et al., 1996) that remove acetyl groups from histone H3 and H4 tails. This makes the histones more basic, which results in tightening the interactions between the histones and the acid DNA strands. Hence HDACs are negative regulators of gene expression. Polycomb group (PcG) proteins are associated with HDACs and the repression executed by PcG proteins is, in part, mediated through histone deacetylation (Van der Vlag and Otte, 1999). The opposing activating and repressing roles of, respectively, TrxG and PcG proteins is thus reflected in the association of HAT and HDAC proteins to, respectively, TrxG and PcG proteins.

In addition, specific methylated histone tails have activity in opening chromatin according to the invention. Some types of methylation are associated with rendering chromatin more accessible for transcription, whereas other types of methylation are associated with rendering chromatin less accessible. Methylation of lysine K9 and K27 of histone H3 hallmarks repressed states of chromatin. When H3 K9 is methylated, a docking place for the chromatin-associated repressor protein HP1 protein (heterochromatin protein 1) is created (Bannister et al., 2001; Lachner et al., 2001). When H3 K27 is methylated, a docking place for the chromatin/associated repressor protein Polycomb (Pc) is created (J. Muller, C. M. Hart, N. J. Francis, M. L. Vargas, A. Sengupta, B. Wild, E. L. Miller, M. B. O'Connor, R. E. Kingston, J. A. Simon: Histone methyltransferase activity of a *Drosophila* Polycomb group repressor complex. *Cell* 2002, 111:197-208.)

In contrast, the Ash1 protein (Nakamura et al., 2000) is a trithorax group protein that acts as a positive regulator of gene expression. Ash1 has methyltransferase activity and adds a methyl group to at least lysine K4 of histone H3 (Beisel et al., 2002). A methyltransferase capable of adding a methyl group to at least lysine K4 of histone H3 is thus a preferred opener of the invention. Preferably, the opener comprises Ash1 protein or a functional part, derivative and/or analogue thereof.

The opposing actions of the activating Trithorax group and repressing Polycomb group proteins can at least in part be explained by, respectively, histone acetylation versus histone deacetylation, but also in part by their differential abilities to methylate specific and distinct lysines in histone tails. Methylation of specific lysines in histone tails is often either preceded or prevented by deacetylation of the same lysines, thereby creating a complex and hierarchical interplay between histone modifications. Besides the acetylation and methylation of histone tails, phosphate groups and ubiquitin groups can also be added. These events can influence the order in which either acetylation or methylation of histone tails can take place. Collectively, this complex interplay between histone modifications is referred to as the "histone code" that is considered as the most fundamental mechanistic explanation for both repressing and activating epigenetic gene regulation mechanisms. It is thus, according to the invention, entirely possible that among the histone phosphorylating or ubiquinating enzymes, there are those that can render chromatin more accessible to transcription.

The different histone methyltransferases have a structural protein motif, the SET domain in common. The SET domain (for Su(var)39, E(z) and trx, the three proteins in which the domain was first identified) is essential for histone methyltransferase activity to take place. It follows that targeting an activating histone methyltransferase or its functional part, the SET domain can have a beneficial effect on gene expression by interfering at the level of chromatin structure.

Another preferred group of openers are comprised in the chromatin-remodeling proteins such as Tritorax group proteins, CHRAC proteins, ACF group proteins, and/or a NURF group protein. Polycomb group (PcG) mediated silencing is counteracted by gene-activating Trithorax group (TrxG) proteins. This has been established genetically in the fruit fly *Drosophila* where mutations in PcG and TrxG counteract each other (Kennison and Tamkun, 1992). In addition, in other model systems including man, PcG and TrxG complexes have been identified (Kingston et al., 1996). Specific TrxG proteins are trithorax (Mazo et al., 1990; Petruk et al., 2001), trithorax-like (Farkas et al., 1994), Brahma (Tamkum et al., 1992), ISWI (Elfring et al., 1994), Ash1 (Nakamura et al., 2000; Beisel et al., 2002), moira (Crosby et al., 1999), and osa (Treisman et al., 1997).

One TrxG protein is Brahma (Tamkun et al., 1992; Chiba et al., 1994; Kal et al., 2000; Sif et al., 2001; Mizutani, 2002). This protein is part of a multimeric protein complex that operates as a so-called chromatin-remodeling complex. Chromatin-remodeling has been defined as the ATPase-dependent disruption of nucleosomes to facilitate binding of transcription factors to the chromatin (Kwon et al., 1994; Imbalzano et al., 1994; Quinn et al., 1996). The chromatin becomes more open or accessible for transcription factors and thus transcription. Other chromatin-remodeling complexes have been defined, such as CHRAC (Varga-Weisz et al., 1997) and NURF (Tsukiyama and Wu, 1995). A more comprehensive overview is given by Fyodorov and Kadonaga, 2001. In addition, these complexes operate in an ATPase-dependent fashion. Thus, in this embodiment, the opener preferably comprises a chromatin-remodeling protein and preferably the Trithorax group protein Brahma, a CHRAC group protein, a NURF group protein, ACF group proteins (for ATP-utilizing chromatin assembly and remodeling factor) (Ito et al., 1997), or a functional part, derivative and/or analogue thereof. Purified ACF fractions contain Imitation SWI (ISWI) protein (Elfring et al., 1994). Three other proteins co-purify with this complex termed p47, p170 and p185 referring to their apparent molecular weight. In a preferred embodiment, the chromatin-remodeling protein comprises an ISWI protein or a Brahma protein or a functional part, derivative and/or analogue thereof.

Trithorax group proteins have miscellaneous effects on chromatin; however, at least some proteins of the group are capable of rendering chromatin more accessible to transcription factors. Thus, in a preferred embodiment, the opener comprises a protein of the trithorax group and preferably comprises an ISWI protein or a trithorax protein, a trithorax-like protein, a Brahma protein, an Ash protein, a moira protein, an osa protein, or a functional part, derivative and/or analogue thereof.

A functional part, derivative and/or analogue of an opener of the invention comprises the same activity in kind, not necessarily in amount, as an opener mentioned, this activity being a sequence-specific nucleic acid binding activity specific for the binding site and a chromatin modification activity rendering chromatin more accessible for transcription. This chromatin modification activity may be intrinsic to the opener or may be present through enabling a further protein to act on the chromatin. Suitable parts may be generated by mutation, deletion and/or insertions of the opener. These may be tested in a method of the invention for functionality as an opener. Often, parts of a protein can be identified that can be manipulated, at least to some extent, without affecting the kind of function of the protein. Such openers comprising such modifications are, of course, within the present invention. For openers that comprise the so-called SET domain, the functional part typically comprises this SET domain. Derivatives may be generated by, for instance, conservative amino acid substitutions. These typically retain the same function in kind. Analogues of openers of the present invention are typically proteins having the same or similar chromatin modification activity in kind, not necessarily in amount. Suitable analogues may be found in other than the mentioned species. Such analogues can, for instance, be selected by amino acid and/or nucleic acid homology. For instance, ISWI2 has, in humans, the homologues BRG1 and hbrm. ISWI2 is homologues to Brahma, whereas BAF170 and BAF155 are SWI3 homologues. Other non-limiting examples of suitable homologues are BAF170, BAF155 and SWI3, which are homologues of moira. Such homologues may be used with the invention.

BRIEF DESCRIPTION OF THE SEVERAL VIEWS OF THE DRAWINGS

FIG. 1 is a schematic diagram of the invention.

FIG. 1A shows two expression units on one plasmid. Expression unit one comprises a bicistronic gene containing (from 5' to 3') a transgene (encoding, for example, one subunit of a multimeric protein; Gene 1), an IRES, and a selectable marker (zeo, conferring zeocin resistance) under control of the CMV promoter. Upstream of the CMV promoter are four LexA binding sites (LexA-BS). The expression unit has the SV40 transcriptional terminator at its 3' end (t). Next is a monocistronic gene encoding a fusion protein between the LexA protein and either (i) a histone acetyltransferase (HAT) or a functional part of a HAT that is still able to transfer acetyl groups to histone tails (LexA-HAT), (ii) a histone methyltransferase (HMTase) or a functional part (SET domain) of an HMTase that is still able to transfer methyl groups to at least lysine K4 of the histone H3 tail or (iii) the trithorax group protein Brahma. These genes are under control of the SV40 promoter. The expression unit has the SV40 transcriptional terminator at its 3' end (t). The entire cassette with the two expression units is flanked by STAR elements.

FIG. 1B is similar to FIG. 1A, but there are now three expression units on one plasmid. Expression unit one comprises a bicistronic gene containing a transgene Gene 1, an IRES, and a selectable marker zeo under control of the CMV promoter. The transcription orientation of this first expression unit is directed upstream. Expression unit two comprises a bicistronic gene containing a transgene Gene 2, an IRES, and a selectable marker puro (puromycin-resistance gene) under control of the CMV promoter. The transcription orientation of this first expression unit is directed downstream. Between the two CMV promoters of the two expression units are four LexA binding sites (LexA-BS). The monocistronic gene encodes the same LexA fusion proteins as in FIG. 1A. The entire constellation of three expression units is flanked by STAR elements.

Construct two comprises a first expression unit comprising a bicistronic gene containing (from 5' to 3') the d2EGFP reporter gene, an IRES, and a selectable marker (zeo, conferring zeocin resistance) under control of the CMV promoter. The cassette has the SV40 transcriptional terminator at its 3' end (t). Upstream of the CMV promoter are four LexA binding sites (LexA-BS). Downstream of the LexA binding sites is a second expression unit, a monocistronic gene encoding a fusion protein between the LexA protein and the functional P300 histone acetyltransferase (HAT) domain. The expression unit has the SV40 transcriptional terminator at its 3' end (t). Transcription of both expression units is directed opposite. Hence, the LexA binding sites are placed between and will act upon both expression units (CMV-p300HAT).

An indicated number of stable colonies are expanded and after different indicated time periods, the d2EGFP signal is determined on an XL-MCL Beckman Coulter flow cytometer. For each independent colony, the mean of the d2EGFP signal is plotted. This is taken as the measurement for the level of d2EGFP expression. The results are compared to colonies that are transfected with a construct containing no LexA-P300HAT gene (CMV-Control).

Figure 7:
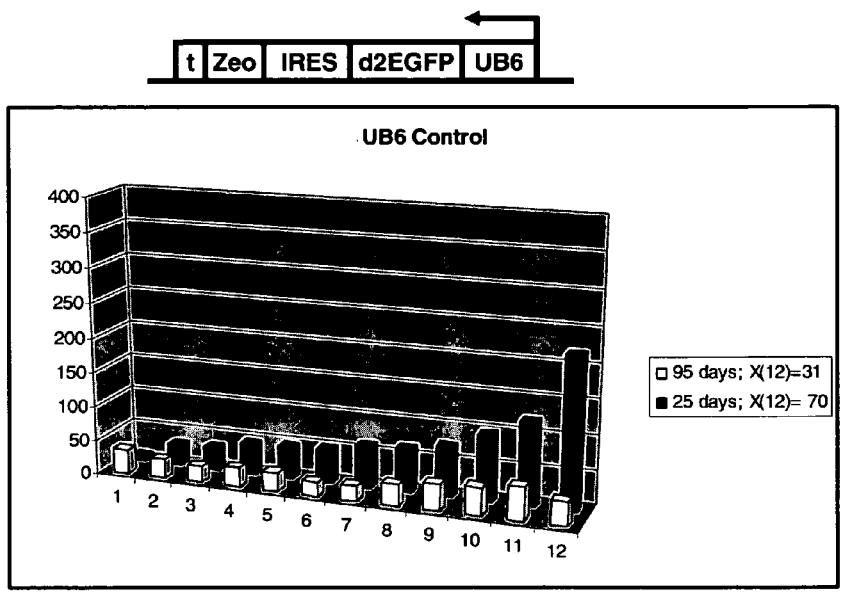
Figure 7:
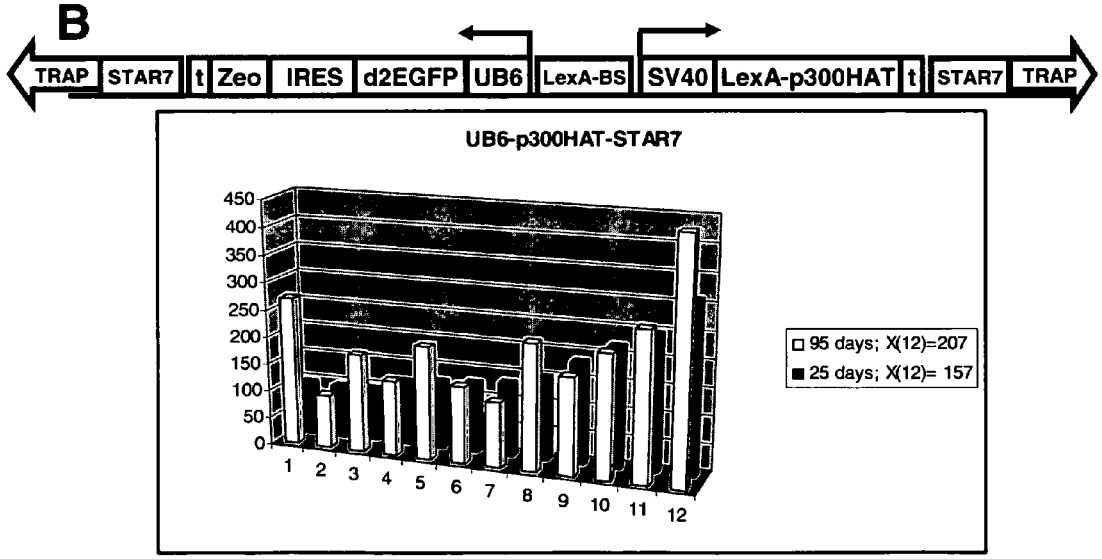

FIG. 7. The increased gene expression levels due to the combined action of STAR7/TRAP and the p300 HAT opener is highly stable over time. Two different constructs are transfected to CHO-K1 cells. Construct one comprises a bicistronic gene containing (from 5' to 3') the d2EGFP reporter gene, an IRES, and a selectable marker (zeo, conferring zeocin resistance) under control of the UB6 promoter (UB6 Control).

Construct two comprises a first expression unit comprising a bicistronic gene containing (from 5' to 3') the d2EGFP reporter gene, an IRES, and a selectable marker (zeo, conferring zeocin resistance) under control of the UB6 promoter. The cassette has the SV40 transcriptional terminator at its 3' end (t). Upstream of the CMV promoter are four LexA binding sites (LexA-BS). Downstream of the LexA binding sites is a second expression unit, a monocistronic gene encoding a fusion protein between the LexA protein and the functional P300 histone acetyltransferase (HAT) domain. The expression unit has the SV40 transcriptional terminator at its 3' end (t). Transcription of both expression units is directed opposite. Hence, the LexA binding sites are placed between and will act upon both expression units. The entire cassette is flanked with STAR7 elements (STAR7) at both the 5' and 3' end (UB6-p300HAT-STAR7). To the STAR7 sequence a SPA-pause TRAP sequence is added.

An indicated number of stable colonies are expanded and after different indicated time periods, the d2EGFP signal is determined on an XL-MCL Beckman Coulter flow cytometer. For each independent colony, the mean of the d2EGFP signal is plotted. This is taken as the measurement for the level of d2EGFP expression. The results are compared to colonies that are transfected with a construct containing no LexA-P300HAT gene (UB6-Control).

Figure 8:
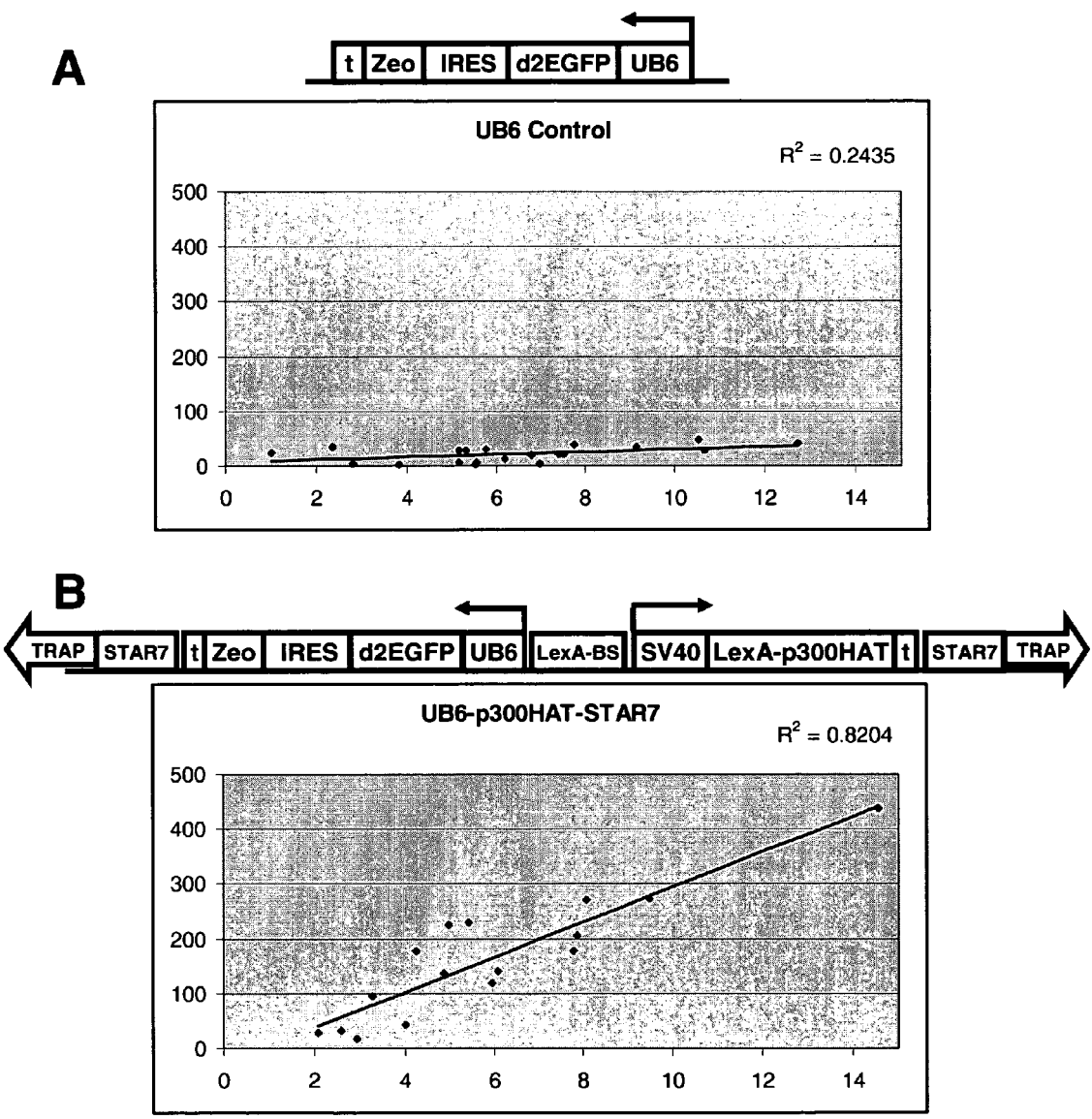

FIG. 8. The combination of the p300 HAT opener and a STAR/TRAP element improves copy number dependency of gene expression. d2EGFP expression units in UB6 Control (A) and UB6-p300HAT-STAR7 (B), integrated into CHO genomic DNA are analyzed for d2EGFP expression and the presence of the number of d2EGFP copies. Radioactive d2EGFP DNA probe was used to detect the amount of transgene DNA in the genome of each clone, which was then quantified with a phosphorimager. The expression of the clones are plotted against the relative copy number. The correlation coefficient is indicated in each case.

Instead of LexA-Opener fusion proteins that targeted to LexA binding sites, GAL4-Opener fusion proteins can also be used. These GAL4-Opener fusion proteins are targeted to GAL4 binding sites, which are placed upstream of a promoter. Unlike the bacterial LexA protein, GAL4 is a yeast protein. Like LexA protein, GAL4 is a transcription factor that has a DNA binding domain and a trans-acting domain, the last domain being responsible for activation of gene expression. To create a GAL4-Opener fusion protein, the part of the GAL4 gene encoding amino acids 1 to 147 (Lillie and Green, 1989) is cloned in frame with the respective Opener protein or functional part of the Opener protein. In the current invention, expression of the GAL4-Opener fusion gene is driven by the SV40 promoter. The GAL4-Opener fusion protein is targeted to GAL4 binding sites, called GAL4 operators. Commonly, four GAL4 operators are placed immediately upstream of a promoter. One GAL4 operator is the following sequence: CGGAGTACTGTCCTCCG (SEQ ID NO:14 of the accompanying and incorporated herein SEQUENCE LISTING).

DETAILED DESCRIPTION OF THE INVENTION

Many different proteins can act as openers in the invention. The opener may act directly on the accessibility of chromatin or indirectly via the association with a complex present in the cell, wherein the complex is instrumental in the accessibility of the chromatin. One component of an opener of the invention is the sequence-specific association thereof with the binding site on the nucleic acid comprising the protein expression unit. The binding site may be a normal binding site for an opener. Alternatively, a binding specificity for the binding site is provided to an otherwise operable opener. In yet another embodiment, a sequence-specific nucleic acid binding specificity for the binding site is provided to a protein, thereby resulting in an opener of the present invention. It is possible that proteins, when provided with a binding specificity for the binding site, do not have a sequence-specific binding specificity by themselves (i.e., prior to being provided with such specificity). Such proteins (further termed pre-openers) can be provided to the cell to achieve a generalized effect on chromatin re-modeling. This is another aspect of the present invention. The invention thus provides a cell comprising a protein expression unit, wherein the cell is provided with a pre-opener of the present invention. Such cells can, through the generalized effect on chromatin re-modeling, display favorable expression characteristics. This can, for instance, be due to a shift in the balance between activating and repressing complexes.

An opener may be expressed by the cell prior to providing the cell with the protein expression construct, for instance, in case the cell naturally expresses the opener. Alternatively, the opener may be provided to the cell, for instance, as a nucleic acid encoding the opener. When openers are used that have been provided with a specific nucleic acid binding activity toward the binding site, it is often appropriate to provide the cell with the opener. However, cell lines may be created already expressing such opener. Such cell lines can then subsequently be used to introduce protein expression units of the invention at will. Cell lines provided with a nucleic acid comprising an opener provided with a new sequence-specific binding activity are, therefore, also part of the invention. Such cell lines must, of course, carry the nucleic acid in stable form, thus, preferably integrated into the genome of the cell. In a preferred embodiment, such cell lines are used for the collection of proteins produced through a means or a method of the invention. Preferred openers for such cell lines comprise HAT proteins provided with a new sequence-specific binding activity. Preferably, HAT proteins comprise p300/CBP protein, a P/CAF protein, and/or a CBP protein or a functional part, derivative and/or analogue thereof. The new sequence-specific binding activity preferably comprises a nucleic acid binding domain of a sequence-specific DNA binding protein. Non-limiting examples are the GAL4 or the LexA DNA binding domains. However, many other sequence-specific binding proteins can be used. A person skilled in the art can use DNA binding domains of a large number of different proteins and generate an opener of the invention. The mentioned person may take the many examples of fusions of DNA binding domains to other functional proteins as guidance. It is, for instance, entirely possible to modify to hybrid systems such that upon association of the two parts of the hybrid system, an opener of the present invention is generated. In a preferred embodiment, the opener is a fusion protein comprising at least a functional part of a mentioned opener and a sequence-specific nucleic acid binding domain. Preferably, the opener comprises at least a functional part of a histone acetyltransferase, a histone methyltransferase or a chromatin-remodeling protein. Preferably, the histone acetyltransferase comprises a p300/CBP protein, a P/CAF protein, or a CBP protein, or a functional part, derivative and/or analogue thereof. Preferably, the histone methyltransferase comprises an Ash1 protein or a functional part, derivative and/or analogue thereof. The chromatin-remodeling protein preferably comprises a trithorax group protein, a CHRAC group protein, a NURF group protein, ACF group proteins, or a functional part, derivative and/or analogue thereof. The mentioned openers may be fused to the DNA-specific binding domain of a zinc-finger protein, a bacterial DNA binding protein, or a yeast or fungus DNA binding protein. Preferably, the DNA binding protein is LexA or Gal4, or functional part, derivative and/or analogue thereof. Because openers or pre-openers have important activity in a cell, it is important not to express too much of these proteins in the cell lines mentioned as this can have toxic effects. This toxic effect is significantly less in cases where a pre-opener has been converted into an opener by providing it with a sequence-specific binding activity. This localizes the effects somewhat, although titration effects may also still occur in this situation. Dosed expression is, therefore, also of importance for cell lines provided with an expression unit for an (pre-) opener provided with a sequence-specific binding activity. The DNA binding domain is typically added to the N-terminal or the C-terminal end of a protein of the invention. On occasion, one of these fusions may not be functional; however, typically at least one of such chimera retains both properties of the fusion partners (domains). In case a fusion is intended with a protein comprising a SET domain, it is sometimes better to fuse the DNA binding domain at the side of the chain that is the furthest away from the SET domain. However, this is not a general rule.

Protein expression units may be provided with desirable features to implement certain desired functionality. For instance, enhancers, introns, suitable untranslated regions, etc., may be used. Inducible promoters or constitutive promoters may be used. Thus, the present invention further provides a method, wherein the expression unit for the protein of interest and/or an expression unit expressing an opener of the invention is provided with an additional transcription/translation regulating and/or stimulating sequence. A method of the invention provides a high predictable expression. It also provides a high expression level. Moreover, it also provides stable expression levels. In transfections of protein expression units, it further provides more different integration events that (i) express the protein of interest at a high level and results in (ii) a higher number of colonies that have expression of the protein of interest and (iii) in more colonies that have a suitable expression level for protein production. Both properties, of course, are compared to transfection with the same expression unit in the absence of the binding site for a member of a chromatin modification system of the invention. In a particularly preferred embodiment, a protein expression unit is provided with a locus control region or a part thereof. Examples of such sequences may be found in sequences from the α or β globin locus as described U.S. Pat. No. 5,610,053 and PCT International Patent Publication WO 96/04390, or the Igf2-locus. Of course, so-called UCOE sequences as described in WO 00/05393 and WO 02/24930 may also be used. In a preferred embodiment, a nucleic acid of the invention further comprises a so-called STabilizing and Anti-Repressor sequence, also termed STAR sequence. Examples of suitable STAR sequences are given in Table 1. Other STAR sequences can be obtained from PCT/NL02/00390 filed in the name of Chromagenics B.V, which is incorporated by reference herein. This filing also contains methods for finding other STAR sequences. Such other STAR sequences are, of course, also capable of being used in the present invention. STAR sequences can confer upon a linked expression cassette improved transcription capabilities including, but not limited to, at least partial protection from repression-stimulating influences of DNA adjacent to integrated foreign nucleic acid. Placement of the signal sequences and elements on the nucleic acid to be transfected depends on the particular signal or element. A STAR sequence is preferably placed outside of an expression cassette. Preferably, an expression cassette is flanked by at least two STAR sequences. A STAR sequence, at least in part, improves the predictability of expression of a transferred nucleic acid leading to a larger proportion of cells having a suitable expression pattern. This is especially so for embodiments wherein two or more expression cassettes are transferred of which expression is desired. The presence of a STAR sequence, preferably on each of the thus transferred cassettes, improves the number of cells selected with a method of the invention.

As previously mentioned, an increase in the number of cells with appropriate expression patterns is very important in the selection of production cells for clinical grade polypeptides. Thus, in one embodiment of the invention, the protein expression unit comprising the nucleic acid binding site for the opener is flanked on one or both sides by a nucleic acid comprising a STabilizing Anti-Repressor ("STAR") sequence. The binding site for the opener is, of course, preferably placed together with the transcription unit on the side of the STAR sequence. A STAR element further improves stability, levels and predictability of expression of the protein expression unit. It further significantly increases the number of clones expressing a high amount of protein. Without being bound by theory, it is believed that STAR elements create so-called nucleic acid domains of common regulation, if only to prevent the action of transcription repressors located outside the domain from influencing the domain. By placing a binding site for an opener present in the cell in the domain, that domain is preferentially opened and actively maintained in an open state. Optimal results are obtained when the binding site is operably linked to a promoter present in the expression unit.

By "operably linked" is meant that a bound opener is capable of affecting accessibility of the chromatin comprising the promoter. Preferably, the binding site is provided to the expression unit upstream of a promoter therein. Typically, though not necessarily, good results are obtained when the binding site is within ten bases from the promoter, together with promoter-associated factor binding sites, preferably, upstream of the promoter. It is, of course, possible to introduce further binding sites for openers in, or in the vicinity of, the protein expression unit. Such additional binding sites may further improve expression characteristics. All mentioned advantages of the invention are, of course, compared to the same protein expression unit but lacking either the binding site and/or the additional element such as the STAR sequence.

A further aspect of the invention is the combination in the protein expression unit of an opener in the context of the invention with a TRAnscription Pause (TRAP) sequence. This combination further improves the predictability of expression of the protein of interest. The invention uses the mentioned combination to enhance a protein expression characteristic of a protein expression unit. It is thought that a TRAP, at least in part, prevents the formation of antisense RNA or, at least in part, prevents transcription to enter the protein expression unit. TRAP sequences are described in PCT/NL03/00850 filed in the name of Chromagenics and this reference is, therefore, incorporated by reference herein for definition of TRAP sequences and for methods for providing protein expression units with TRAP sequences. Usually, DNA sequences such as the SV40 polyadenylation signal are used to terminate transcription by placing the SV40 polyadenylation signal immediately downstream of a gene that is expressed. In other words, transcription should be prevented from continuing downstream of the gene. In the present invention, transcription blockers (TRAP) are preferably placed, both upstream and downstream of the expression unit, in such a manner that they prevent transcription to enter an open reading frame (when the TRAP is downstream thereof) or to enter the combination of the promoter and open reading frame driven by it (when located upstream of the open reading frame). The orientation of TRAP when placed downstream is opposite of the usual orientation of the SV40 polyadenylation signals that are placed downstream of genes. The orientation of an upstream TRAP is in the same orientation as the SV40 polyadenylation signals that are placed downstream of the genes.

In one embodiment, a method of the invention further comprises providing the cell with at least one protein expression unit which unit comprises a promoter functionally linked to an open reading frame encoding at least one protein of interest, characterized in that the protein expression unit further comprises at least one TRAnscription Pause (TRAP) sequence and wherein the TRAP sequence is functionally located downstream of the open reading frame and at least in part prevents formation of antisense RNA. Preferably, at least one TRAP sequence is in a 3'-5' orientation (in relation to the coding region).

Preferably, the TRAP sequence reduces the formation of antisense RNA to a non-detectable level. Due to the presence of the TRAP, the formation of antisense RNA is at least in part prevented and hence, the amount of dsRNA is decreased. As a consequence, the level of small dsRNAs of 21 to 23 base pairs (RNAi) is also decreased and the corresponding (full-length) RNA encoding a protein of interest will not be degraded. Hence, translation of the corresponding RNA results in (increased) expression of a protein of interest.

Surprisingly, as disclosed herein, the use of TRAP sequences further improves stability of expression of the protein of interest in the protein expression unit.

In the above-outlined embodiment, the TRAP sequence can, for example, be a terminator and/or a polyadenylation signal sequence, but in an orientation which differs from a possibly used terminator sequence behind an open reading frame in the protein expression unit. However, it is entirely possible that there are TRAP sequences that are bi-directional. These may also be used in the present invention to, at least in part, prevent transcription from entering a transcription unit.

Further provided is the use of a TRAP to strengthen "inertness" of the transcription units, for instance, when the CMV-driven transcription in the units of FIG. 1A are also prevented from escaping the transcription unit. Normally, the SV40 transcriptional terminator is used for this purpose. This terminator does not, however, stop transcription completely. Hence, a further TRAP sequence is incorporated upstream of the 3' STAR element in the expression cassette (FIG. 2C). This TRAP sequence is placed in a 5'-3' orientation in order to stop transcription that might leak through the SV40 transcriptional terminator. In this configuration, the entire expression cassette has become essentially inert for transcription leaking in, as well as leaking out.

Thus, in another embodiment, the invention provides the use of a TRAP sequence to, at least in part, isolate a genetic element from transcription proceeding into the element. In a preferred embodiment, the genetic element is a STAR element. Thus, the invention further provides a STAR element together with a TRAP sequence of the invention, preferably, a STAR element flanked by at least two STAR elements on either side. The orientation of the TRAP element in these embodiments is such that transcription proceeding from outside the STAR element into the STAR element is at least in part prevented. This embodiment is in particular relevant if there were to be inverted repeats present in the STAR element. These inverted repeats can initiate the formation of dsRNA. This in turn would lead to gene silencing of adjacent genes. Thus, this specific configuration of TRAP-STAR-TRAP elements cannot only prevent formation of dsRNA in the genetic element, i.e., the STAR element, it also provides further protection of the entire expression unit.

In another embodiment, the invention provides a method for expression of (or producing) at least one protein of interest in a cell comprising providing the cell with at least one protein expression unit which unit comprises a promoter functionally linked to an open reading frame encoding at least one protein of interest, characterized in that the protein expression unit further comprises at least one TRAP sequence and wherein the TRAP sequence is located upstream of the promoter and at least in part prevents transcription to enter the protein expression unit. Preferably, at least one TRAP sequence is in a 5'-3' orientation (in relation to the coding region).

Again, a TRAP sequence used in the latter embodiment can be a terminator and/or a polyadenylation signal sequence, but this time the TRAP sequence is in an unusual position with regard to the open reading frame because the TRAP is located upstream of the promoter that drives expression of the open reading frame.

In this embodiment, the presence of a TRAP sequence at least in part prevents transcription from a promoter sequence located outside a protein expression unit. Hence, the RNA from the protein expression unit does not have to compete with other RNA and hence, a more efficient protein production system is provided.

The use of a TRAP to, at least in part, prevent formation of antisense RNA or to, at least in part, prevent transcription to enter the protein expression unit isolates the protein expression unit from negative effects, like formation of RNAi, from outside the unit.

A TRAP sequence is herein functionally defined as a sequence capable of, at least in part, preventing formation of antisense RNA or to, at least in part, prevent transcription to enter the protein expression unit. In other words, a TRAP sequence, when placed into a transcription unit, results in a reduced level of transcription of the nucleic acid present on the 3'-side of the TRAP when compared to the level of transcription observed in the nucleic acid on the 5'-side of the TRAP. When in this application no particular reference is made toward the orientation of the TRAP in a particular construct, it is in the orientation that it blocks transcription from entering a (potential) transcription unit, i.e., the transcription unit of the nucleic acid of interest. Preferably, the TRAP sequence is physically linked to the protein expression unit that it aims to transcriptionally isolate from any flanking transcription units, at least prior to transfecting the unit into the genome of the cell. Upon integration of the unit, the unit and elements linked thereto become linked to sequences in the genome and the element present therein and, in the case of concatemer integration, the integrated unit can become linked to co-integrated units or other transfected nucleic acid. In these embodiments, a TRAP can be present upstream or downstream of the transcription unit it aims to isolate. When it is present upstream, the orientation of the TRAP is such that it can, at least in part, reduce transcription originating upstream of the transcription unit and the TRAP and proceeding toward the transcription unit. When it is present downstream of the transcription unit, the TRAP is, in these embodiments, in an orientation that it, at least in part, reduces transcription origination downstream from the transcription unit that it is linked to and proceeding toward the transcription unit. The orientations upstream or downstream are typically mirror images of each other. However, as mentioned above, in the situation where concatmers are formed upon integration of a protein expression unit in the genome, it is also possible to prevent transcription from entering a flanking co-integrated transcription unit by placement of a TRAP sequence downstream of the protein expression unit in the orientation that it reduces transcription initiating within the protein expression unit. In this embodiment, the TRAP is, prior to integration, physically linked to the transcription unit of which transcription can enter a flanking transcription unit. Through the linkage of the TRAP to the unit prior to integration, this potential is, at least in part, reduced. This TRAP sequence is, in addition to normal the transcription termination and/or a polyadenylation signal present, a protein expression unit. With respect to the placing of a TRAP in relation to the protein expression unit it intends to protect from incoming transcription, it is understood that the TRAP is preferably placed close to the expression cassette that it intends to transcriptionally isolate. In other words, it is preferred that there are no potentially active promoter elements firing into the protein coding domain between the TRAP and the protein coding domain of the expression unit it intends to transcriptionally isolate, other than the promoter designed to direct transcription in the transcription unit (i.e., to drive the protein of interest).

As disclosed herein within the experimental part, a TRAP sequence can, for example, be a polyadenylation site and/or a pausing site, where the RNA polymerase II stalls. A TRAP can be derived from any source, as long as efficient termination of transcription is achieved. In one embodiment, a TRAP is identified based on its ability to, at least in part, prevent formation of antisense RNA or to, at least in part, prevent transcription to enter the protein expression unit. Example 1 provides a method to test the effect of putative TRAPs on transcription. It is shown that STAR elements 7, 17 and 40 are poor in blocking transcription.

On the other hand, certain regions of phage λ, intergenic regions that separate histone H3 genes, as well as a synthetic polyA sequence, fulfill the criteria of a TRAP, since they are all potent blockers of transcription.

In a preferred embodiment, at least one TRAP sequence is located upstream of the promoter and wherein the TRAP sequence is in a 5'-3' orientation. In yet another preferred embodiment, at least one TRAP sequence is located downstream of the open reading frame and wherein the TRAP sequence is in a 3'-5' orientation with respect to the orientation of the open reading frame. It is clear from the examples disclosed herein that the potential of TRAP sequences is orientation-dependent. It is, therefore, clear that the orientation in which a TRAP is applied to flank a transgene can be of importance for its proper functioning. However, it is clear that there are also TRAP sequences which act independent of their orientation.

In a preferred embodiment, the protein expression unit comprises at least two TRAP sequences. A particularly preferred version of at least two TRAP embodiments is the presence of at least one TRAP upstream and at least one TRAP downstream of the transcription unit of interest. Thus, preferably, at least two TRAP sequences are arranged such that the TRAP sequences are flanking the combination formed by the promoter and the open reading frame.

When multiple protein expression units are present on one and the same part of genetic information, it is also possible to at least partly inhibit or block transcription from one protein expression unit into another protein expression unit. In this case, a TRAP sequence is placed between (possibly different) protein expression units, the orientation of this TRAP sequence is, of course, in the 5'-3' orientation with respect to transcription for which the blocking is intended. When two expression cassettes integrate in a convergent manner, transcriptional inert domains can be created by placing TRAP sequences in such a configuration that transcription is prevented to enter the transcription units.

Preferred examples of TRAP sequences are outlined in Table 2. Preferably, the TRAP sequence comprises the lambda 35711-38103 sequence as depicted in Table 2 and/or a functional equivalent and/or a functional fragment thereof. In another preferred embodiment, the TRAP sequence comprises a polyA sequence, preferably a synthetic polyA (SPA) sequence and/or a functional equivalent and/or a functional fragment thereof, for example, a SPA sequence and/or a functional equivalent and/or a functional fragment thereof as depicted in Table 2. In yet another preferred embodiment, the TRAP sequence comprises a combination of an SPA and the human $\alpha 2$ globin gene pause signal and/or a functional equivalent and/or a functional fragment thereof, for example, a combination of an SPA and the human $\alpha 2$ globin gene pause signal and/or a functional equivalent and/or a functional fragment as depicted in Table 2.

A "functional equivalent" and/or a "functional fragment" of a sequence depicted in Table 2 is defined herein as follows. A functional equivalent of a sequence as depicted in Table 2 is a sequence derived with the information given in Table 2. For instance, a sequence that can be derived from a sequence in Table 2 deleting, modifying and/or inserting bases in or from a sequence listed in Table 2, wherein the derived sequence comprises the same activity in kind, not necessarily in amount, of a sequence as depicted in Table 2. A functional equivalent is further a sequence comprising a part from two or more sequences depicted in Table 2. A functional fragment of a sequence in Table 2 can, for example, be obtained by deletions from the 5' end or the 3' end or from inside of the sequences or any combination thereof, wherein the derived sequence comprises the same activity in kind, not necessarily in amount.

Methods of the invention provide improved predictability, levels (yield) and stability of transgene expression. STAR elements increase the predictability, yield and stability of transgene expression even further by keeping chromatin-associated repression "out." Beside protection against chromatin-silencing by means of STAR elements, the present invention in addition creates means and methods to convert the chromatin of a transgene in a more open state, thus further facilitating the predictability, yield and stability of transgenic protein expression. To achieve this goal, chromatin-remodeling proteins, histone acetyltransferase or histone methyltransferase proteins can be targeted to the promoter of the transgene. The invention thus prevents silencing of transgene expression by the combined action of keeping repression out and by simultaneously keeping chromatin in an open state. By combining STAR elements and/or TRAP sequences with chromatin opening factors, the present invention employs two or more different types of DNA elements or proteins that synergistically reinforce each other to create novel (host) cells/cell lines that efficiently and stably express proteins. In a preferred embodiment, openers, STAR elements and TRAP sequences as disclosed herein are combined in expression units. In combination with STAR elements, TRAP sequences potentiate the action of STAR elements. That is, incorporation of the STAR-TRAP combination results in higher expression levels than when STAR or TRAP elements alone are incorporated.

In principle, any type of polypeptide or protein may be produced using a method of the invention. The method is particularly suited for the production of multimeric proteins comprising at least two polypeptides. In a preferred embodiment, a method provides for the expression of at least two polypeptides in a predetermined ratio. Preferably, at least two polypeptides comprise an immunoglobulin heavy chain and an immunoglobulin light chain. According to this embodiment, a multimeric protein, an antibody, is obtained. It is clear to a person skilled in the art that it is possible to provide a cell which expresses an immunoglobulin heavy chain from one protein expression unit and an immunoglobulin light chain from another protein expression unit with a third protein expression unit encoding a secretory component or a joining chain. In this way the production of, for example, sIgA and pentameric IgM is provided. Preferably, the first polypeptide and the second polypeptide comprise at least the variable part of an immunoglobulin light chain and an immunoglobulin heavy chain. Preferably, the first polypeptide comprises at least the variable part of an immunoglobulin heavy chain, whereas the second polypeptide comprises an immunoglobulin light chain or derivative and/or analogue thereof. This embodiment warrants that an increased proportion of the cells selected will display a tendency to slightly overproduce immunoglobulin heavy chain, thereby allowing more efficient production of the multimeric protein. Immunoglobulin technology is very advanced at the present time and it is possible to generate coding domains for antibodies that have no complementary antibody in nature, e.g., a completely artificial antibody. Such antibodies are also within the scope of the present invention. For an overview of relevant technology for antibodies, their selection and production, we refer to H. E. Chad S. M. and Chamow, 2001, Therapeutic antibody expression technology, *Curr. Opin. Biotechn.* 12, 188-194; R. C. Das, 2001, Proteins and antibodies make advances as therapeutic products, *Am. Clin. Lab.* 20, 8-14.

Further provided is the use of a cell of the invention for the production of an antibody or a functional part, derivative and/or analogue thereof. In a particularly preferred embodiment, the antibody produced comprises a human or humanized antibody, whereas the cell wherein the antibody is produced is a human cell or derived therefrom, for instance, by fusion of a human cell to a human cell or a non-human cell. In view of the production of multimeric protein, a method of the invention preferably further comprises providing the cell with a second protein expression unit. Preferably, the expression unit encodes a member of a multimeric protein. Preferably, the protein expression unit encodes an immunoglobulin heavy or light chain or an antigen binding part, derivative and/or analogue thereof.

A method of the invention is particularly suited for the selection of cells for production of clinical grade polypeptides of interest. A method, therefore, preferably, further comprises culturing the cell and harvesting the (multimeric) protein. The invention, therefore, further provides a sample comprising the protein, obtainable by a method of the invention. Preferably, a sample comprises at least the variable part of an immunoglobulin light chain and immunoglobulin heavy chain. Preferably, the protein comprises a human immunoglobulin light chain and a human immunoglobulin heavy chain or immunologically related to a human immunoglobulin chain. Also provided is the use of a sample or antibody of the invention for the preparation of a medicament or a vaccine, such as for the treatment of cancer.

The protein expression unit may be mon-cistronic, bi-cistronic or multicistronic. Preferably, the protein expression unit comprises a multicistronic gene. Units comprising several cistrons can be transcribed as a single mRNA. Translation of the second and further coding regions present on that RNA can be achieved in various ways, including the use of translation reinitiation sites or internal ribosome entry sites, the latter of which is preferred. Advantages of bi- or multi-cistronic units are plurifold and include easy selection of clones expressing a protein of interest, for instance, by placing the nucleic acid encoding a dominant selectable marker protein downstream of nucleic acid encoding a protein or polypeptide of interest.

Any type of promoter may be used in the present invention as long as it is operable for allowing transcription in the protein expression unit at a certain time point, or continuously. Preferred promoters encompass a human cytomegalovirus, a simian virus 40, a ubiquitine C, an elongation factor one-alpha promoter or a functional part, derivative, analogue or combination thereof. Functional part can be generated by deletion or mutation of nucleic acid of the promoter. A derivative is, for instance, a promoter of a different species but homologous to a promoter mentioned above. Such promoters can be found, amongst others, by comparing sequences of the different species. Human cytomegalovirus has a homologue in other species; similarly, simian virus 40 has a homologue in other species. Promoters found in such homologues are also preferred in the present invention. Analogues of such promoters are promoters comprising one or more similar elements found in the mentioned promoters but obtained artificially or from a different promoter. Such elements may comprise a certain transcription initiation region (TATAA box or equivalent, such as the promoter driving hADA.). Further elements are particular enhancing elements placed in the vicinity of the transcription initiation region and the like.

The invention further provides a cell obtainable by a method of the invention. The cell, of course, comprises an expression unit comprising a binding site for an opener of the invention. Preferably, the expression unit is provided with a binding site for the opener. Further provided is a cell provided with a nucleic acid encoding an opener of the invention, preferably, an opener provided with a new DNA binding specificity. Preferably, the cell is a yeast cell, a vertebrate cell or a plant cell, preferably, mammalian cells and of these, preferably a human cell. Of course, methods of the invention may be performed in vitro or in vivo. Preferably, however, a method of the invention is performed in vitro. Preferred cell lines are cell lines used for the production of proteins. Of these, a preferred cell is a U-2 OS osteosarcoma, CHO, 293, HuNS-1 myeloma, WERI-Rb-1 retinoblastoma, BHK, Vero, non-secreting mouse myeloma Sp2/0-Ag 14, non-secreting mouse myeloma NSO, or NCI-H295R adrenal gland carcinoma cell. The invention further provides a nucleic acid comprising a protein expression unit that is provided with a binding site for a member of a chromatin modification system for rendering chromatin more accessible for transcription (opener), preferably, further comprising a STAR sequence. Preferably, the expression unit comprises a human cytomegalovirus, a simian virus 40, an ubiquitine C, an elongation factor one-alpha promoter or a functional part, derivative, analogue or combination thereof.

The invention further comprises the use of an opener for stabilizing expression of an expression unit and the use of an opener for increasing the number of clones expressing a certain amount of protein after genetic modification. Also provided is the use of an opener for increasing transcript levels produced by an expression unit.

In yet another embodiment, the invention provides a method for improving a function of a protein expression unit comprising a STAR element comprising providing the protein expression unit with a binding site for a member of a chromatin modification system for rendering chromatin more accessible for transcription (opener). Also provided is a method for improving a function of a STAR element in a protein expression unit comprising providing the protein expression unit with a binding site for a member of a chromatin modification system for rendering chromatin more accessible for transcription (opener).

The targeting of chromatin openers to a transgene or a promoter of a transgene is used to achieve predictable high yields and stable transcription of a transgene. In the present invention, HAT proteins such as p300, CBP, and/or P/CAF, HMTase proteins such as Ash1 or the Brahma protein or functional relevant parts of these proteins are produced as fusion protein with the LexA protein (FIGS. 1A, 1B) (Bunker and Kingston 1994).

Instead of LexA-Opener fusion proteins that targeted to LexA binding sites, GAL4-Opener fusion proteins can also be used. These GAL4-Opener fusion proteins are targeted to GAL4 binding sites, which are placed upstream of a promoter. Unlike the bacterial LexA protein, GAL4 is a yeast protein. Like LexA protein, GAL4 is a transcription factor that has a DNA binding domain and a trans-acting domain, the last domain being responsible for activation of gene expression. To create a GAL4-Opener fusion protein, the part of the GAL4 gene encoding amino acids 1 to 147 (Lillie and Green, 1989), is cloned in frame with the respective Opener protein or functional part of the Opener protein. In the current invention, expression of the GAL4-Opener fusion gene is driven by the SV40 promoter. The GAL4-Opener fusion protein is targeted to GAL4 binding sites, called GAL4 operators. Commonly, four GAL4 operators are placed immediately upstream of a promoter. One GAL4 operator is the following sequence: CGGAGTACTGTCCTCCG (SEQ ID NO:14).

These fusion proteins are placed under control of an inducible or constitutive promoter such as the SV40 promoter (FIGS. 1A, 1B). The expression unit for these fusion proteins are present on the same plasmid as the expression unit that contains the gene that encodes the protein of interest (Gene 1) (FIG. 1). Gene 1 is placed under control of the CMV promoter. Upstream of the CMV promoter, binding sites are cloned to which the LexA-HAT, LexA-HMTase or LexA-Brahma proteins are targeted (FIG. 1A). Thus, these fusion proteins are targeted to the vicinity of the promoter in order to keep open the chromatin structure of the promoter in order to facilitate the accessibility of the promoter for transcription factors. It is also possible to create one plasmid containing three expression units that encode, respectively, Gene 1, Gene 2 and LexA-HAT, LexA-HMTase or LexA-Brahma (FIG. 1B). The expression units encoding Gene 1 and Gene 2 are oriented divergent in such a manner that the two CMV promoters are adjacent although differently oriented. Between the two promoters, LexA binding sites are placed to which the LexA-fusion protein is targeted. In this manner, chromatin openers are targeted to both expression units.

It will also be clear to a person skilled in the art that it is not essential that the LexA fusion proteins or HAT proteins are expressed from the same plasmid that contains the expression unit with the gene of interest. The LexA fusion proteins or HAT proteins can also be produced from a separate plasmid.

Therefore, the invention provides in one embodiment, a method for obtaining a cell which expresses one or more proteins comprising providing the cell with one or more protein expression units encoding one or more proteins, characterized in that at least one but preferably at least two of the protein expression units comprises at least one chromatin opener and/or one STAR sequence. In a preferred embodiment, Gene 1 and Gene 2 encode the light and heavy chain of a multimeric immunoglobin protein.

The terms "cell"/"host cell" and "cell line"/"host cell line" are, respectively, typically defined as a eukaryotic cell and homogeneous populations thereof that are maintained in cell culture by methods known in the art and that have the ability to express heterologous or homologous proteins. Thus, in the present invention, it is possible to provide an opener to an expression unit present in the cell, for instance, by means of homologous recombination. Other features may also be provided to the expression unit in the cell. It is thus entirely possible to, for instance, activate a coding region present in the cell. For instance, the gene encoding erythropoietin is not normally expressed in a cell. By introducing providing this protein expression unit with a binding site for an opener of the invention, it is possible to obtain expression of the endogenous gene. This will typically also require replacement of the promoter or addition of further promoter elements such as enhancers. In this embodiment, the endogenous gene is, preferably, further provided with a STAR sequence on one side but preferably, on both sides of the endogenous gene. Of course, methods of the invention may also be used to enhance expression of already expressed endogenous genes. Means and methods for the activation or enhanced expression of endogenous genes by means of homologous or targeted recombination are known in the art. The present invention contributes binding sites for openers, STAR elements and, in particular, preferred promoters to this technology.

The term "expression" is typically used to refer to the production of a specific RNA product or products, or a specific protein or proteins, in a cell. In the case of RNA products, it refers to the process of transcription. In the case of protein products, it refers to the processes of transcription, translation and, optionally, post-translational modifications. In the case of secreted proteins, it refers to the processes of transcription, translation, and, optionally, post-translational modification (e.g., glycosylation, disulfide bond formation, etc.), followed by secretion. In the case of multimeric proteins, it includes assembly of the multimeric structure from the polypeptide monomers. The corresponding verbs of the noun "expression" have an analogous meaning as the noun.

A protein or polypeptide is herein defined as being either (i) a product obtained by the processes of transcription and translation and possibly, but not necessarily, the product is part of a multimeric protein (for example, a subunit) and/or (ii) a product obtained by the processes of transcription, translation and post-translational modification. The term "multimer" or "multimeric protein" is typically defined as a protein that comprises two or more, possibly non-identical, polypeptide chains ("monomers"). The different monomers in a multimeric protein can be present in stoichiometrically equal or unequal numbers. In either case, the proportion of the monomers is usually fixed by the functional structure of the multimeric protein.

The term "protein expression unit" is herein defined as a unit capable of providing protein expression and typically comprises a functional promoter, an open reading frame encoding a protein of interest, and a functional terminator, all in operable configuration. A functional promoter is a promoter that is capable of initiating transcription in a particular cell. Thus, this is normally transcriptionally active in the cell that is used to obtain the expression of the protein of interest. With "normally transcriptionally active" is meant that the promoter must be capable of initiating transcription in the cell, which in case of an inducible promoter, may encompass the provision of the inducer for the promoter. Thus, so-called minimal promoters that have been stripped of their associated transcription-initiating nucleic acid sequences are not encompassed in the term "promoter" as used in the present invention in the context of a promoter driving expression of the protein of interest. Examples of such minimal promoters are the SV40 minimal promoter (from Promega pGL3; Accession number U47296) and the LBK-AP minimal promoter (D. Ruezinsky, H. Beckman and T. Kadesch, Modulation of the IgH enhancer's cell type specificity through a genetic switch, *Genes Dev.* 5, 29-37 (1991)).

Preferred promoters for obtaining expression in eukaryotic cells are the CMV promoter, a mammalian EF1-alpha promoter, a mammalian ubiquitin promoter, or an SV40 promoter. A functional terminator is a terminator that is capable of providing transcription termination. One example of a suitable terminator is an SV40 terminator. The term "an open reading frame encoding a protein of interest (or a transgene)" is typically defined as a fragment of DNA that codes for a specific RNA product or products or a specific protein or proteins and is capable of becoming integrated into the genome of a host cell. It includes DNA elements used for proper transcription and translation of the coding region(s) of the transgene. DNA encoding the protein of interest/transgene can either be a DNA encoding a product obtained by the processes of transcription and translation (and possibly, but not necessarily, the product is part of a multimeric protein, for example, a subunit) or a product obtained by the processes of transcription, translation and post-translational modification.

The terms "recombinant cell/host cell" and "recombinant cell line/host cell line" are, respectively, typically defined as a host cell and homogeneous populations thereof into which a transgene has been introduced for the purpose of producing a heterologous protein or proteins.

A STAR (STabilizing Anti-Repressor) sequence (or STAR element; the terms will be used interchangeably herein) is a DNA element that we have first identified in eukaryotic genomes on the basis of their ability to block transgene repression. STAR sequences can be identified (as disclosed, for example, in Example 1 of EP 01202581.3) using a method of detecting and optionally selecting a DNA sequence with a gene transcription-modulating quality. A STAR sequence comprises the capacity to influence transcription of genes in cis and/or provide a stabilizing and/or an enhancing effect. The expression level of the transgene is stable over many cell generations and does not manifest stochastic silencing. Therefore, STAR sequences confer a degree of position-independent expression on transgenes that is not possible with conventional transgenic systems. "Position independence" means that transgenes that are integrated in genomic locations that would result in transgene silencing are, with the protection of STAR elements, maintained in a transcriptionally active state. Moreover, a STAR element is active in many different cell types.

Chromatin openers or simply openers (the terms will be used interchangeably herein) are involved in opening chromatin structure, through chromatin-remodeling proteins and their complexes such as the Ash1 protein, the Brahma protein, other trxG proteins or components of the CHRAC NURF and ACF group chromatin-remodeling complexes. Alternatively, chromatin openers are histone modifiers, such as HAT proteins or functional relevant parts of such proteins that are still able to add acetyl groups to histone tails, which have the consequence that the tight association between the basic histones and the acid DNA is loosened. Yet another class of chromatin openers consists of specific histone methyltransferase, such as the Ash1 protein, that adds a methyl group to at least lysine 4 (K4) of histone H3 and that also results in opening of chromatin or making it more accessible to the general transcription machinery. Chromatin openers, these being chromatin-remodeling factors, specific HATs or HMTases or even other histone modifiers thus have in common that they facilitate the binding of transcription factors to the promoter and hence increase the possibilities for transcription.

Transcription can be influenced through a direct effect of the regulatory element (or the protein(s) binding to it) on the transcription of a particular promoter. Transcription can, however, also be influenced by an indirect effect, for instance, because the regulatory element affects the function of one or more other regulatory elements. A gene transcription modulating quality can also comprise a stable gene transcription quality. With "stable" is meant that the observed transcription level is not significantly changed over at least 5 to 60 cell divisions. A stable quality is useful in situations wherein expression characteristics should be predictable over many cell divisions. Typical examples are cell lines transfected with foreign genes. Other examples are transgenic animals and plants and gene therapies. Very often, introduced expression cassettes function differently after increasing numbers of cell divisions or plant or animal generations. Preferably, a stable quality comprises a capacity to maintain gene transcription in subsequent generations of a transgenic plant or animal. Of course, in the case where expression is inducible, the quality comprises the quality to maintain inducibility of expression in subsequent generations of a transgenic plant or animal. Frequently, expression levels drop dramatically with increasing numbers of cell divisions. The present invention provides a means for at least in part counteracting this drop.

The present invention provides, amongst others, a method for obtaining a cell which expresses one or more proteins. Openers are added to the expression unit of the gene of interest, preferably along with STAR elements that are applied to flank the expression units, both chromatin openers and STAR elements being the basis of the stable expression of the transgene protein over many cell generations. We have demonstrated that STAR elements can protect individual transgenes from silencing. Expression units that are not flanked by STAR elements can undergo significant silencing after only 5 to 60 culture passages, during which time silencing of the STAR element protected units is negligible.

The present invention uses chromatin openers and STAR sequences for the production of one or more proteins and thereby the invention provides (1) an increased predictability in the creation of recombinant cell lines that efficiently produce the heterologous multimeric proteins of interest, (2) an increased yield of the heterologous multimeric proteins, (3) stable expression of the heterologous multimeric proteins, even during prolonged cultivation in the absence of a selection agent and (4) favorable transgene expression characteristics without amplification of the transgene. The increased yield of heterologous proteins provided by the invention may be obtained at low transgene copy numbers, without selective co-amplification using, for example, the DHFR/methotrexate system. This results in greater stability, since the transgene copy number is low and is not susceptible to decrease due to recombination (McBurney et al., 2002) or repeat-induced gene silencing (Garrick et al., 1998). Fifth, the broad applicability of the method of the invention includes its utility in a wide range of host cell lines. This is, for example, useful/desirable when a particular multimeric protein is preferably expressed by a particular host cell line (e.g., expression of antibodies from lymphocyte-derived host cell lines).

A method according to the invention, therefore, provides an improvement of expression of one or more proteins in a (host) cell. In another embodiment, the invention provides a method for identifying a cell wherein expression of one or of more proteins in a predetermined ratio comprises providing:
    a collection of cells with one or more protein expression units encoding one or more proteins,
    selecting cells which express one or more proteins, and
    identifying from the obtained selection cells that express two or more proteins in the predetermined ratio, characterized in that at least two of the protein expression units comprise at least one chromatin opener identifying from the obtained selection cells that express two or more proteins in the predetermined ratio.

Preferably, at least one of the expression units comprises at least one STAR sequence.

The selection of cells which express one or more proteins can, for example, be obtained by performing an SDS-PAGE analysis, a Western blot analysis or an ELISA, which are all techniques that are known by a person skilled in the art and, therefore, need no further elaboration. The identification of cells that express two or more proteins in the predetermined ratio can also be performed by these techniques.

The presence of an opener and a STAR sequence in at least one of the protein expression units, again, provide the desired predictability, yield, and stability of one or more proteins.

In another embodiment, the invention provides a method wherein at least one of the protein expression units comprises a monocistronic gene comprising an open reading frame encoding a protein of interest and wherein, the monocistronic gene is under control of a functional promoter.

In yet another embodiment, the invention provides a method according to the invention, wherein at least one of the protein expression units comprises a bicistronic gene comprising an open reading frame encoding a protein of interest, a protein translation initiation site with a reduced translation efficiency, a selection marker and wherein, the bicistronic gene is under control of a functional promoter.

In a more preferred embodiment, the invention provides a method according to the invention, wherein at least one of the protein expression units comprises:
    a bicistronic gene comprising an open reading frame encoding a protein of interest, a protein translation initiation site with a reduced translation efficiency, a selection marker and wherein, the bicistronic gene is under control of a functional promoter, which protein expression unit further comprises:

a monocistronic gene comprising an open reading frame encoding a second selection marker and wherein, the monocistronic gene is under control of a functional promoter.

The term "bicistronic gene" is typically defined as a gene capable of providing an RNA molecule that encodes two proteins/polypeptides.

The term "monocistronic gene" is typically defined as a gene capable of providing an RNA molecule that encodes one protein/polypeptide.

The terms "selection marker" or "selectable marker" are typically used to refer to a gene and/or protein whose presence can be detected directly or indirectly in a cell, for example, a gene and/or a protein that inactivates a selection agent and protects the host cell from the agent's lethal or growth-inhibitory effects (e.g., an antibiotic-resistance gene and/or protein). Another possibility is that the selection marker induces fluorescence or a color deposit (e.g., green fluorescent protein and derivatives, luciferase, or alkaline phosphatase).

The term "selection agent" is typically defined as a means for selecting for the presence of a selectable marker, such as an antibody. A dominant selection agent" is typically defined as a chemical compound that is able to kill or retard the growth of host cells (e.g., an antibiotic).

The term "dominant selection" is typically defined as the process of using a selection marker/selectable marker and a dominant selection agent to identify host cells with specific genetic properties (e.g., that the host cell contains a transgene integrated into its genome).

The nouns "clone" and "isolate" typically refer to a recombinant host cell line that has been identified and isolated by means of selection.

Improvements provided by a method according to the invention have at least three aspects which may be integrated or not. (1) With existing systems, recombinant cell lines that simultaneously express acceptable quantities of the monomers of multimeric proteins can be created only at very low frequencies; the present invention increases the predictability of creating high-yielding recombinant host cell lines by a factor of ten or more. (2) Existing systems do not provide stoichiometrically balanced and proportional amounts of the subunits of multimeric proteins; the present invention ensures that the expression levels of the subunits will be balanced and proportional. (3) Existing systems do not provide a means of protecting the transgenes that encode the protein subunits from transgene silencing.

FIG. 1 provides a non-limiting schematic representation of one of the embodiments of this part of the invention.

This is the configuration of the DNA elements of the expression units in the plasmid as well as after integration into the genome. Expression unit one is shown in FIG. 1A. It contains an open reading frame for a transgene (a reporter gene, Gene 1). This is upstream of the attenuated EMCV IRES (Martinez-Sals et al., 1999; Mizuguchi et al., 2000; Rees et al., 1996) and of the open reading frame encoding the zeocin-resistance selectable marker protein (zeo). The gene cassette has the SV40 transcriptional terminator at their 3' ends (t). This bicistronic transgene is transcribed at high levels from the CMV promoter. Upstream of the CMV promoter are four LexA binding sites (LexA-BS). Next to this is the monocistronic gene encoding a fusion protein between the LexA protein and a histone acetyltransferase (HAT) or a functional part of a HAT that is still able to transfer acetyl groups to histone tails (LexA-HAT). Alternatively, a fusion protein is encoded between the LexA protein and a histone methyltransferase (HMTase) or a functional part of a HMTase protein that is still able to transfer a methyl group to at least lysine K4 of histone H3. Alternatively, a fusion protein is encoded between LexA and the Brahma protein. Either one of these monocistronic transcription units is transcribed from the SV40 promoter. The genes have the SV40 transcriptional terminator at their 3' ends (t). This entire cassette with multiple genes is flanked by STAR elements.

FIG. 1B is similar as FIG. 1A, but one plasmid contains now three expression units that encode, respectively, Gene 1, Gene 2 and LexA-HAT, LexA-HMTase or LexA-Brahma. The expression units encoding Gene 1 and Gene 2 are oriented divergent in such a manner that the two CMV promoters are adjacent, although differently oriented. Between the two promoters, LexA binding sites are placed to which the LexA fusion proteins are targeted. In this manner, chromatin openers are targeted to both expression units.

It is clear to a person skilled in the art that in these examples, more possible combinations can be made. For instance, the expression units can be made in such a manner that Gene 1, Gene 2 and the LexA-HAT, LexA-HMTase or LexA-Brahma or HAT each are located on separate plasmids. In addition, STAR elements can be omitted from these constructs and still the expression of gene 1 can be benefited from the presence of chromatin openers.

Selection of cells that harbor the depicted plasmids can be with co-transfection with, for instance, a plasmid that contains the puromycin-resistance gene. A second selection step can then involve adding Zeocin to the culture medium, since the Zeocin-resistance gene is coupled to the gene of interest (Gene 1). It is also possible to directly select on Zeocin, since the Zeocin-resistance gene is coupled to the gene of interest (Gene 1) through an IRES sequence. It is also possible that the expression unit encoding the puromycin-resistance gene is placed on the same plasmid as depicted in FIG. 1. It is also clear to a person skilled in the art that the possible combinations of selection markers are numerous. An example of a possible antibiotic is provided above. The one antibiotic that is particularly advantageous is zeocin, because the zeocin-resistance protein (zeocin-R) acts by binding the drug and rendering it harmless. Therefore, it is easy to titrate the amount of drug that kills cells with low levels of zeocin-R expression, while allowing the high expressers to survive. All other antibiotic-resistance proteins in common use are enzymes and thus act catalytically (not 1:1 with the drug). When a two-step selection is performed, it is, therefore, advantageous to use an antibiotic-resistance protein with this 1:1 binding mode of action. Hence, the antibiotic zeocin is a preferred selection marker. For convenience, the zeocin antibiotic is in a two-step selection method combined with puromycin-R or hygromycin-R in the monocistronic gene.

It is also possible to combine an antibiotic selection marker with a selection marker that provides induction of fluorescence or that provides a color deposit.

Different promoters can be used as long as they are functional in the used cell. The CMV promoter is considered the strongest available, so it is preferably chosen for the bicistronic gene in order to obtain the highest possible product yield. Other examples of preferred promoters are housekeeping gene promoters, preferred examples of such housekeeping gene promoters are the mammalian promoters for EF1-alpha or ubiquitin. The good expression and stability of the SV40 promoter makes it well suited for expression of the monocistronic gene; enough selection marker protein (for example, the antibiotic-resistance protein puromycin-R in the example cited herein) is made to confer high expression of the selection marker. Hence, the SV40 promoter is preferentially used as a promoter driving the expression of the selection marker.

In a preferred embodiment, the invention provides a method wherein at least one of the protein expression units comprises at least two STAR sequences. In an even more preferred embodiment, the invention provides a method wherein the protein expression unit comprising at least two STAR sequences is arranged such that the protein expression unit is flanked on either side by at least one STAR sequence. In yet an even more preferred embodiment, the at least two STAR sequences are essentially identical. Essentially identical STAR sequences are defined herein as STAR sequences which are identical in their important domains, but which may vary within their less important domains (the domains that confer the transcription stabilizing or enhancing quality), for example, a point mutation, deletion or insertion at a less important position within the STAR sequence. Preferentially, the essentially identical STAR sequences provide equal amounts of transcription stabilizing or enhancing activity.

The use of STARs to flank at least one protein expression unit is one of the aspects of the balanced and proportional levels of expression of two or more proteins and, more specifically, for the expression of the monomers of multimeric proteins. The STARs create chromatin domains of definite and stable transcriptional potential. As a result, promoters that drive transcription of each bicistronic mRNA will function at definite, stable levels. A recombinant host cell line created by the method of the invention is readily identified in which these levels result in appropriate proportions of each monomer of the multimeric protein of interest being expressed at high yields.

Yet another preferred feature of a method according to the invention is the introduction of a (weak) Internal Ribosome Binding Site (IRES) as an example of a protein translation initiation site with a reduced translation efficiency between the open reading frame of the protein of interest and the selection marker open reading frame. Translation of proteins from IRES elements is less efficient than cap-dependent translation: the amount of protein from IRES-dependent open reading frames (ORFs) ranges from less than 20% to 50% of the amount from the first ORF (Mizuguchi et al., 2000). This renders IRES elements undesirable for production of all subunits of a multimeric protein from one messenger RNA (mRNA), since it is not possible to achieve balanced and proportional expression of two or more protein monomers from a bicistronic or multicistronic mRNA. However, the reduced efficiency of IRES-dependent translation provides an advantage that is exploited by the current invention. Furthermore, mutation of IRES elements can attenuate their activity and lower the expression from the IRES-dependent ORFs to below 10% of the first ORF (Lopez de Quinto and Martinez-Salas, 1998; Rees et al., 1996). The advantage exploited by the invention is as follows: when the IRES-dependent ORF encodes a selectable marker protein, its low relative level of translation means that high absolute levels of transcription must occur in order for the recombinant host cell to be selected. Therefore, selected recombinant host cell isolates will, by necessity, express high amounts of the transgene mRNA. Since the recombinant protein is translated from the cap-dependent ORF, it can be produced in abundance resulting in high product yields.

It is clear to a person skilled in the art that changes to the IRES can be made without altering the essence of the function of the IRES (hence, providing a protein translation initiation site with a reduced translation efficiency), resulting in a modified IRES. Use of a modified IRES that is still capable of providing a small percentage of translation (compared to a 5' cap translation) is, therefore, also included in this invention.

In yet another embodiment, the invention provides a method for obtaining a cell which expresses two or more proteins or a method for identifying a cell wherein expression of two or more proteins is in a predetermined ratio, wherein each of the protein expression units resides on a separate DNA carrier. The present invention preferentially makes use of a separate transcription unit for each protein and/or monomer of a multimeric protein. In each transcription unit, the monomer ORF is produced by efficient cap-dependent translation. This feature of the invention contributes that recombinant host cells are isolated that have high yields of each monomer at levels that are balanced and proportionate to the stoichiometry of the multimeric protein. The increased predictability at which such recombinant host cells are isolated results in an improvement in the efficiency of screening for such isolates by a factor of ten or more. In a preferred embodiment, the DNA carrier is a vector (or plasmid; the terms are used interchangeably herein). In another embodiment, the vector is a viral vector and in a more preferred embodiment, the viral vector is an adenoviral vector or a retroviral vector. Other viral vectors can also be used in a method according to the invention.

Conventional expression systems are DNA molecules in the form of a recombinant plasmid or a recombinant viral genome. The plasmid or the viral genome is introduced into (mammalian host) cells and integrated into their genomes by methods known in the art. The present invention also uses these types of DNA molecules to deliver its improved transgene expression system. A preferred embodiment of the invention is the use of plasmid DNA for delivery of the expression system. A plasmid contains a number of components: conventional components known in the art are an origin of replication and a selectable marker for propagation of the plasmid in bacterial cells; a selectable marker that functions in eukaryotic cells to identify and isolate host cells that carry an integrated transgene expression system; the protein of interest whose high-level transcription is brought about by a promoter that is functional in eukaryotic cells (e.g., the human cytomegalovirus major immediate early promoter/enhancer, pCMV (Boshart et al., 1985)); and viral transcriptional terminators (e.g., the SV40 polyadenylation site (Kaufman and Sharp, 1982)) for the transgene of interest and the selectable marker.

The vector used can be any vector that is suitable for cloning DNA and that can be used in a transcription system. When host cells are used, it is preferred that the vector is either an integrating vector or an episomally replicating vector. In an episomally replicating vector, effects due to different sites of integration of the vector are avoided. DNA elements flanking the vector at the site of integration can have effects on the level of transcription of the promoter and thereby mimic effects of fragments comprising DNA sequences with a gene transcription modulating quality. In a preferred embodiment, the vector comprises a replication origin from the Epstein-Barr virus (EBV), OriP, and a nuclear antigen (EBNA-1). Such vectors are capable of replicating in many types of eukaryotic cells and assemble into chromatin under appropriate conditions.

In particular embodiments, the invention provides a method for obtaining a cell which expresses two or more proteins or a method for obtaining a cell, wherein expression of two or more proteins is in a predetermined ratio comprising providing two or more protein expression units, wherein one of the protein expression units or protein(s) of interest encodes an immunoglobulin heavy chain and/or wherein another of the protein expression units or protein(s) of interest encodes an immunoglobulin light chain. According to this embodiment, a multimeric protein, an antibody, is obtained. It is clear to a person skilled in the art that it is possible to provide a cell which expresses an immunoglobulin heavy chain from one protein expression unit and an immunoglobulin light chain from another protein expression unit with a third protein expression unit encoding a secretory component or a joining chain. In this way, the production of, for example, sIgA and pentameric IgM is provided.

In yet another embodiment, a method according to the invention is provided, wherein the protein expression units are introduced simultaneously into the cell.

Preferably, a functional promoter is a human cytomegalovirus (CMV) promoter, a simian virus (SV40) promoter, a human ubiquitin C promoter or a human elongation factor alpha (EF1-α) promoter.

In another embodiment, the invention provides a protein expression unit comprising:
- a bicistronic gene comprising an open reading frame encoding a protein of interest, a protein translation initiation site with a reduced translation efficiency, a selection marker and wherein the bicistronic gene is under control of a functional promoter and
- at least one chromatin opener and
- at least one STAR sequence and/or at least two TRAP sequences.

In a more preferred embodiment, the protein expression unit comprises a chromatin opener and at least two STAR sequences that are preferentially arranged such that the protein expression unit is flanked on either side by at least one STAR sequence. Examples of such a protein expression unit are provided within the experimental part of this patent application.

In another embodiment, the protein expression unit according to the invention comprises STAR sequences, wherein the STAR sequences are essentially identical.

In a preferred embodiment, the invention provides a protein expression unit comprising:
- a bicistronic gene comprising an open reading frame encoding a protein of interest, a protein translation initiation site with a reduced translation efficiency, a selection marker and wherein the bicistronic gene is under control of a functional promoter,
- at least one STAR sequence and is optionally provided with a monocistronic gene cassette, wherein the STAR sequence is depicted in Table 1 and/or a functional equivalent and/or a functional fragment thereof,
- at least two TRAP sequences that are positioned to flank the STAR elements and wherein the TRAP sequences are depicted in Table 2.

In another embodiment, a protein expression unit according to the invention is provided wherein the protein translation initiation site with a reduced translation efficiency comprises an Internal Ribosome Entry Site (IRES). More preferably, a modified, e.g., weaker, IRES is used.

In yet another embodiment, a protein expression unit according to the invention is provided wherein the protein expression unit is a vector. In a preferred embodiment, the DNA carrier is a vector (or plasmid; the terms are used interchangeably herein). In another embodiment, the vector is a viral vector and in a more preferred embodiment, the viral vector is an adenoviral vector or a retroviral vector. It is clear to a person skilled in the art that other viral vectors can also be used in a method according to the invention.

In a preferred embodiment, a protein expression unit according to the invention is provided, wherein the protein of interest is an immunoglobulin heavy chain. In yet another preferred embodiment, a protein expression unit according to the invention is provided, wherein the protein of interest is an immunoglobulin light chain. When these two protein expression units are present within the same (host) cell, a multimeric protein and, more specifically, an antibody, is assembled.

The invention includes a cell provided with a protein expression unit comprising a chromatin opener and a STAR element. The invention also includes a (host) cell comprising at least one protein expression unit according to the invention. Such a (host) cell is then, for example, used for large-scale production processes. The invention also includes a cell obtainable according to any one of the methods as described herein. The invention furthermore includes a protein obtainable from the cell (for example, via the process of protein purification). Preferably, the protein is a multimeric protein and even more preferably, the multimeric protein is an antibody. Such an antibody can be used in pharmaceutical and/or diagnostic applications.

The foregoing discussion and the following examples are provided for illustrative purposes and they are not intended to limit the scope of the invention as claimed herein. They simply provide some of the preferred embodiments of the invention. Modifications and variations that may occur to one of ordinary skill in the art are within the intended scope of this invention. Various other embodiments apply to the present invention, including: other selectable marker genes; other IRES elements or means of attenuating IRES activity; other elements affecting transcription including promoters, enhancers, introns, terminators, and polyadenylation sites; other orders and/or orientations of the monocistronic and bicistronic genes; other anti-repressor elements or parts, derivations, and/or analogues thereof; other vector systems for delivery of the inventive DNA molecules into eukaryotic host cells; and applications of the inventive method to other transgenic systems.

The invention is further described with the aid of the following illustrative examples.

EXAMPLES

Example 1

Expression of LexA-HAT and LexA-Brahma and Brahma Proteins in CHO Cells

In one aspect, the invention applies chromatin openers to improve the predictability, yield and stability of transgenes in mammalian cell lines. Here, we introduce several chromatin openers into CHO cells and we describe the construction of the various opener constructs.

Materials and Methods

Plasmids

The construction of the pPlug&Play-d2EGFP-ires-Zeo (PP) vector is described below. Plasmid pd2EGFP (Clontech 6010-1) is modified by insertion of a linker at the BsiWI site to yield the pd2EGFP-link. The linker (made by annealing oligonucleotides GTACGGATATCAGATCTTTAATTAAG (SEQ ID NO:15) and GTACCTTAATTAAAGAT CTGATAT (SEQ ID NO:16)) introduces sites for the PacI, BglII, and EcoRV restriction endonucleases. This creates the multiple cloning site MCSII for insertion of STAR elements. Then primers gATCAgATCTggCgCgCCATT- TAAATCgTCTCgCgCgTTTCggTgATgACgg (SEQ ID NO:17) and AggCggATCCgAATgTATTTA-gAAAAATAAACAAATAgggg (SEQ ID NO:18) are used to amplify a region of 0.37 kb from pd2EGFP, which is inserted into the BglII site of pIRES (Clontech 6028-1) to yield pIRES-stuf. This introduces sites for the AscI and SwaI restriction endonucleases at MCSI and acts as a "stuffer fragment" to avoid potential interference between STAR elements and adjacent promoters. pIRES-stuf is digested with BglII and FspI to liberate a DNA fragment composed of the stuffer fragment, the CMV promoter, the IRES element (flanked by multiple cloning sites MCS A and MCS B), and the SV40 polyadenylation signal. This fragment is ligated with the vector backbone of pd2EGFP-link produced by digestion with BamHI and StuI to yield pd2IRES-link.

The open reading frames of the zeocin-resistance genes is inserted into the BamHI/NotI sites of MCS B in pd2IRES-link as follows: the zeocin-resistance ORF is amplified by PCR with primers gATCggATCCTTCgAAATggCCAAgT-TgACCAgTgC (SEQ ID NO:19) and AGGCGCGGCCG-CAATTCTCAGTCCTGCTCCTC (SEQ ID NO:20) from plasmid pEM7/zeo, digested with BamHI and NotI, and ligated with BamHI/NotI-digested pd2IRES-link to yield pd2IRES-link-zeo.

The SEAP reporter ORF is introduced into pd2IRES-link-zeo by PCR amplification of pSEAP2-basic with primers gATCgAATTCTCgCgACTTCgCCCACCATgC (SEQ ID NO:21) and AggCgAATTCAccggTgTTTAAACTCAT-gTCTgCTCgAAgCggCCgg (SEQ ID NO:22), and insertion of the EcoRI-digested SEAP cassette into the EcoRI sites in MCS A of the plasmids pd2IRES-link-zeo (to yield plasmid PP2). PP2 is cut with EcoRI and MluI to remove the SEAP gene and p2EGFP is introduced with primers GATCGAAT-TCATGGTGAGCAAGGGCGAGGAG (SEQ ID NO:23) and AGGCACGCGTGTTAACCTACACAT-TGATCCTAGCAGAAGC (SEQ ID NO:24). This vector is used as a basis vector to construct PP-LexA (PPL), PP-LexA-Brm (PPLBrm), PP-LexA-PCAF (PPLPCAF), PP-LexA-p300HAT (PPLp300) and PP-LexA-Ash1HMTase (PPL-HuAsh1).

Brm coding sequence is pcr amplified from plasmid pSVh-SNF-α (Chiba et al., 1994) using primers Brm-a1F-H3-AgeI (GATCAAGCTTACCGGTATGTCCACGCCCACAGA CCCTGGTGC (SEQ ID NO:25)) and Brm-a1572R-XbaI (AGGCTCTAGAATCACTCATCA TCCGTCCCACTTC-CTTC (SEQ ID NO:26)) and cloned into pPur (BD Biosciences #6156-1) using HindIII and XbaI to create pPur-Brm. LexA binding sites (LBS) are amplified from plasmid pREP4-HSF-Luc+ (van der Vlag et al., 2000) using primers LBS-for-SalI (AGGCGTCGACGTTTCGACTC-CCAAGCTTTG (SEQ ID NO:27)) and LBS-rev-AscI (GATCGGCGCGCCGGTACCATAGCGGCCGCGAC (SEQ ID NO:28)) and cloned upstream of the CMV promoter in PP using SalI and AscI to create PPLbs. LexA is amplified from plasmid pEG202 (Bennetzen and Hall, 1982) using primers LexA-for-H3 (GATCAAGCTTATGAAGACGT-TAACGGCCAGGC (SEQ ID NO:29)) and LexA-rev-AgeI (AGGCACCGGTCAGCCAGTCGCCGTTGCGAATAACC (SEQ ID NO:30)) and cloned downstream of the SV40 promoter in plasmid pPur using HindIII and AgeI creating pPur-LexA. Oligos Link-for-Bsu (GATCTCCCCTGAGGAAGT-GCACAACCTGAGGCC (SEQ ID NO:31)) and Link-rev-Bsu(GATCTGGCCTCAGGTTGTGCACTTCCTCAG GGG (SEQ ID NO:32)) are ligated into the BamHI site of pPur-LexA to create pPur-LexA-linker.

The control vector PPlbs-lexA (PPL) is created by removing the puro coding sequence from pPur-LexA using AgeI and XbaI, followed by a transfer of the LexA cassette (ApaLIxEcoRI, blunted) into the EcoRV site of PPlbs.

The Brm pcr-product (primers Brm-a1F-H3-AgeI and Brm-a1572R-XbaI) is cloned into pPur-LexA using AgeI and XbaI to create pPur-LexA-Brm. The P/CAF coding sequence is pcr amplified from plasmid pCX-P/CAF (Martinez-Balbás et al., 2000) using primers PCAF-a1F-h3-AgeI (GAT-CAAGCTTACCGGTATGTCCGAGGCTGGCGGGGCCG (SEQ ID NO:33)) and PCAF-a833R-XbaI (AGGCTCTA-GAATCACTTGTCAATTAA TCCAGCTTCC (SEQ ID NO:34)) and cloned into pPur-LexA-linker using AgeI and XbaI to create pPur-LexA-PCAF.

The LexA-Brm cassette is cut from pPur-LexA-Brm using ApaLI and EcoRI and blunted into the EcoRV site of PPLbs creating PPLBrm. P/CAF is cut from pPur-LexA-PCAF and cloned into PPLBrm using AgeI and ApaLI/PacI creating PPLPCAF. The HAT domain of human p300 is pcr amplified from plasmid pCMVβ-p300 (Martinez-Balbás et al., 2000) using primers p300-a934F-AgeI (GATCACCGGTCAGC-CTGCAACTCCACT TTCCCAGCC (SEQ ID NO:35)) and p300-a1652R-NheI (AGGCGCTAGCCTACATGGT GGACCACTGGGCTCTTCGG (SEQ ID NO:36)) and cloned into PPLBrm using AgeI and NheI/XbaI to create PPLp300 (FIG. 1A). The HMTase domain of human Ash1 is PCR amplified using primers HuAsh1,aa1787-For (gatcac-cggtacaagcagctgttccccccatcatatc (SEQ ID NO:37)) and HuAsh1,aa2393-Rev (aggcgctagctcataatgatgctgagt-gaatattatcac (SEQ ID NO:38)) and cloned into AgeI and NheI-digested PPLBrm to create PPLHuAsh1.

5' STARs are cloned into the SalI site of the various PPL constructs. 3' STARs are cloned either into the PacI site (PPL, PPLBrm and PPLp300) or the Bsu36I site (PPLPCAF).

Transfection and Culture of CHO Cells

The Chinese Hamster Ovary cell line CHO-K1 (ATCC CCL-61) is cultured in HAMS-F12 medium+10% Fetal Calf Serum containing 2 mM glutamine, 100 U/ml penicillin, and 100 micrograms/ml streptomycin at 37° C./5% $CO_2$. Cells are transfected with the plasmids using SuperFect (QIAGEN) as described by the manufacturer. Briefly, cells are seeded to culture vessels and grown overnight to 70 to 90% confluence. SuperFect™ reagent is combined with plasmid DNA at a ratio of 6 microliters per microgram (e.g., for a 10 cm Petri dish, 20 micrograms DNA and 120 microliters SuperFect™) and added to the cells. After overnight incubation, the transfection mixture is replaced with fresh medium and the transfected cells are incubated further. After overnight cultivation, cells are trypsinized and seeded into fresh culture vessels with fresh medium. After another overnight incubation, zeocin is added to a concentration of 50 μg/ml and the cells are cultured further. After another three days, the medium is replaced by fresh medium containing zeocin (100 μg/ml) and cultured further. When individual colonies become visible (approximately ten days after transfection), medium is removed and replaced with fresh medium without zeocin. Individual clones are isolated and transferred to 24-well plates in medium without zeocin. One day after isolation of the colonies, zeocin is added to the medium. Expression of the GFP reporter gene is assessed approximately three weeks after transfection.

Example 2

Chromatin Openers Improve the Level of Transgene Expression

Figure 2:
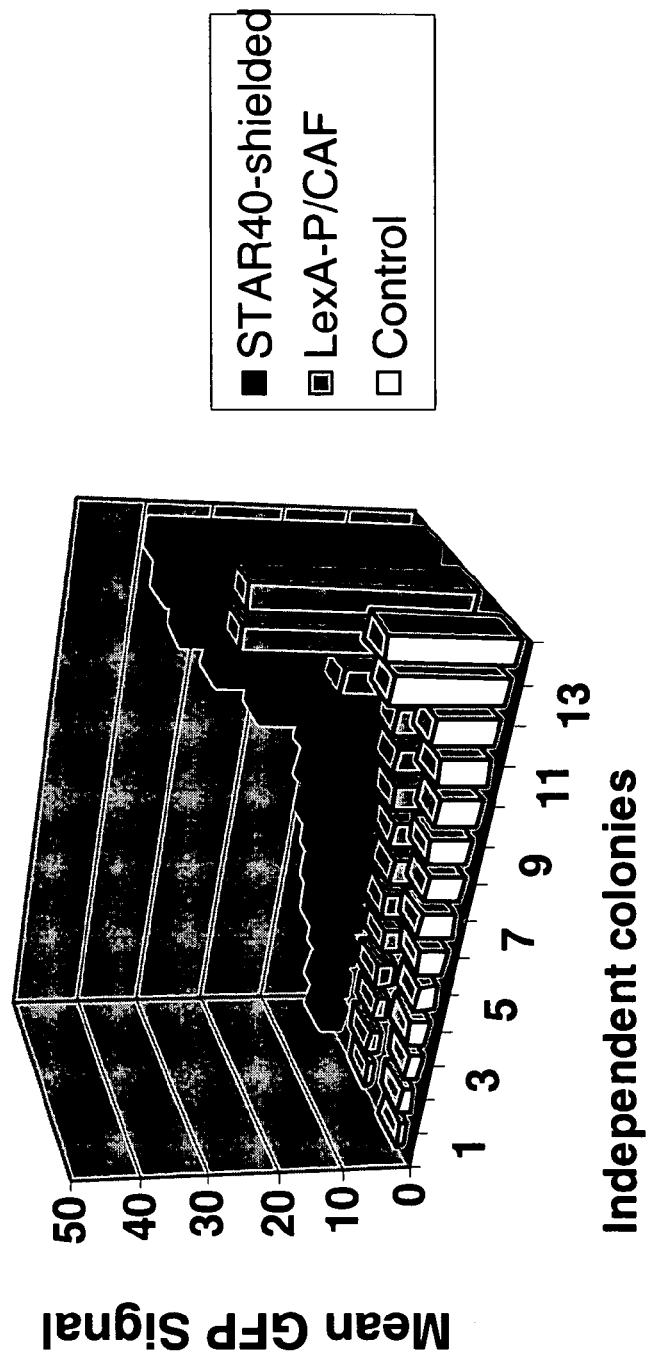
FIG. 2. Chromatin openers improve CMV-driven GFP expression in CHO cells. The constructs that contain the gene encoding LexA-P/CAF are transfected to CHO-K1 cells. Stable colonies (14 of each construct) are expanded and the GFP signal is determined on an XL-MCL Beckman Coulter flow cytometer. For each independent colony, the mean of the GFP signal is plotted. This is taken as the measurement for the level of GFP expression. The results are compared to colonies that are transfected with a construct containing no LexA-P/CAF gene (Control) and a construct that is flanked with STAR40 elements (STAR40-shielded) at both the 5' and 3' end.

In one asptect, the invention improves both the predictability and the levels of transgene expression for heterologous protein production, thus increasing the yield of the heterologous protein and reducing the number of colonies that have to be analyzed to obtain a high producer colony.
Materials and Methods The tested construct consists of a bicistronic gene with the GFP gene, an IRES, and the Zeocin-resistance gene under control of the CMV promoter and a monocistronic gene encoding LexA-P/CAF under control of the SV40 promoter, but no STAR elements to flank the entire construct. The construct is transfected to CHO-K1 cells as in Example 1. Stable colonies are expanded before the GFP signal is determined on an XL-MCL Beckman Coulter flow cytometer. The mean of the GFP signal is taken as the measurement for the level of GFP expression and this is plotted in FIG. 2. The results are compared to colonies that are transfected with a construct containing no LexA-P/CAF gene (Control) and a construct that is flanked with STAR40 elements (STAR40-shielded) at both the 5' and 3' end, but that contains no LexA-P/CAF.
Results FIG. 2 shows that targeting LexA-P/CAF to LexA binding sites upstream of the CMV promoter results in a number of CHO colonies that express significantly higher levels of GFP protein, as compared to the "empty" control without LexA-P/CAF. The GFP signal in the colonies with the highest signals is comparable to the highest GFP signal that are obtained with a construct that has flanking STAR40 elements, but no LexA-P/CAF. However, similar to the distribution of the GFP signals amongst the various colonies, most colonies do not express GFP or only at a low level. This indicates that the predictability of the protein expression is not significantly altered as compared to the "empty" control construct. When compared to the GFP signals in colonies transfected with a STAR-shielded construct, these STAR elements convey a higher degree of predictability. The highest GFP expression level in STAR-shielded colonies is of the same order as the GFP expression level in LexA-P/CAF colonies. However, there are significantly more STAR-shielded colonies that show a high GFP expression level. It is, therefore, concluded that the LexA-P/CAF opener is able to convey higher expression levels to a transgene, but that they do not convey a higher predictability of transgene expression. Higher predictability is better achieved when STAR elements are added to a construct.

Example 3

Figure 3:
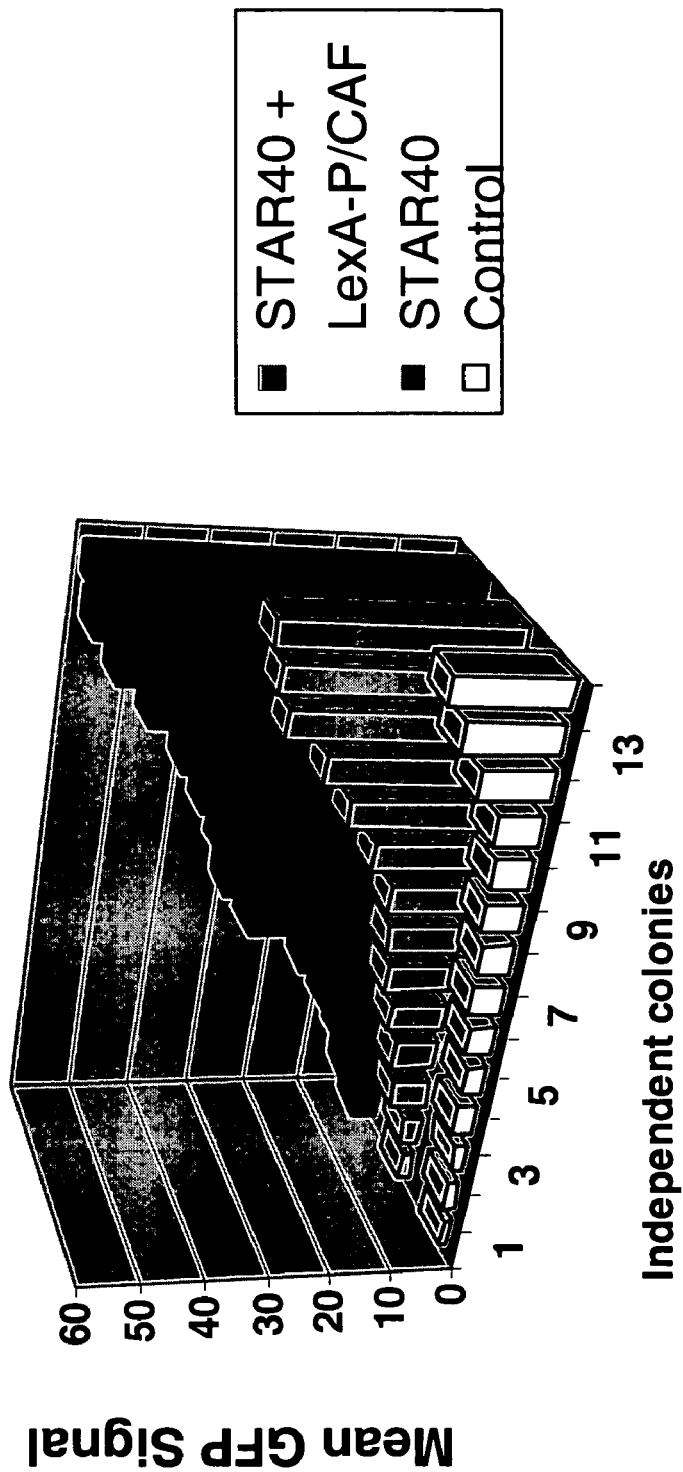
FIG. 3. The combination of chromatin openers and STARs enhances CMV promoter-driven GFP expression in CHO cells. The construct that is flanked by STAR40 and that contains the gene encoding LexA-P/CAF (see FIG. 1) is transfected to CHO-K1 cells. Stable colonies (14 of each construct) are expanded, the GFP signal is determined and the mean of the GFP signal is plotted as in FIG. 2. The results are compared to colonies that are transfected with a construct containing no LexA-P/CAF or STAR40 elements (Control) and a construct that is flanked with STAR40 elements (STAR40) at both the 5' and 3' end.

The Combination of Chromatin Openers and STAR Elements Improves Predictability and Yields of Transgene Expression Openers are combined with STAR elements as described in FIG. 1 and tested are the predictability and yield of transgene expression in stably transfected, individual colonies.
Materials and Methods The tested construct consists of a bicistronic gene with the GFP gene, an IRES, and the Zeocin-resistance gene under control of the CMV promoter and a monocistronic gene encoding LexA-P/CAF under control of the SV40 promoter. The entire construct is flanked by STAR40 (FIG. 1A). The construct is transfected to CHO-K1 cells as in Example 1. Stable colonies are expanded before the GFP signal is determined on an XL-MCL Beckman Coulter flow cytometer. The mean of the GFP signal is taken as the measurement for the level of GFP expression and this is plotted in FIG. 3. Results are compared to colonies transfected with a construct containing no LexA-P/CAF gene and no STAR elements ("empty" control) and a construct that contains no LexA-P/CAF gene, but flanked with STAR40 at both the 5' and 3' end.
Results FIG. 3 shows that the construct in which LexA-P/CAF is targeted to the CMV promoter and that is flanked by STAR elements conveys high GFP expression levels. The highest GFP expression level is more than three-fold higher than the highest levels in the "empty" control. Moreover, a high degree of predictability of GFP expression levels is found amongst various colonies. In contrast to colonies that express a construct with LexA-P/CAF alone (FIG. 2), more colonies that contain the construct with LexA-P/CAF and STAR40 elements have a high level of GFP expression. It is, therefore, concluded that the combination of STAR elements and an opener conveys both high protein expression levels and a high degree of predictability of expression.

Example 4

Figure 4:
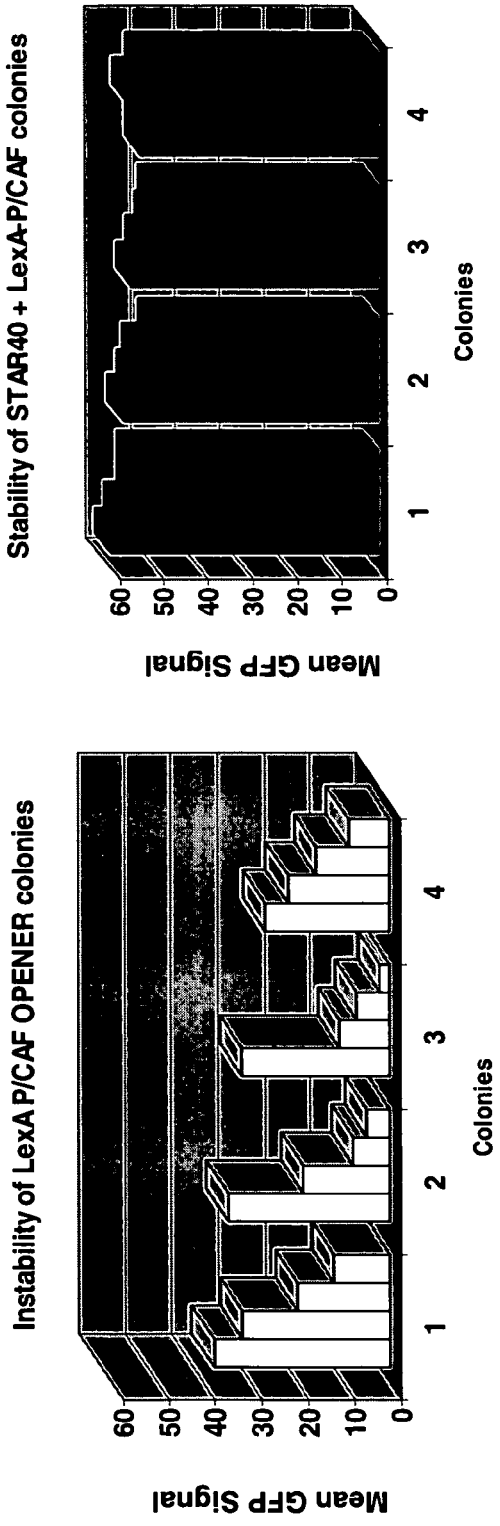
FIG. 4. The combination of chromatin openers and STARs enhances the stability of CMV promoter-driven GFP expression in CHO cells. Stably transfected colonies that contain either the LexA-P/CAF opener construct or the GFP construct that is flanked by STAR40, as well as contains the gene encoding LexA-P/CAF (see FIG. 1), are expanded. Of both categories, four colonies are chosen with the highest GFP levels (see FIG. 3). These colonies are further cultured without the antibiotic (zeocin) and the GFP signal is determined with intervals of one week, which represent approximately ten cell cycles. The mean of the GFP signal is plotted as in FIG. 3. The first bar of each colony represents the GFP signal at the moment that the antibiotic selection pressure is removed. The adjacent three bars represent the GFP signal that is measured after one, two and three weeks.

Stability of Transgene Expression is Improved by Application of Chromatin Openers and STARs in Expression Systems During cultivation of recombinant host cells, it is common practice to maintain antibiotic selection. This is intended to prevent transcriptional silencing of the transgene, or loss of the transgene from the genome by processes such as recombination. However, it is undesirable for production of proteins for a number of reasons. First, the antibiotics that are used are quite expensive and contribute significantly to the unit cost of the product. Second, for biopharmaceutical use, the protein must be demonstrably pure, with no traces of the antibiotic in the product. One advantage of STAR elements for heterologous protein production is that they confer stable expression on transgenes during prolonged cultivation, even in the absence of antibiotic selection; this property is demonstrated in this example and shown in FIG. 5.
Materials and Methods GFP expression levels in the colonies that are described in Examples 2 and 3 are measured after a period of one week. After the initial three weeks after transfection when the first GFP measurements were performed, the colonies were cultured in medium without zeocin or other antibiotics. This continued for the remainder of the experiment.
Results FIG. 4 shows the data on GFP expression of colonies that are stably transfected with the construct in which LexA-P/CAF is targeted to the CMV promoter and that is flanked by STAR elements. The colonies with the highest GFP expression levels in FIG. 3 are chosen for analysis of stability of expression over time in the absence of selection pressure by antibiotics. The expression of the reporter GFP protein remains stable in the CHO cells in three time points. The first time point represents the start of the experiment when the selection pressure is removed. Measurements are performed after one, two and three weeks, which signify approximately 10, 20 and 30 cell cycles, respectively. Colonies containing the STAR40 and LexA-P/CAF are stable in the absence of antibiotics, but colonies containing only the LexA-P/CAF are not stable in the absence of antibiotics. This demonstrates that application a combination of openers and STAR elements protect transgenes from silencing during prolonged cultivation. It also demonstrates that this property is independent of antibiotic selection.

Example 5

The p300HAT Chromatin Opener has No Effect on Transient Gene Expression Driven by the CMV and UB6 Promoters, but Does Have an Effect on a Minimal Promoter The nature of the effects of openers on gene expression is investigated. One possible way of action is that the openers act in a transient manner on promoters and that this effect is subsequently transmitted to stable clones. Hence, we tested the effects of several openers on transient expression levels. Promoters used are the strong CMV and UB6 promoters, as well as the minimal SV40 promoter.

Materials and Methods

Plasmids

The reporter constructs consist of the DsRED gene under the control of either the CMV, UB6 or the minimal SV40 promoter. Upstream of these promoters are LexA binding sites. LexA binding sites (LBS) are amplified from plasmid pREP4-HSF-Luc+(van der Vlag et al., 2000) using primers LBS-for-SalI (AGGCGTCGACGTTTCGACTC-CCAAGCTTTG (SEQ ID NO:27)) and LBS-rev-AscI (GATCGGCGCGCCGGTACCATAGCGGCCGCGAC (SEQ ID NO:28)) and cloned upstream of the promoters in PP using SalI and AscI. Another construct contains a gene encoding a portion of the p300 gene, encoding the histone acetyltransferase domain (HAT). The HAT domain of human p300 is pcr amplified from plasmid pCMVβ-p300 (Martinez-Balbás et al., 2000) using primers p300-a934F-AgeI (GATCAC-CGGTCAGCCTGCA ACTCCACTTTCCCAGCC (SEQ ID NO:35)) and p300-a1652R-NheI (AGGCGCTAGCCTA CATGGTGGACCACTGGGCTCTTCGG (SEQ ID NO:36)) and cloned using AgeI and NheI/XbaI to create PPLp300HAT. The p300HAT domain is cloned in frame with the LexA protein and the entire cassette is placed under control of the SV40 promoter.

Transfection and Culture of CHO Cells

The Chinese Hamster Ovary cell line CHO-K1 (ATCC CCL-61) is cultured in HAMS-F12 medium+10% Fetal Calf Serum containing 2 mM glutamine, 100 U/ml penicillin, and 100 micrograms/ml streptomycin at 37° C./5% $CO_2$. Cells are transfected using Lipofectamine 2000 (Invitrogen) as described by the manufacturer. The DsRED reporter gene with the different promoters is transfected either alone or in combination with the SV40-p300HAT construct. Transfected cells are seeded in culture vessels and grown overnight to 70 to 90% confluence. Lipofectamine reagent is combined with plasmid DNA at a ratio of 7.5 microliters per 3 micrograms and added after 30 minutes incubation at 250° C. to the cells. After six hours incubation, the transfection mixture is replaced with fresh medium and the transfected cells are incubated further. Twenty-four hours after transfection, the DsRED signal is determined on an XL-MCL Beckman Coulter flow cytometer. The mean of the DsRED signal is taken as the measurement for the level of DsRED expression and this is plotted in FIG. 5.

Results

Figure 5:
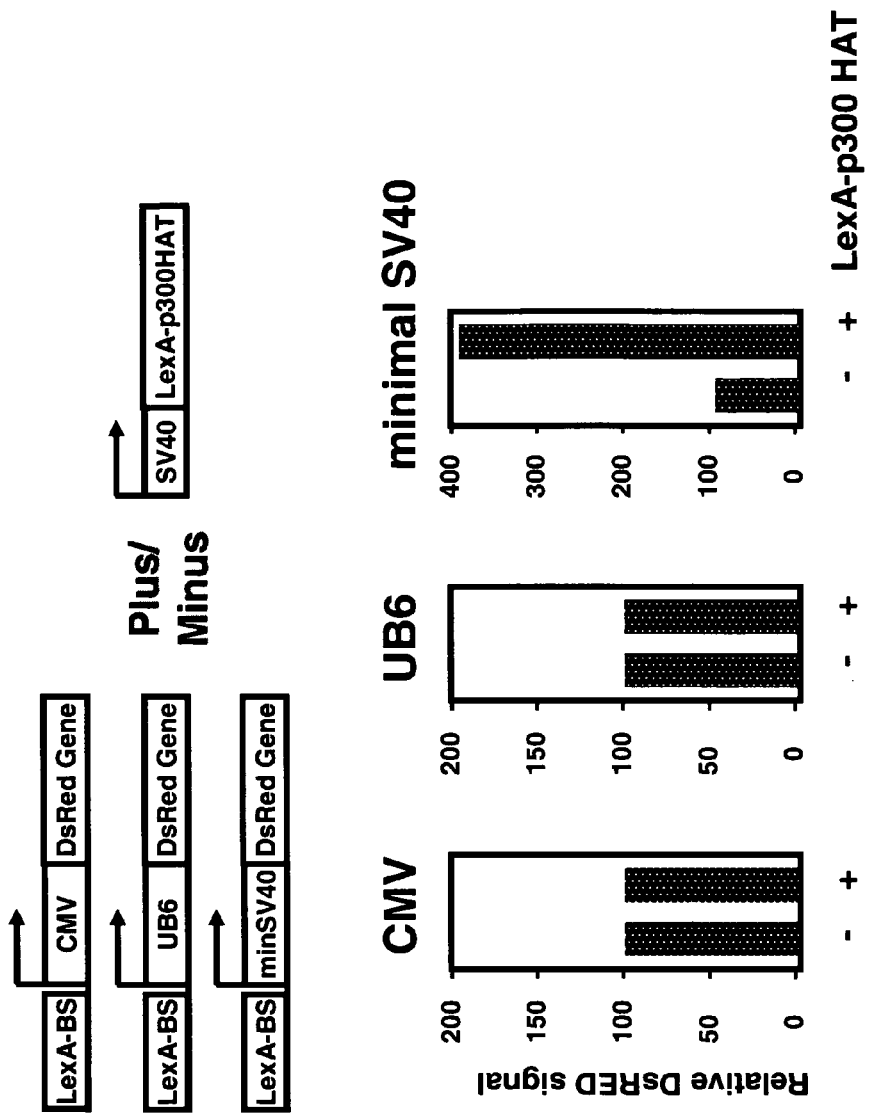
FIG. 5. LexA-P300HAT does not enhance transient expression of the CMV and UB6 promoter, but only of the minimal SV40 promoter. Two different classes of plasmids are shown. Class one comprises the DsRED reporter gene under control of the CMV, UB6 or minimal SV40 promoter. Upstream of these promoters are four LexA binding sites (LexA-BS). The second class of plasmid is a gene encoding a fusion protein between the LexA protein and the functional P300 histone acetyltransferase (HAT) domain. The different reporter gene constructs are transfected alone or together with the plasmid encoding the LexA-P300HAT Opener protein. Twenty-four hours after transfection, the DsRED signals are measured. The signal measured with only the reporter gene construct is set arbitrarily at 100. The signal of such a reporter gene alone is compared with the signal of that respective reporter gene construct in combination with the LexA-P300HAT Opener construct.

FIG. 5 shows that targeting LexA-P300 HAT to LexA binding sites upstream of the CMV or the UB6 promoter does not result in an increase of DsRED expression. However, when the Lex-P300HAT is expressed with the plasmid containing the DsRED gene driven by the SV40 minimal promoter, an increase of 400% is seen. Thus, the Lex-P300HAT does not enhance transient expression levels of CMV and UB6-driven gene expression, but only of a minimal promoter, in this case the SV40 minimal promoter.

Example 6

The p300HAT Opener Improves the Level of CMV-Driven Expression in Stably Transfected Clones, but Only for a Limited Period During cultivation of recombinant host cells, it is common practice to maintain antibiotic selection. This is intended to prevent transcriptional silencing of the transgene or loss of the transgene from the genome by processes such as recombination. However, it is undesirable for production of proteins, for a number of reasons. First, the antibiotics that are used are quite expensive and contribute significantly to the unit cost of the product. Second, for biopharmaceutical use, the protein must be demonstrably pure, with no traces of the antibiotic in the product. In this example, we test whether the P300HAT Opener is able to induce stability of gene expression over an extended period of time.

Materials and Methods

Plasmids

Figure 6:
FIG. 6. The p300HAT opener improves the level of CMV-driven expression in stably transfected clones, but only for a limited period. Two different constructs are transfected to CHO-K1 cells. Construct one comprises a bicistronic gene containing (from 5' to 3') the d2EGFP reporter gene, an IRES, and a selectable marker (zeo, conferring zeocin resistance) under control of the CMV promoter (CMV Control).
Figure 6:
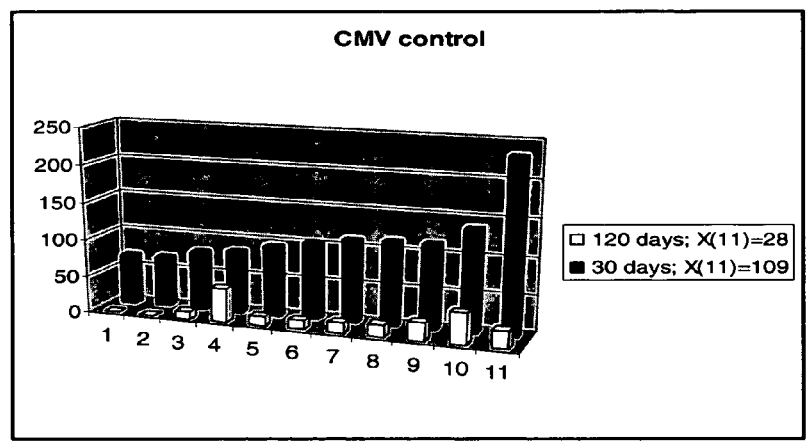
Figure 6:
Figure 6:
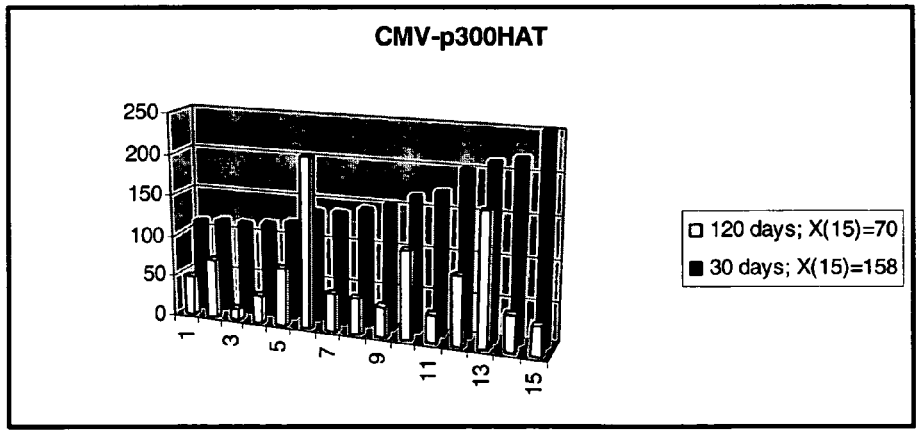

Two plasmids are compared in this experiment: the CMV-d2EGFP-ires-Zeo (CMV Control) vector and the CMV-d2EGFP-ires-Zeo--LexA-P300HAT (CMV-p300HAT) (FIG. 6). The open reading frame of the zeocin-resistance gene is inserted into BamHI/NotI sites downstream of the pIRES as follows: the zeocin-resistance ORF is amplified by PCR with primers gATCggATCCTTCgAAATggCCAAgT-TgACCAgTgC (SEQ ID NO:19) and AGGCGCGGCCG-CAATTCTCAGTCCTGCTCCTC (SEQ ID NO:20) from plasmid pEM7/zeo, digested with BamHI and NotI, and ligated with BamHI/NotI-digested pIRES-link to yield pIRES-link-zeo. The d2EGFP reporter ORF was introduced into pIRES-link-zeo by amplification of (Clontech 6010-1) with primers gATCgAATTCTCgCgAATggTgAgCAAgCAg ATCCTgAAg (SEQ ID NO:21) and AggCgAATTCAccggT-gTTTAAACTTACACCCACTC gTgCAggCTgCCCAgg (SEQ ID NO:22), and insertion of the EcoRI-digested d2EGFP cassette into the EcoRI site in the pIRES-link-zeo plasmid. This created the CMV Control (CMV-d2EGFP-IRES-Zeo).

The effect of the LexA-P300HAT on gene expression is determined with a plasmid that differs significantly from the plasmids in FIG. 1A. In FIG. 1A, the SV40-Lex-Opener unit is placed downstream from the other expression unit that encompasses the CMV-driven GFP reporter gene. Transcription of both units is then in the same direction. In the novel plasmid (FIG. 6), the transcription of the CMV-driven d2EGFP reporter gene is directed away from the transcription of the SV40-driven LexA-P300HAT opener. In this configuration, the CMV and SV40 promoters are in close proximity. Between these two promoters, LexA binding sites are cloned. Hence, the LexA-P300HAT will influence the expression status of both the CMV-driven reporter gene and the SV40-driven Opener. LexA binding sites (LBS) are amplified from plasmid pREP4-HSF-Luc+(van der Vlag et al., 2000) using primers AGGCGTCGACGTTTCGACTCCCAAGCTTTG (SEQ ID NO:27) and GATCGGCGCGCCGGTACCAT-AGCGGCCGCGAC (SEQ ID NO:28) and cloned between the CMV and SV40 promoters in PP using SalI and AscI.

LexA is amplified from plasmid pEG202 (Bennetzen and Hall, 1982) using primers GATCAAGCTTATGAAGACGT-TAACGGCCAGGC (SEQ ID NO:29) and AGGCACCGGT-CAGCCAGTCGCCGTTGCGAATAACC (SEQ ID NO:30) and cloned downstream of the SV40 promoter in plasmid pPur using HindIII and AgeI creating pPur-LexA. Oligos GATCTCCCCTGAGGAAGTGCACAACCTGAGGCC (SEQ ID NO:31) and GATCTGGCCTCAGGTTGTGCACT- TCCTCAGGGG (SEQ ID NO:32) are ligated into the BamHI site of pPur-LexA to create pPur-LexA-linker. The HAT domain of human p300 (aa934-1652) is pcr amplified from plasmid pCMVβ-p300 (Martinez-Balbá s et al., 2000) using primers GATCACCGGTCAGCCTGCAACTC-CACTTTCCCAGCC (SEQ ID NO:35) and AGGCGCTAGCCTACATGGTGGAC-CACTGGGCTCTTCGG (SEQ ID NO:36) and cloned into pPur-LexA-linker using AgeI and NheI/XbaI creating pPur-LexA-P300-HAT. The entire SV40-LexA-P300-HAT transcription unit is cloned downstream of the LexA binding sites, to create -CMV-d2EGFP-ires-Zeo--LexA-P300HAT (CMV-p300HAT) (FIG. 6).

Transfection and Culture of CHO Cells

The Chinese Hamster Ovary cell line CHO-K1 (ATCC CCL-61) is cultured in HAMS-F12 medium+10% Fetal Calf Serum containing 2 mM glutamine, 100 U/ml penicillin, and 100 micrograms/ml streptomycin at 37° C./5% $CO_2$. Cells are transfected with the plasmids using Lipofectamine 2000 (Invitrogen) as described by the manufacturer. Briefly, cells are seeded in culture vessels and grown overnight to 70 to 90% confluence. Lipofectamine reagent is combined with plasmid DNA at a ratio of 7.5 microliters per 3 micrograms and added after 30 minutes incubation at 250° C. to the cells. After six hours incubation, the transfection mixture is replaced with fresh medium and the transfected cells are incubated further. After overnight cultivation, cells are trypsinized and seeded in serial dilutions into fresh petri dishes with fresh medium with zeocin added to a concentration of 100 µg/ml and the cells are cultured further. When individual colonies become visible (approximately ten to fourteen days after transfection), individual clones are isolated and transferred to 24-well plates in medium containing zeocin. Expression of the d2EGFP reporter gene is assessed approximately four weeks after transfection. After these first measurements, cells are subsequently cultured in medium without selection agent (Zeocin). Expression of the d2EGFP reporter gene is assessed at different times, up to 120 days post-transfection.

Results

FIG. 6 shows that targeting LexA-P300HAT to LexA binding sites upstream of the CMV promoter results in a number of CHO colonies that express slightly higher levels of d2EGFP protein, as compared to the "empty" control without LexA-P300HAT. The average of the d2EGFP signal in the 11 colonies transfected with the CMV Control plasmid is 109 when measured 30 days after transfection. In comparison, the average of the d2EGFP signal in the 15 colonies transfected with the CMV-p300HAT plasmid is 158 when measured 30 days after transfection. However, when followed for an extended period of time, expression levels of both plasmids dropped. The average of the d2EGFP signal in the 11 colonies transfected with the CMV Control plasmid is 28 when measured 120 days after transfection. The average of the d2EGFP signal in the 15 colonies transfected with the CMV-p300HAT plasmid is 70 when measured 120 days after transfection. Hence, the expression level of the plasmid without the LexA-P300HAT Opener dropped a factor of four, whereas the expression level of the plasmid with the LexA-P300HAT Opener dropped a factor of two. We conclude that the LexA-p300HAT conveys more stability of gene expression levels in comparison with the plasmid without Opener, but only to a limited degree. With the CMV promoter, the higher expression levels induced by the LexA-P300HAT Opener is, therefore, limited in time, at least when the cells are cultured in the absence of antibiotic selection pressure.

Example 7

STAR and TRAP Elements Improve Stability Over Time of the p300 HAT-Mediated Increased Gene Expression Levels In this example, we test whether the combination of STAR, TRAP elements and the LexA-P300HAT is able to promote long-term stability of gene expression.

Materials and Methods

Plasmids

Two plasmids are compared in this experiment: the UB6-d2EGFP-ires-Zeo (UB6 Control) vector and the UB6-d2EGFP-ires-Zeo-LexAP300HAT-STAR7-TRAP (UB6-p300HAT-STAR7) (FIG. 7). The configuration of the Opener element in relation to the transcription unit of the reporter gene is similar as in FIG. 6. However, the CMV promoter is replaced by the UB6 promoter (PCR amplified from pUB6V5HisA using primers GATCGGTACCGGCGCGC-CTCCGCGCCGGGTTTTG (SEQ ID NO:43) and AGGC-GAGCTCGGTACCAAGCTTCGTCTAAC (SEQ ID NO:44) and cloned into PPLp300HAT using AscI and SacI creating UB6-p300HAT). Also, 5' STAR7 is cloned into the SalI site and 3' STAR7 is cloned into the PacI site of the UB6-p300HAT construct to create UB6-p300HAT-STAR7. To the STAR7 sequence, the SPA-pause TRAP sequence is added (FIG. 7).

Transfection and Culture of CHO Cells

Transfection and culturing are as in Example 6. Expression of the d2EGFP reporter gene is assessed approximately three weeks after transfection. After these first measurements, cells are subsequently cultured in medium without selection agent (Zeocin). Expression of the d2EGFP reporter gene is assessed at different times, for the last time 95 days after transfection.

Results

FIG. 7 shows that targeting LexA-P300HAT to LexA binding sites upstream of the UB6 promoter results in a number of CHO colonies that express significantly higher levels of d2EGFP protein, as compared to the "empty" UB6 Control without LexA-P300HAT. The average of the d2EGFP signal in the 12 colonies transfected with the UB6 Control plasmid is 70 when measured 25 days after transfection. In comparison, the average of the d2EGFP signal in the 12 colonies transfected with the UB6-p300HAT-STAR7 plasmid is 157 when measured 25 days after transfection. Hence, the combined application of STAR7 and the LexA-P300HAT Opener has a positive effect on the expression level of the reporter protein in stably transfected clones.

When followed for an extended period of time, only the expression levels of the UB6 control plasmid dropped. The average of the d2EGFP signal in the 12 colonies transfected with the UB6 Control plasmid is 31 when measured 95 days after transfection. The average of the d2EGFP signal in the 12 colonies transfected with the UB6-p300HAT-STAR7 plasmid is 207 when measured 95 days after transfection. Hence, the expression level of the plasmid without the LexA-P300HAT Opener dropped significantly, whereas the expression level of the plasmid with the LexA-P300HAT Opener has actually increased ~30%. We conclude that the combined action of STAR7, the Spa/pause TRAP sequence and the LexA-p300HAT Opener conveys a high degree of stability of gene expression levels in comparison with the plasmid without STAR, TRAP sequences and an Opener. At least in context of the UB6 promoter, the higher expression levels induced by STAR7/TRAP and the LexA-P300HAT Opener remains, therefore, stable over time. This demonstrates that application of a combination of Openers, STAR and TRAP elements protect transgenes from silencing during prolonged cultivation. It also demonstrates that this property is independent of antibiotic selection.

Example 8

The Combination of the p300 HAT Opener and a STAR/TRAP Element Improves Copy Number Dependency of Gene Expression Transgene expression units for heterologous protein expression are generally integrated into the genome of the host cell to ensure stable retention during cell division. Integration can result in one or multiple copies of the expression unit being inserted into the genome; multiple copies may or may not be present as tandem arrays. This raises the question whether the transgene is expressed in copy number-dependent or independent fashion. Particularly, clones containing a higher copy number tend to express unstable over time. In this example, we determine the relationship between transgene expression levels and copy number.

Material and Methods

CHO cells were transfected with UB6-d2EGFP-ires-Zeo (UB6 Control) vector and the UB6-d2EGFP-ires-Zeo-LexA-P300HAT-STAR7-TRAP (UB6-p300HAT-STAR7). Individual clones were selected and were cultivated for 95 days, as in Example 7. Cells were harvested, d2EGFP expression was measured and the remaining cells were lysed and the genomic DNA purified using the DNeasy Tissue Kit (QIAGEN 69504) as described by the manufacturer. The copy number of the d2EGFP gene was determined by following a competitive PCR protocol (Fu et al., 1999). The resulting autoradiogram exposed to a phosphorimager screen (Personal F/X, BioRad) and was analyzed by densitometry to determine the relative strength of the d2EGFP DNA bands. The blot was re-hybridized with a probe for actin and the ratio between the d2EGFP and actin signal was taken as the relative copy number.

Results

We determined the copy number of the integrated vectors in the colonies shown in FIG. 8. We found no correlation between the copy number of integrated plasmids and the expression level of d2EGFP in the UB6 Control vector, in which no STAR element was present. This is indicated by the low correlation coefficient (R2) of 0.24. In contrast, there was a good correlation between expression and copy number of d2EGFP in the UB6-p300HAT-STAR7 vector. This is indicated by the high correlation coefficient (R2) of 0.82. Significantly, not only was the d2EGFP expression copy number dependent, more d2EGFP protein was produced per copy. An estimate is that there is a factor three increased d2EGFP expression level per copy in the UB6-p300HAT-STAR7 vector.

This suggests that the combination of STAR7, the Spa/pause TRAP sequence and the LexA-P300HAT Opener confers copy number dependence on the transgene expression units, making transgene expression independent of other transgene copies in tandem arrays and independent of gene-silencing influences at the site of integration. Furthermore, expression per copy increases when the transgene is protected by the combination of STAR7/TRAP and the LexA-P300HAT Opener.

REFERENCES

Angrand P.-O., C. P. Woodroofe, F. Buchholz and A. F. Stewart (1998) Inducible expression based on regulated recombination: a single vector strategy for stable expression in cultured cell. *Nucl. Acid Res.* 26, 3263-3269.

Aranda A. and A. Pascual (2001) Nuclear hormone receptors and gene expression. *Physiol. Rev.* 81, 1269-304.

Bannister A. J. and T. Kouzarides (1996) The CBP co-activator is a histone acetyltransferase. *Nature* 384, 641-643.

Beisel C., A. Imhof, J. Greene, E. Kremmer and F. Sauer (2002) Histone methylation by the *Drosophila* epigenetic transcriptional regulator Ash1. *Nature* 419, 857-862.

Boshart M., F. Weber, G. Jahn, K. Dorsch-Hasler, B. Fleckenstein and W. Schaffner (1985) A very strong enhancer is located upstream of an immediate early gene of human cytomegalovirus. *Cell* 41, 521-30.

Bunker C. A. and R. E. Kingston (1994) Transcriptional repression by *Drosophila* and mammalian Polycomb group proteins in transfected mammalian cells. *Mol. Cell. Biol.* 14, 1721-1732.

Chan A. and T. W. Mak (1989) Genomic organization of the T cell receptor. *Cancer Detect. Prev.* 14, 261-7.

Chevet E., P. H. Cameron, M. F. Pelletier, D. Y. Thomas and J. J. Bergeron (2001) The endoplasmic reticulum: integration of protein folding, quality control, signaling and degradation. *Curr. Opin. Struct. Biol.* 11, 120-4.

Chiba H., M. Muramatsu, A. Nomato and H. Kato (1994) Two human homologues of *Saccharomyces cerevisiae* SWI2/SNF2 and *Drosophila brahma* are transcriptional coactivators cooperating with the estrogen receptor and retinoic acid receptor. *Nucl. Acids Res.* 22, 1815-1820.

Crosby M. A., C. Miller, T. Alon, K. L. Watson, C. P. Verrijzer, R. Goldman-Levi and N. B. Zak (1999) The trithorax group gene moira encodes a *brahma*-associated putative chromatin-remodeling factor in *Drosophila melanogaster*. *Mol. Cell. Biol.* 19, 1159-1170.

Czermin B., R. Melfi, D. McCabe, V. Seitz, A. Imhof and V. Pirrotta (2002) *Drosophila* Enhancer of Zeste/ESC complexes have a histone H3 methyltransferase activity that marks chromosomal Polycomb sites. *Cell* 111, 185-196.

Das G. C., S. K. Niyogi and N. P. Salzman (1985) SV40 promoters and their regulation. *Prog. Nucleic Acid Res. Mol. Biol.* 32, 217-36.

Elfring L. K., R. Deuring, C. M. McCallum, C. L. Peterson and J. W. Tamkun (1994) Identification and characterization of *Drosophila* relatives of the yeast transcriptional activator SNF2/SWI2. *Mol. Cell. Biol.* 14, 2225-34.

European patent application 01202581.3.

Farkas G., J. Gausz, M. Galloni, G. Reuter, H. Gyurkovics and F. Karch (1994) The Trithorax-like gene encodes the *Drosophila* GAGA factor. *Nature* 371, 806-808.

Fu P., P. Senior, R. T. Fernley, G. W. Tregear and G. P. Aldred (1999) Rapid determination of transgene copy number in stably transfected mammalian cells by competitive PCR. *J. Biochem. Biophys. Methods* 40, 101-112.

Fyodorov D. V. and J. T. Kadonaga (2001) The many faces of chromatin remodeling: SWItching beyond transcription. *Cell* 106, 523-525.

Garrick D., S. Fiering, D. I. Martin and E. Whitelaw (1998) Repeat-induced gene silencing in mammals. *Nat. Genet.* 18, 56-9.

Groeneveld E. H. and E. H. Burger (2000) Bone morphogenetic proteins in human bone regeneration. *Eur. J. Endocrinol.* 142, 9-21.

Hynes R. O (1999) Cell adhesion: old and new questions. *Trends Cell. Biol.* 9, M33-7.

Imbalzano A. N., H. Kwon, M. R. Green and R. E. Kingston (1994) Facilitated binding of TATA protein to nucleosomal DNA. *Nature* 370, 481-485.

Ito T., M. Bulger, M. J. Pazin, R. Kobayashi and J. T. Kadonaga (1997) ACF, an ISWI-containing and ATP-utilizing chromatin assembly and remodeling factor. *Cell* 90, 145-155.

Kal et al. (2000) The *Drosophila Brahma* complex is an essential coactivator for the trithorax group protein Zeste. *Genes and Dev.* 14, 1058-1071.

Kaufman R. J. (2000) Overview of vector design for mammalian gene expression. *Mol. Biotechnol.* 16, 151-60.

Kaufman R. J. (1990) Selection and co-amplification of heterologous genes in mammalian cells. *Methods in Enzymology* 185, 536-566.

Kaufman R. J. and P. A. Sharp (1982) Construction of a modular dihydrofolate reductase cDNA gene: analysis of signals utilized for efficient expression. *Mol. Cell. Biol.* 2, 1304-19.

Kennison J. A. and J. W. Tamkun (1992) Trans-regulation of homeotic genes in *Drosophila*. *The New Biologist* 4, 91-96.

Kingston R. E., C. A. Bunker and A. N. Imbalzano (1996) Repression and activation by multiprotein complexes that alter chromatin structure. *Genes and Dev.* 10, 905-920.

Kwon et al. (1994) Nucleosome disruption and enhancement of activator binding by a human SWI/SNF complex. *Nature* 370, 477-481.

Lachner M., D. O'Carroll, S. Rea, K. Mechtler and T. Jenuwein (2001) Methylation of histone H3 lysine 9 creates a binding site for HP1 proteins. *Nature* 410, 116-120.

Lillie J. W and M. R. Green (1989) Transcription activation by the adenovirus E1a protein. *Nature* 338, 39-44.

Liu D. T. (1992) Glycoprotein pharmaceuticals: scientific and regulatory considerations, and the US Orphan Drug Act. *Trends Biotechnol.* 10, 114-20.

Lopez de Quinto S. and E. Martinez-Salas (1998) Parameters influencing translational efficiency in aphthovirus IRES-based bicistronic expression vectors *Gene* 217, 51-6.

Martin D. I. and E. Whitelaw (1996) The vagaries of variegating transgenes. *Bioessays* 18, 919-23.

Martinez-Salas E. (1999) Internal ribosome entry site biology and its use in expression vectors. *Curr. Opin. Biotechnol.* 10, 458-64.

Mazo A. M., D. H. Huang, B. A. Mozer and I. B. Dawid (1990) The trithorax gene, a trans-acting regulator of the bithorax complex in *Drosophila*, encodes a protein with zinc-binding domains. *Proc. Natl. Acad. Sci. U.S.A.* 87, 2112-2116.

McBurney M. W., T. Mai, X. Yang and K. Jardine (2002) Evidence for repeat-induced gene silencing in cultured mammalian cells: inactivation of tandem repeats of transfected genes. *Exp. Cell. Res.* 274, 1-8.

Migliaccio A. R., C. Bengra, J. Ling, W. Pi, C. Li, S. Zeng, M. Keskintepe, B. Whitney, M. Sanchez, G. Migliaccio and D. Tuan (2000) Stable and unstable transgene integration sites in the human genome: extinction of the Green Fluorescent Protein transgene in K562 cells. *Gene* 256, 197-214.

Mizuguchi H., Z. Xu, A. Ishii-Watabe, E. Uchida and T. Hayakawa (2000) IRES-dependent second gene expression is significantly lower than cap-dependent first gene expression in a bicistronic vector. *Mol. Ther.* 1, 376-82.

Mizutani T., T. Ito, M. Nishina, M. Yamamichi, A. Watanabe and H. Iba (2002) Maintenance of integrated proviral gene expression requires Bmm, a catalytic subunit of SWI/SNF complex. *J. Biol. Chem.* 277, 15859-15864.

Muller J., G. M. Hart, N. J. Francis, M. L. Vargas, A. Sengupta, B. Wild, E. L. Miller, M. B. O'Connor, R. E. Kingston and A. J. Simon (2002) Histone Methyltransferase Activity of a *Drosophila* Polycomb Group Repressor Complex. *Cell* 111, 197-208.

Nakamura T., J. Blechman, S. Tada, T. Rozovskaia, T. Itoyama, F. Bullrich, A. Mazo, C. M. Croce, B. Geiger and E. Canaani (2000) huASH1 protein, a putative transcription factor encoded by a human homologue of the *Drosophila* ash1 gene, localizes to both nuclei and cell-cell tight junctions. *Proc. Natl. Acad. Sci U.S.A.* 97, 7284-7289.

Nan X., H. Ng, C. A. Johnson, C. D. Laherty, B. M. Turner, R. N. Eisenman and A. Bird (1998) Transcriptional repression by the methyl-CpG-binding protein MeCP2 involves a histone deacetylase complex. *Nature* 393, 386-389.

Petruk S., Y. Sedkov, S. Smith, S. Tillib, V. Kraesvski, T. Nakamura, E. Canaani, C. M. Croce and A. Mazo (2001) Trithorax and dCBP acting in a complex to maintain expression of a homeotic gene. *Science* 294, 1331-1334.

Quinn J., A. M. Fyrverg, R. W. Ganster, M. C. Schmidt and C. L. Peterson (1996) DNA-binding properties of the yeast SWI/SNF complex. *Nature* 379, 844-847.

Rees S., J. Coote, J. Stables, S. Goodson, S. Harris and M. G. Lee (1996) Bicistronic vector for the creation of stable mammalian cell lines that predisposes all antibiotic-resistant cells to express recombinant protein. *Biotechniques* 20, 102-4, 106, 108-10.

Sewalt R. G. A. B., M. Lachner, M. Vargas, C. M. Hamer, M. Melcher, T. Jenuwein and A. P. Otte (2002) Selective interactions between vertebrate Polycomb homologs and the SUV39H1 HMTase suggest histone H3-K9 methylation to contribute to chromosomal targeting of Polycomb-group proteins. *Mol. Cell. Biol.* 22, 5539-5553.

Schorpp M., R. Jager, K. Schellander, J. Schenkel, E. F. Wagner, H. Weiher and P. Angel (1996) The human ubiquitin C promoter directs high ubiquitous expression of transgenes in mice *Nucleic Acids Res.* 24, 1787-8.

Sheeley D. M., B. M. Merrill and L. C. Taylor (1997) Characterization of monoclonal antibody glycosylation: comparison of expression systems and identification of terminal alpha-linked galactose. *Anal. Biochem.* 247, 102-10.

Sif S., A. J. Saurin, Imbalzano and R. E. Kingston (2001) Purification and characterization of mSin3A-containing Brg1 and hBrm chromatin remodeling complexes. *Genes and Dev.* 15, 603-618.

Strutzenberger K., N. Borth, R. Kunert, W. Steinfellner and H. Katinger (1999) Changes during subclone development and ageing of human antibody-producing recombinant CHO cells. *J. Biotechnol.* 69, 215-26.

Tamkun J. W., R. Deuring, M. P. Scott, Kissinger, A. M. Pattatucci, T. C. Kaufinan and J. A. Kennison (1992) *Brahma*: A regulator of *Drosophila* homeotic genes structurally related to the yeast transcriptional activator SNF2/SWI2. *Cell* 68, 561-572.

Taunton J., C. A. Hassig and S. L. Schreiber (1996) A mammalian histone deacetylase related to the yeast transcriptional regulator Rpd3p. *Science* 272, 408-411.

Thotakura N. R. and D. L. Blithe (1995) Glycoprotein hormones: glycobiology of gonadotrophins, thyrotrophin and free alpha subunit. *Glycobiology* 5, 3-10.

Treisman J. E., A. Luk, G. M. Rubin and U. Heberlein (1997) Eyelid antagonizes wingless signaling during *Drosophila* development and has homology to the Bright family of DNA-binding proteins. *Genes Dev.* 11, 1949-1962.

Varga-Weisz P. D., M. Wilm, E. Bonte, K. Dumas, M. Mann and P. B. Becker (1997) Chromatin-remodeling factor CHRAC contains the ATPases ISWI and topoisomerase II. *Nature* 388, 598-602.

Venkatesan A. and A. Dasgupta (2001) Novel fluorescence-based screen to identify small synthetic internal ribosome entry site elements. *Mol. Cell. Biol.* 21, 2826-37.

Whitelaw E., H. Sutherland, M. Kearns, H. Morgan, L. Weaving and D. Garrick (2001) Epigenetic effects on transgene expression. *Methods Mol. Biol.* 158, 351-68.

Wright A. and S. L. Morrison (1997) Effect of glycosylation on antibody function: implications for genetic engineering. *Trends Biotechnol.* 15, 26-32.

Yang X.-J., V. V. Ogryzko, J. Nishikawa, B. H. Howard and Y. Nakatani (1996) A p300/CBP-associated factor that competes with the adenoviral oncoprotein E1A. *Nature* 382, 319-324.

Table 1. STAR elements used for testing in the examples.
SEQ ID NO:1 (STAR4), SEQ ID NO:2 (STAR6), SEQ ID NO:3 (STAR7), SEQ ID NO:4 (STAR12), SEQ ID NO:5 (STAR18), SEQ ID NO:6 (STAR35), SEQ ID NO:7 (STAR40)

Table 2. Preferred TRAP sequences.
Lambda fragment 35711-38103 (SEQ ID NO:8), Lambda fragment 22425-27972 (SEQ ID NO:9), A combined synthetic polyA (SPA) sequence (version 1) and a pausing signal from the human α2 globin gene (SEQ ID NO:10), A combined synthetic polyA (SPA) sequence (version 2) and a pausing signal from the human α2 globin gene (SEQ ID NO:11), >Inter histone H3FA-H4F (SEQ ID NO:12) (genome.ucsc.edu/cgi-bin/hgTracks?hgsid=13148179&position=chr6%3A26063) (Chromosome 6; by 26063887-26064766) Inter histone H1F4-H2BFB (chr6:26214737-26215909) (SEQ ID NO:13)

---

What is claimed:

1. A method for expressing a heterologous polypeptide in a cell, said method comprising:
   culturing a transfected cell clone to allow expression of the heterologous polypeptide, wherein cells of the transfected cell clone contain integrated into their genomes a transfected nucleic acid molecule comprising:
      a promoter functionally linked to an open reading frame encoding the heterologous polypeptide, said promoter comprising a human cytomegalovirus, a simian virus 40, an ubiquitin C, or an elongation factor one-alpha promoter, and
      a binding site for a p300/CBP protein, a P/CAF protein, or CBP, and wherein the cells of said transfected cell clone comprise said p300/CBP protein, P/CAF protein, or CBP,
   wherein the transfected nucleic acid molecule comprising the promoter functionally linked to an open reading frame encoding the heterologous polypeptide is flanked on one or both sides by a Stabilizing Anti-Repressor (STAR) molecule comprising a nucleic acid molecule selected from the group consisting of SEQ ID NO:1, SEQ ID NO:2, SEQ ID NO:3, SEQ ID NO:4, SEQ ID NO:5, SEQ ID NO:6, and SEQ ID NO:7.

2. The method according to claim 1, wherein said cells comprise at least a functional part of a p300/CBP protein, P/CAF protein, or CBP fused to a sequence specific nucleic acid binding domain, and wherein the sequence specific nucleic acid binding domain comprises a LexA binding site or a Gal4 binding site.

3. The method according to claim 1, wherein the cells of the transfected cell clone further contain nucleic acid comprising a promoter functionally linked to an open reading frame encoding a further polypeptide.

4. The method according to claim 1, wherein said transfected nucleic acid molecule comprises a bicistronic gene or multicistronic gene.

5. The method according to claim 3, wherein said heterologous polypeptide, said further polypeptide, or both said heterologous polypeptide and said further polypeptide, is a member of a multimeric protein.

6. The method according to claim 1, wherein said heterologous polypeptide is selected from the group consisting of an immunoglobulin heavy chain, an immunoglobulin light chain, an antigen binding part, and a combination of any thereof.

7. The method according to claim 1, wherein said binding site is upstream of the promoter.

8. The method according to claim 1, further comprising:
   harvesting said heterologous polypeptide from said cells or a culture supernatant associated with said cells.

9. The method according to claim 1, wherein said transfected nucleic acid molecule further comprises:
   (i) at least one TRAnscription Pause (TRAP) molecule and wherein said TRAP molecule is located downstream of an open reading frame in said transfected nucleic acid in an orientation that can at least in part prevent the formation of anti-sense RNA, or
   (ii) at least one TRAP molecule and wherein said TRAP molecule is located upstream of said promoter, and present in an orientation that can at least in part prevent transcription to enter said promoter and open reading frame, or
   (iii) both (i) and (ii)
   wherein the at least one TRAP molecule comprises a molecule selected from the group consisting of SEQ ID NO:8, SEQ ID NO:9, SEQ ID NO:10, SEQ ID NO:11, SEQ ID NO:12, and SEQ ID NO:13.

* * * * *

UNITED STATES PATENT AND TRADEMARK OFFICE
CERTIFICATE OF CORRECTION

| | |
|---|---|
| PATENT NO. | : 8,263,393 B2 |
| APPLICATION NO. | : 11/156910 |
| DATED | : September 11, 2012 |
| INVENTOR(S) | : Arie Pieter Otte et al. |

It is certified that error appears in the above-identified patent and that said Letters Patent is hereby corrected as shown below:

In the specification:

COLUMN 39, LINE 61, Change "Bmm," to --Brm,--

Signed and Sealed this
Second Day of April, 2013

Teresa Stanek Rea
*Acting Director of the United States Patent and Trademark Office*